(12) United States Patent
Maxfield et al.

(10) Patent No.: US 10,124,019 B2
(45) Date of Patent: Nov. 13, 2018

(54) COMPOSITIONS AND THEIR USE FOR REMOVING CHOLESTEROL

(71) Applicant: Cornell University, Ithaca, NY (US)

(72) Inventors: Frederick Maxfield, Chappaqua, NY (US); J. David Warren, New York, NY (US)

(73) Assignee: Cornell University, Ithaca, NY (US)

( * ) Notice: Subject to any disclaimer, the term of this patent is extended or adjusted under 35 U.S.C. 154(b) by 247 days.

(21) Appl. No.: 14/865,712

(22) Filed: Sep. 25, 2015

(65) Prior Publication Data

US 2016/0143942 A1 May 26, 2016

Related U.S. Application Data

(62) Division of application No. 13/322,793, filed as application No. PCT/US2010/036550 on May 28, 2010.

(60) Provisional application No. 61/181,996, filed on May 28, 2009.

(51) Int. Cl.
| | | |
|---|---|---|
| *A61K 31/724* | (2006.01) | |
| *A61K 47/61* | (2017.01) | |
| *A61K 31/4045* | (2006.01) | |
| *A61K 31/165* | (2006.01) | |
| *A61K 31/721* | (2006.01) | |
| *A61K 31/715* | (2006.01) | |
| *A61K 47/54* | (2017.01) | |

(52) U.S. Cl.
CPC .......... *A61K 31/724* (2013.01); *A61K 31/165* (2013.01); *A61K 31/4045* (2013.01); *A61K 31/715* (2013.01); *A61K 31/721* (2013.01); *A61K 47/549* (2017.08); *A61K 47/61* (2017.08)

(58) Field of Classification Search
CPC ...... A61K 31/724; A61K 47/36–47/40; A61K 47/56–47/61
See application file for complete search history.

(56) References Cited

U.S. PATENT DOCUMENTS

| | | |
|---|---|---|
| 5,710,268 A | 1/1998 | Wimmer |
| 2002/0151523 A1 | 10/2002 | Davis et al. |
| 2006/0210527 A1* | 9/2006 | Davis ........................ B82Y 5/00 424/78.27 |
| 2008/0058427 A1 | 3/2008 | Cheng et al. |
| 2008/0171067 A1 | 7/2008 | Govindan et al. |
| 2009/0247603 A1* | 10/2009 | Joshi ..................... A61K 9/2013 514/423 |

FOREIGN PATENT DOCUMENTS

| | | |
|---|---|---|
| WO | WO 02/49676 A2 | 6/2002 |
| WO | WO 2004/022099 A2 | 3/2004 |
| WO | WO 2007/082897 A2 | 7/2007 |
| WO | WO 2009/011702 A1 | 1/2009 |

OTHER PUBLICATIONS

Ohtani, Y. et al "Differential effects of alpha-, beta- and gamma-cyclodextrins . . . " Eur. J. Biochem. (1989) vol. 186, pp. 17-22.*
Kida, T. et al "A facile synthesis of novel cyclodextrin derivatives . . . " Chem. Comm. (2003) pp. 3020-3021.*
Rodriguez-Lucena, D. et al "Size-tunable trehalose-based nanocavities . . . " JOC (2009) vol. 74, pp. 2997-3008.*
Ramirez, H. et al "Preparation of beta-cyclodextrin-dextran polymers . . . " (2007) vol. 59, pp. 597-605.*
Vyas, A. et al "Cyclodextrin based novel drug delivery systems" (2008) vol. 62, pp. 23-42.*
Vanier, M. et al "Niemann-Pick disease type C" Clin. Genet., vol. 64, pp. 269-281. (Year: 2003).*
Camargo, F. et al "Cyclodextrin in the treatment of a mouse model . . . " Life Sci., vol. 70, pp. 131-142. (Year: 2001).*
Machine translation of WO 2007/082897 (2007).
Lahiani-Skiba, M. et al. "Solubility and dissolution rate of progesterone . . . " Drug Devel. Ind. Pharm. (2006) vol. 32, pp. 1043-1058.
Chariot, A. et al "Controlled synthesis and inclusion ability of hyaluronic acid . . . " Biomacromolecules (2006) vol. 7, pp. 907-913.
International Search Report dated Feb. 25, 2011 issued in PCT/US2010/0360550.

* cited by examiner

*Primary Examiner* — Leigh C Maier
(74) *Attorney, Agent, or Firm* — Scully Scott Murphy & Presser

(57) ABSTRACT

The invention is directed to compositions that function to remove cholesterol from a mammal suffering from an elevated cholesterol level. The composition includes a polysaccharide having attached thereto at least one cyclic oligosaccharide. In a particular embodiment, the foregoing composition further includes at least one cell-targeting agent. The invention is also directed to methods that utilize these compositions for removing or reducing cholesterol and other lipids in a mammal suffering from an elevated level of cholesterol and/or other lipid.

22 Claims, 65 Drawing Sheets

Specification includes a Sequence Listing.

B  NPC1
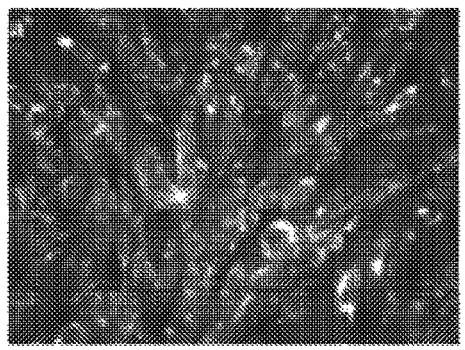 Control
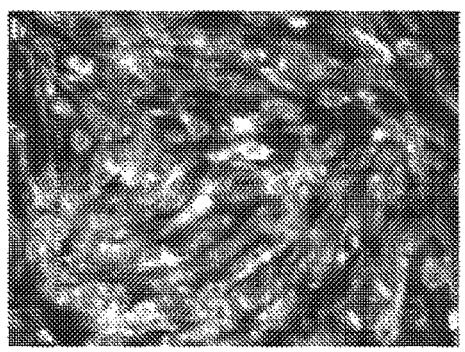 MβCD/ cholesterol no chase
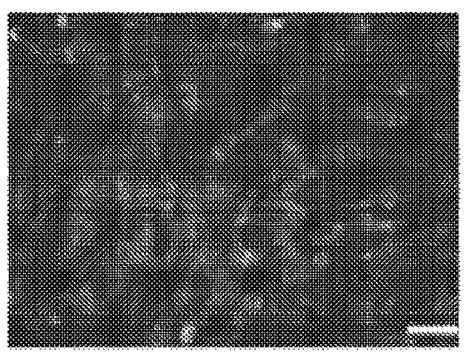 MβCD/ cholesterol with 24 h chase
FIGURE 10B D  NPC2
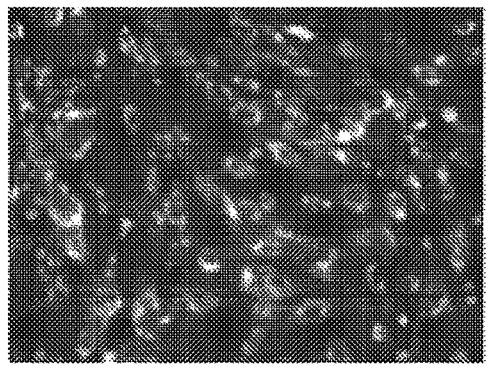 Control
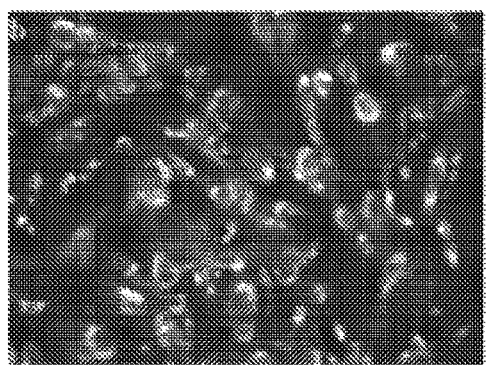 MβCD/ cholesterol no chase
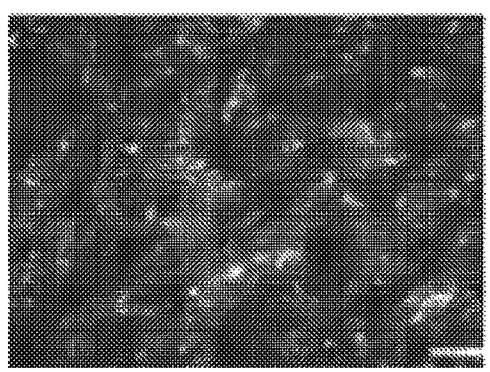 MβCD/ cholesterol with 24 h chase
FIGURE 10D

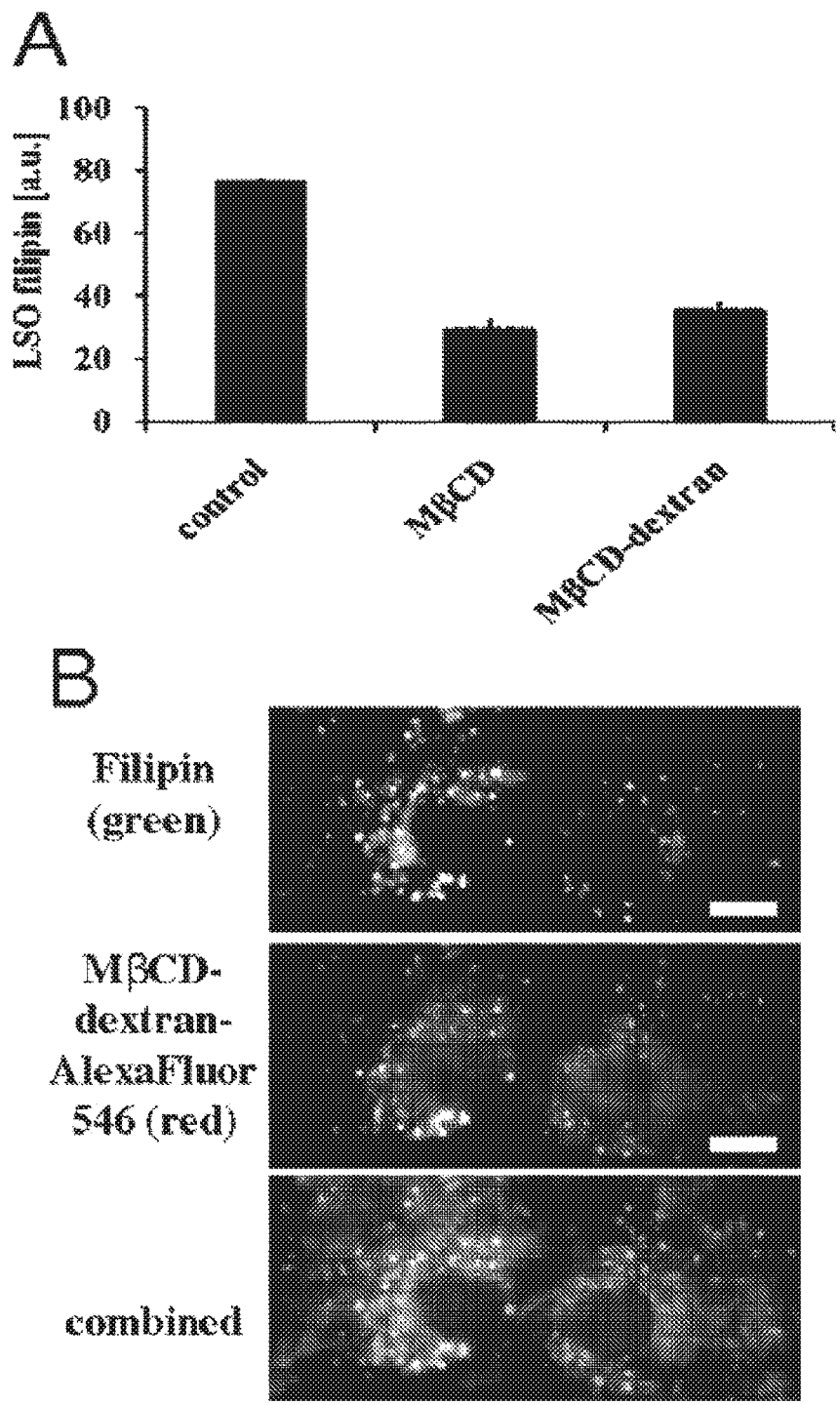
FIGURES 11A-B

A.

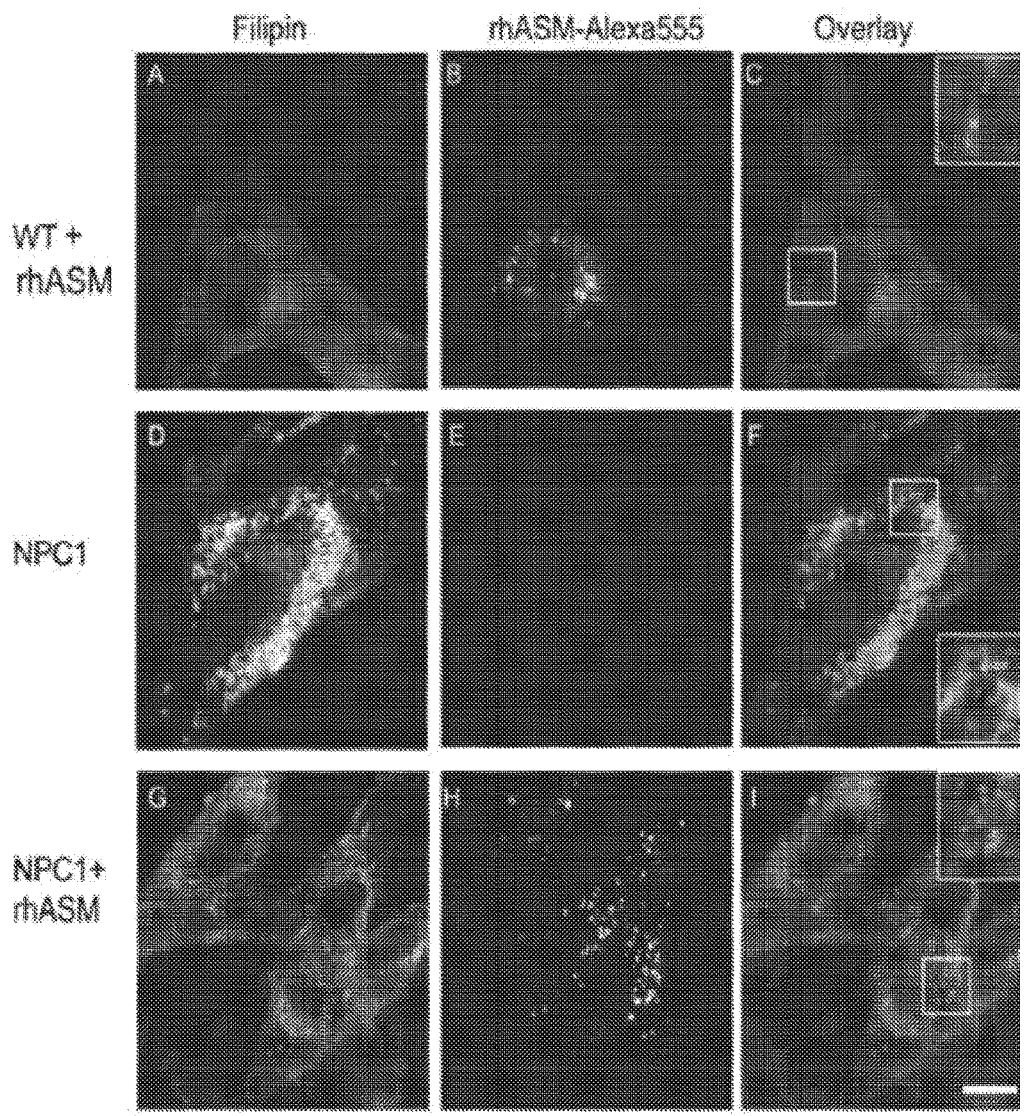
FIGURES 28A-I

31A

31B

COMPOSITIONS AND THEIR USE FOR REMOVING CHOLESTEROL

CROSS REFERENCE TO RELATED APPLICATION

This application is a divisional of U.S. application Ser. No. 13/322,793 filed Nov. 28, 2011, which is a National Phase of PCT/US2010/036550 filed May 28, 2010, which claims the benefit of priority from U.S. Provisional Application No. 61/181,996, filed on May 28, 2009.

GOVERNMENT SUPPORT

This invention was made with government support under GM079238 awarded by the National Institutes of Health. The government has certain rights in the invention.

INCORPORATION BY REFERENCE OF SEQUENCE LISTING

The Sequence Listing in the ASCII text file, named as 24150A_4800_06 US_SequenceListing ST25.txt of 1 KB, created on Dec. 30, 2015, and submitted to the United States Patent and Trademark Office via EFS-Web, is incorporated herein by reference.

FIELD OF THE INVENTION

The present invention relates, generally, to compositions useful for removal or reduction of cholesterol in living tissue, as well as methods for their use in treating a mammal suffering from an elevated level of cholesterol as caused by environmental or genetic factors.

BACKGROUND OF THE INVENTION

Several conditions and disorders are characterized by an elevated level of cholesterol in tissues of the body. New, safer, and more effective methods for reducing cholesterol levels in individuals with elevated levels of cholesterol (e.g., hypercholesterolemia and atherosclerosis) are continually sought. Furthermore, there are continuing efforts to treat individuals suffering from inherited disorders that exhibit as a primary symptom an accumulation of lipids in tissues and cells of the body. These inherited disorders typically belong to the class of lipid storage disorders (LSDs), of which a notable example is Niemann-Pick (NP) disease. The etiology of LSDs is generally a malfunction of the degradative function of the lysosome, and more specifically, a result of an insufficient production of, or diminished function of, a metabolizing enzyme of the lysosome.

SUMMARY OF THE INVENTION

The invention is directed, in a first aspect, to compositions that function to remove cholesterol from a mammal suffering from an elevated cholesterol level. In a particular embodiment, the composition includes a polysaccharide having attached thereto at least one cyclic oligosaccharide. In a further embodiment, the foregoing composition further includes at least one cell-targeting agent. Alternatively, the composition includes an active portion containing a polysaccharide having attached thereto at least one cyclic oligosaccharide, wherein at least one cell-targeting agent is attached to the active portion.

In a second aspect, the invention is directed to a pharmaceutical composition of any of the above-described compositions. The pharmaceutical composition includes the above-described composition in a pharmaceutically acceptable vehicle.

In a third aspect, the invention is directed to methods for removing cholesterol from mammalian tissue, or treating a mammal suffering from an elevated cholesterol level or suffering from a lysosomal storage disorder, by administering to the mammal any of the pharmaceutical compositions described above.

In a fourth aspect, the invention is directed to methods for removing cholesterol from mammalian tissue, or treating a mammal suffering from an elevated cholesterol level or suffering from a lysosomal storage disorder, by administering to the mammal at least one histone deacetylase (HDAC) inhibitor.

In a fifth aspect, the invention is directed to methods for removing cholesterol from mammalian tissue, or treating a mammal suffering from an elevated cholesterol level or suffering from a lysosomal storage disorder, by administering to the mammal at least one sphingomyelinase enzyme.

BRIEF DESCRIPTION OF THE FIGURES

FIG. 11 A, B. MβCD-dextran localization and effects on LSO filipin in NPC1-defective cells. (A) Cells were treated for 2 days with 50 µM MβCD or 50 µM MβCD conjugated to dextran fixed with paraformaldehyde, stained, and imaged. Cholesterol accumulation in LSOs was measured by quantifying filipin fluorescence. Data represent averages±SEM of one representative experiment (n=8, where n is total number of wells per condition used for quantification). (B) Cells were incubated with AlexaFluor546-MβCD-dextran for 15 hours followed by a 3-hour chase in growth medium. The cells were fixed and imaged by epifluorescence microscopy. The MβCD concentration was 300 µM, with ≈2 MβCD per 72-kDa dextran chain. (Scale bars, 11 µm.)

FIG. 31A is a generalized structure depicting a cyclic oligosaccharide (C) embedded within a polysaccharide chain ($P_1$ and $P_2$)

DETAILED DESCRIPTION OF THE INVENTION

In one aspect, the invention is directed to a composition having an active portion therein that includes a polysaccharide having attached thereto at least one cyclic oligosaccharide. In particular embodiments, at least one cell-targeting agent is attached to the foregoing active portion.

Figure 31A:
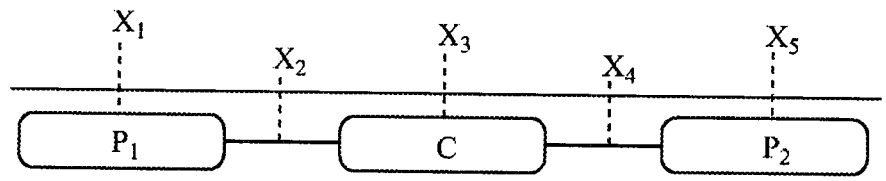
FIGS. 31A, B.

In one set of embodiments, the cyclic oligosaccharide is embedded within the structure of the polysaccharide chain. In this embodiment, the cyclic oligosaccharide is considered to be non-pendant. A generalized structure depicting the foregoing embodiment is provided in FIG. 31A.

In the above representation, $P_1$ and $P_2$ each represent at least one polysaccharide unit, wherein $P_1$ and $P_2$ are structurally the same or different. C represents a cyclic oligosaccharide, or alternatively, more than one (e.g., two, three, or more) cyclic oligosaccharides bound to each other either directly or via one or more linkers. In particular embodiments, at least one of $X_1$, $X_2$, $X_3$, $X_4$, and $X_5$ represents a cell-targeting agent, such as M6P. One or more of $X_1$, $X_2$, $X_3$, $X_4$, and $X_5$ can alternatively, or in addition, (i.e., optionally) represent a fluorophore, or other functional moiety, such as additional cyclic oligosaccharide groups. Each of $X_1$, $X_2$, $X_3$, $X_4$, and $X_5$ can also represent a multiplicity (e.g., two, three, or more) of any of the foregoing groups. The dashed lines to each of $X_1$, $X_2$, $X_3$, $X_4$, and $X_5$ indicate that these groups may or may not be present, and, if present, may be attached to any portion of the group to which they are bound. Each of the solid lines connecting $P_1$ and $P_2$ with C represents at least one direct bond or linker. The representation in formula (1) is meant to be non-limiting by depicting a minimum set of features that can be expanded upon in numerous ways. For example, additional embedded cyclic oligosaccharides may be included, or additional C or P groups may be bound to any of $X_1$, $X_2$, $X_3$, $X_4$, and $X_5$.

Figure 31B:
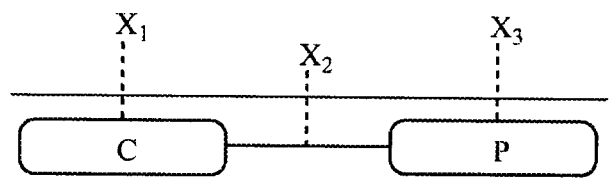
FIG. 31B is a generalized structure depicting a cyclic oligosaccharide (C) pendant to a polysaccharide chain (P), wherein the X variables in these figures represent cell-targeting agents.

In another set of embodiments, the cyclic oligosaccharide is pendant to the polysaccharide chain. A generalized structure depicting the foregoing embodiment is provided in FIG. 31B.

In the above representation, P represents a polysaccharide and C represents at least one cyclic oligosaccharide bound to P directly or via one or more linkers. Alternatively, or in addition, C represents more than one cyclic oligosaccharide bound to each other either directly or via one or more linkers. In particular embodiments, at least one of $X_1$, $X_2$, and $X_3$ represents a cell-targeting agent. One or more of $X_1$, $X_2$, and $X_3$ can alternatively, or in addition (i.e., optionally) represent a fluorophore, or other functional moiety, such as additional cyclic oligosaccharide groups. In this embodiment, $X_1$ is not considered as another P group, although, $X_2$ and/or $X_3$ could also represent one or more P groups. Each of $X_1$, $X_2$, and $X_3$ can also represent a multiplicity (e.g., two, three, or more) of any of the foregoing groups. The dashed lines to each of $X_1$, $X_2$, and $X_3$ indicate that these groups may or may not be present, and, if present, may be attached to any portion of the group to which they are bound. The solid line connecting P with C represents at least one direct bond or linker. The representation in formula (2) is meant to be non-limiting by depicting a minimum set of features that can be expanded upon in numerous ways. For example, an additional P group may be bound to $X_2$ and/or $X_3$, or an additional C group may be bound to $X_1$, $X_2$, and/or $X_3$.

The cyclic oligosaccharide, as defined herein, is a chemical moiety containing at least three monosaccharide units connected directly or via one or more linkers to each other such that the monosaccharide units are arranged in a cyclic pattern. The number of monosaccharide units linked in a cyclic pattern can be, for example, four, five, six, seven, eight, nine, ten, and higher numbers (e.g., up to 12, 15, 18, or 20 units). The monosaccharide can be, for example, an aldose or a ketose, and, in addition, either a triose, tetrose, pentose, hexose, or heptose. Typically, the monosaccharide considered herein contains at least four, five, six, or seven carbon atoms. Some specific examples of monosaccharides include glucose, fructose, galactose, mannose, ribose, maltose, arabinose, xylose, erythrose, xylulose, and ribulose. In one embodiment, the cyclic oligosaccharide contains only one type of monosaccharide connected in a cyclic pattern. In another embodiment, the cyclic oligosaccharide contains more than one type of monosaccharide (e.g., two, three, or more) connected in a cyclic pattern. The monosaccharide can be in a D- or L-configuration, although the D-configuration is more typical. The monosaccharide units can be connected to each other by either an alpha (α) or beta (β) linkage, or a combination thereof, although an exclusive alpha linkage is more typical.

In some embodiments, one or more of the monosaccharide units of the cyclic oligosaccharide can be derivatized. In one set of embodiments, at least one of the monosaccharide units is derivatized by containing a modified hydroxyl group in which the hydrogen atom of the hydroxyl group is replaced with a hydrocarbon group or inorganic group. Some suitable types of hydrocarbon groups include those containing at least one, two, three, four, five, or six carbon atoms, and which can be straight-chained or branched, saturated or unsaturated, and cyclic or acyclic. Some particular hydrocarbon groups considered herein include methyl, ethyl, vinyl, n-propyl, allyl, isopropyl, cyclopropyl, n-butyl, sec-butyl, isobutyl, t-butyl, cyclobutyl, 3-butenyl, n-pentyl, isopentyl, neopentyl, cyclopentyl, cyclopentenyl, n-hexyl, isohexyl, cyclohexyl, phenyl, benzyl, naphthyl, anthracenyl, phenanthrenyl, tolyl, and xylyl groups. In one embodiment, the substituting hydrocarbon group contains only carbon and hydrogen atoms. In another embodiment, the substituting hydrocarbon group includes at least one heteroatom (e.g., at least one O, N, S, or halide atom, or combination thereof). Some examples of heteroatom-substituted hydrocarbon groups include acyl groups (e.g., acetyl and propionyl groups), sulfonyl groups (e.g., methylsulfonyl and tosyl groups), alkyleneoxy groups (e.g., ethylenoxy groups), alkylenehydroxy groups (e.g., —$CH_2CH_2CH_2OH$ or —$CH_2CH_2(OH)CH_3$), alkyleneamino groups (e.g., —$CH_2NH_2$, —$CH_2CH_2NH_2$ or —$CH_2CH_2CH_2NH_2$ groups), alkylenethiol groups (e.g., —$CH_2CH_2CH_2SH$), amido groups (e.g., amide, N-methylamide, and N,N-dimethylamide groups), which link to the hydroxyl oxygen with the amido carbonyl to form a carbamate linkage, amino acids (e.g., a glycine, leucine, serine, or lysine group), dipeptides, oligopeptides, nucleobases (e.g., adenine, guanine, cytosine, thymine, and uracil groups), nucleosides, nucleotides, saccharides (e.g., monosaccharides, disaccharides, and oligosaccharides), lectins, cofactors, and combinations thereof, such as an alkyleneoxy-linked hydroxy, amino, amido, thiol, amino acid, peptide, or saccharide group. A substituting inorganic group can be, for example, a phosphate, diphosphate, triphosphate, phosphate ester, sulfate, sulfonate, metal ion (e.g., lithium, sodium, potassium, magnesium, or calcium ion), or a phosphate-monosaccharide group. Furthermore, the group can be neutral or charged. The charged group can be cationic (e.g., an ammonium group, such as a quaternary ammonium group) or anionic (e.g., a carboxylate group).

In other embodiments, at least one of the monosaccharide units can be derivatized by having one or more hydroxyl groups therein, themselves, replaced by any of the groups described above, or by other groups, such as an N-bound amino, N-bound amido (e.g., N-bound amide or acetylamide group), or a thiol group. In yet other embodiments, at least one of the monosaccharide units can be derivatized by having one or more hydroxyl groups replaced with a hydrogen atom, thereby resulting in a deoxysaccharide unit.

By methods well-known in the art, several of the groups described above, particularly those containing one or more heteroatoms (e.g., amino, amido, ester, thiol, and aldehydic groups) can be used as reactive groups for attaching the cyclic oligosaccharide to another chemical entity, i.e., to the polysaccharide, another cyclic oligosaccharide, a cell-targeting agent, a fluorophore, or other group, either directly or via a linker to any other these groups. Any of the other chemical entities considered as a part of the composition herein (e.g., the polysaccharide, cell-targeting agent, fluorophore, or other group) can contain, or be derivatized to contain, any such reactive groups for the purpose of attaching these groups to each other or to the cyclic oligosaccharide.

Particularly considered herein as cyclic oligosaccharides are the cyclodextrins. As is well-known in the art, cyclodextrins are typically composed of five or more glucose (i.e., glucopyranoside) units connected in a ring structure, linked as in amylose by alpha 1-4 (i.e., α(1→4)) bonds. The cyclodextrins considered herein can conveniently be represented by the following generic formula:

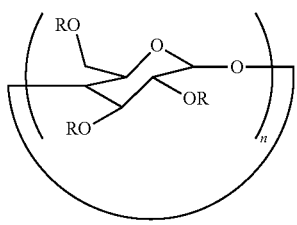

(3)

In generic formula (3) above, the R groups can be independently selected from any of the groups described above, including hydrogen atom, hydrocarbon groups, heteroatom-substituted hydrocarbon groups, inorganic groups, and biochemically-relevant groups. In some embodiments, all of the R groups in the formula are the same, while in other embodiments, at least one of the R groups in the formula is chemically different from other R groups. In further or alternative embodiments, one or more of the OR groups can be replaced by any of the groups described above. Furthermore, since the cyclodextrin (or, more generally, cyclic oligosaccharide) is attached to a polysaccharide, at least one (e.g., one, two, or three) of the R groups represents either a direct bond or a linker that bonds or links, respectively, the cyclodextrin (or, more generally, cyclic oligosaccharide) to the polysaccharide. When generic formula (3) represents a cyclic oligosaccharide, the shown glucose groups can be generically replaced by one or a combination of any of the monosaccharide groups described above. The subscript n denotes the number of monosaccharide units, and can be any number above 3, but more typically a number of 4, 5, 6, 7, 8, 9, or 10, or a particular range therein. The arc shown in generic formula (3) denotes a cyclic arrangement of monosaccharide units.

Some particular cyclodextrin structures are shown in the following sub-generic formulas:

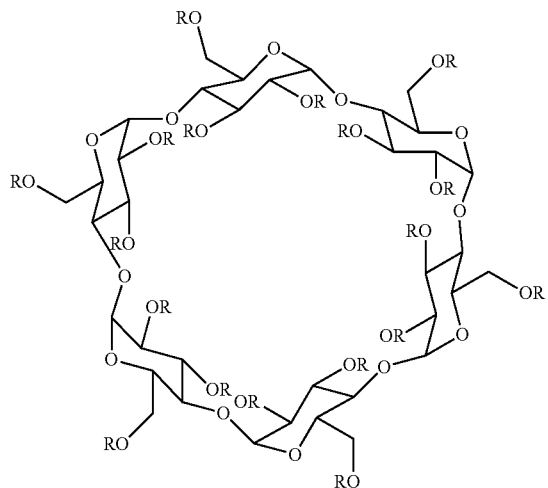

(4)

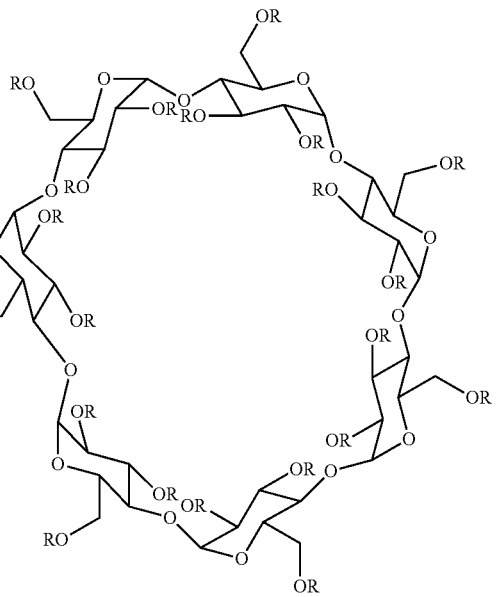

(5)

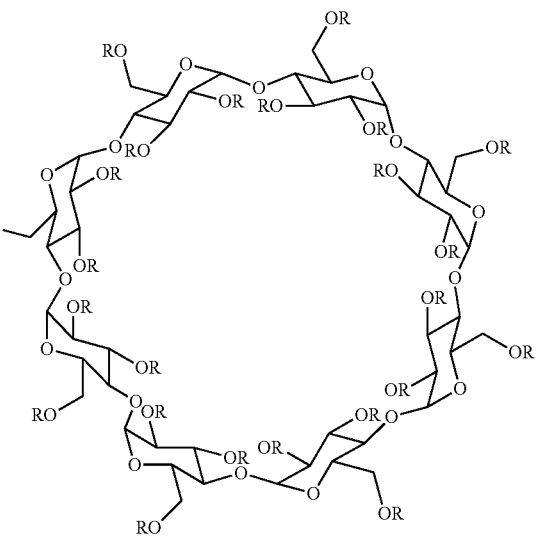

(6)

In formulas (4), (5), and (6), R is as defined above for generic formula (3). Furthermore, any of formulas (4), (5), and (6) can generically represent any cyclic oligosaccharide with the indicated number of saccharide units, by generically replacing the shown glucose groups with one or a combination of any of the monosaccharide groups described above.

The polysaccharide, as defined herein, is a chemical moiety containing a multiplicity (e.g., at least 10, and more typically at least 100) monosaccharide units connected to each other in a linear and/or branched arrangement. In one embodiment, the polysaccharide is a homopolysaccharide by having all of the monosaccharide units as the same type (e.g., all glucose units). In another embodiment, the polysaccharide is a heteropolysaccharide by having different types of monosaccharide units. The polysaccharide considered herein possesses, for example, at least 10, 20, 50, 100, 200, 500, 1000, 5000, 10000, 50000, 100000, 150000, 200000, or higher number of units, or alternatively, molecular weights (or average molecular weights) of at least 100, 200, 500, 1000, 5000, 10000, 20000, 30000, 40000, 50000, 60000, 70000, 80000, 90000, 100000, 150000, 200000, or 500000 Daltons (Da), or the polymer possesses a number of units or molecular weight within a range bounded by any of the foregoing exemplary values. One or more of the monosaccharide units of the polysaccharide can be derivatized in the same manner as described above for the cyclic oligosaccharide. In a particular embodiment, the polysaccharide is functionalized with one, two, three, or higher multiplicity of amino groups. Such a polysaccharide is denoted herein as an "amino polysaccharide".

Particularly considered herein are those polysaccharides constructed solely of glucose units (i.e., a glucan polysaccharide). The glucan polysaccharide can be an α-glucan or β-glucan polysaccharide, although the glucan polysaccharide is more commonly an α-glucan polysaccharide. A particular class of α-glucan polysaccharide considered herein is dextran. As known in the art, a dextran generally consists predominantly of glucose molecules linked predominantly or exclusively by α-1,6-glycosidic linkages. Depending on the type of dextran used, the dextran can contain any of a broad range of branching. The branching generally results from α-1,4 glycosidic linkages, and in some cases, α-1,2 and α-1,3 glycosidic linkages. Other types of α-glucan polysaccharide considered herein are the starches (e.g., amylose and amylopectin), glycogen, and pullulan. Some particular classes of β-glucan polysaccharides considered herein include cellulose, hemicellulose, cellodextrin, chrysolaminarin, lentinan, and zymosan. In some embodiments, at least a portion of the glucose units can be derivatized, such as found in chitin (i.e., a polymer of N-acetylglucosamine). Other derivatized glycans include the glycosaminoglycans, such as chondroitin sulfate, dermatan sulfate, heparin, heparan sulfate, hyaluronic acid, and keratan sulfate.

Other classes of polysaccharides considered herein are the fructans and galactans. Some examples of fructans include the inulins, fructooligosaccharides, and Levan polysaccharide (a homopolysaccharide of fructose with varying degrees of branching). An example of a galactan is the class of galactooligosaccharides.

A particular example of a heteropolysaccharide considered herein is the class of arabinoxylans, which are copolymers of arabinose and xylose. Another heteropolysaccharide considered herein is agarose.

In one set of embodiments, the polysaccharide consists solely of monosaccharide units. In another set of embodiments, the polysaccharide can also include a non-saccharide moiety. For example, the polysaccharide can be a glycoprotein or proteoglycan by containing a proteinaceous component, or the polysaccharide can be a lipopolysaccharide by containing a lipid component.

According to the invention, at least one cyclic oligosaccharide is covalently bound to the polysaccharide. In different embodiments, at least one, two, three, four, five, six, and up to, for example, 10, 15, 20, or 30 cyclic oligosaccharides are bound to the polysaccharide. The cyclic oligosaccharide can be directly bound or linked via a linker to the polysaccharide by any one or more suitable atoms present on the cyclic oligosaccharide. For example, in different embodiments, the cyclic oligosaccharide can be bound to the polysaccharide by one or more of the carbon atoms of the cyclic oligosaccharide (e.g., by replacement of one of the hydroxyl groups of the cyclic oligosaccharide by a binding atom of the polysaccharide or by a binding atom of a linker group linked to the polysaccharide). Alternatively, the cyclic oligosaccharide can be bound to the polysaccharide by one or more of its hydroxyl groups (i.e., oxygen atoms), or the cyclic oligosaccharide can be bound to the polysaccharide by one or more heteroatom-containing groups present on the cyclic oligosaccharide. In the same manner, the polysaccharide can be directly bound or linked via a linker to the cyclic oligosaccharide by any one or more suitable atoms present on the polysaccharide.

Methods for functionalizing a polysaccharide or a cyclodextrin with a linking group are well-known in the art. See, for example, (a) Mocanu G, Vizitiu D, Carpov A. Cyclodextrin polymers. *J. Bioact. Compat. Pol.,* 2001; 16:315-342; (b) Liu Y, Chen Y. Cooperative binding and multiple recognition by bridged bis(β-cyclodextrin)s with functional linkers. *Acc. Chem. Res.,* 2006; 39:681-691. (c) Ozmen E Y, Sezgin M, Yilmaz M. Synthesis and characterization of cyclodextrin-based polymers as a support for immobilization of *Candida rugosa* lipase. *J. Mol. Catal. B-Enzym.,* 2009; 57:109-114. (d) Trotta F, Cavalli R. Characterization and applications of new hyper-cross-linked cyclodextrins. *Compos. Interface,* 2009; 16:39-48. For example, a linker group containing a portion reactive to a hydroxyl group (e.g., a carboxyl group, preferably activated by a carbodiimide) can be reacted with either the cyclodextrin or polysaccharide to form a covalent bond thereto. Alternatively, one or more hydroxyl groups of the cyclodextrin and/or polysaccharide can be activated by known methods (e.g., tosylation) to react with a reactive group (e.g., amino group) on the linker.

Since the linker links at least two chemical entities to each other, the linker generally contains two reactive portions made to react and bond with each chemical entity. In one embodiment, a double-reactive linker is first attached to the cyclodextrin to produce a linker-cyclodextrin compound that is isolated, and then the remaining reactive portion of the linker in the linker-cyclodextrin compound is subsequently reacted with the polysaccharide. In another embodiment, a double-reactive linker is first attached to the polysaccharide to produce a linker-polysaccharide compound that is isolated, and then the remaining reactive portion of the linker in the linker-polysaccharide compound is subsequently reacted with the cyclodextrin. In the two foregoing embodiments, the second reactive portion of the linker is generally protected during reaction of the first reactive group, or alternatively, protection is not necessary in an embodiment where the first and second reactive portions of the linker react with the cyclodextrin differently than with the polysaccharide. Particularly by the latter embodiment, a double-reactive linker may be reacted with both the cyclodextrin and polysaccharide simultaneously to link these groups together. In other embodiments, the linker can have additional reactive groups in order to link to additional cyclodextrin or polysaccharide groups, or to link to a cell-targeting and/or other functional group, such as a fluorophore.

Numerous double-reactive linkers are known in the art. Such linkers can be used for linking any of a variety of groups together when the groups possess, or have been functionalized to possess, groups that can react and link with the reactive linker. Some groups capable of reacting with double-reactive linkers include amino, thiol, hydroxyl, carboxyl, ester, and alkyl halide groups. For example, amino-amino coupling reagents can be employed to link a cyclic oligosaccharide with a polysaccharide (or, for example, any of these groups with a fluorophore or with each other) when each of the groups to be linked possess at least one amino group. Some examples of amino-amino coupling reagents include diisocyanates, alkyl dihalides, dialdehydes, disuccinimidyl suberate (DSS), disuccinimidyl tartrate (DST), and disulfosuccinimidyl tartrate (sulfo-DST), all of which are commercially available. In other embodiments, aminothiol coupling agents can be employed to link a thiol group of one molecule with an amino group of another molecule. Some examples of amino-thiol coupling reagents include succinimidyl 4-(N-maleimidomethyl)-cyclohexane-1-carboxylate (SMCC), and sulfosuccinimidyl 4-(N-maleimidomethyl)-cyclohexane-1-carboxylate (sulfo-SMCC). In yet other embodiments, thiol-thiol coupling agents can be employed to link groups bearing at least one thiol group.

The linker considered herein is any group that can link at least one cyclic oligosaccharide with at least one polysaccharide. In one embodiment, a linker links one cyclic oligosaccharide to one polysaccharide. In another embodiment, a linker links one cyclic oligosaccharide to two or more polysaccharides. In another embodiment, a linker links two or more cyclic oligosaccharides to one polysaccharide. In yet another embodiment, a linker links two or more cyclic oligosaccharides to two or more polysaccharides. In further embodiments to any of the above embodiments, the linker may also link to a cell-targeting agent and/or a fluorophore and/or other chemical moiety. In some embodiments, a first linker links the polysaccharide with the cyclic oligosaccharide, and a separate second linker links a cell-targeting agent with the polysaccharide or the cyclic oligosaccharide. In other embodiments, a linker that links the polysaccharide with the cyclic oligosaccharide also links with a cell-targeting agent. In further embodiments to any of the foregoing embodiments, a separate third linker may be employed to link a fluorophore or other functional group with the polysaccharide or the cyclic oligosaccharide, or alternatively, the first or second linker described above may also link to a fluorophore or other functional entity. The other functional entity can be, for example, a drug or prodrug that would be hydrolyzed and/or otherwise released upon reaching the targeted cell.

In some embodiments, the linker is as small as a single atom (e.g., an —O—, —CH$_2$—, or —NH— linkage), or two or three atoms in length (e.g., an amido, ureido, carbamato, ester, carbonate, sulfone, ethylene, or trimethylene linkage). In other embodiments, the linker provides more freedom of movement by being at least four, five, six, seven, or eight atom lengths, and up to, for example, 10, 12, 14, 16, 18, 20, 22, 24, 26, 28, or 30 atom lengths.

In one embodiment, the linker is a hydrocarbon linker, e.g., as derived from any of the hydrocarbon groups described above by removal of two or more hydrogen atoms therefrom (thus resulting in two or more linking bonds therein). Some examples of hydrocarbon linkers include methylene (—CH$_2$—), ethylene (—CH$_2$CH$_2$—), trimethylene (—CH$_2$CH$_2$CH$_2$—), tetramethylene, pentamethylene, hexamethylene, o-, m-, and p-phenylene, and vinylene.

The hydrocarbon linker may or may not also include heteroatoms. Furthermore, the heteroatoms may or may not be linking atoms. In a particular embodiment, the hydrocarbon linker contains one, two, three, or more amino groups. Some examples of amino-containing linkers include 1,2-ethylenediamine, 1,3-trimethylenediamine, 1,4-tetramethylenediamine, 1,5-pentamethylenediamine, 1,6-hexamethylenediamine, diethylenetriamine, triethylenetetramine, and diaminobenzene linkers. In another particular embodiment, the hydrocarbon linker contains one, two, three, or more oxygen-linking (i.e., —O—) atoms or hydroxy groups. Some examples of such linkers include ethylene glycol, diethylene glycol, triethylene glycol, 2-hydroxypropane, 2,3-dihydroxybutane, dihydroxybenzene, and the polyethylene glycol (i.e., PEG) linkers. In other particular embodiments, the linkers include one, two, three, or more carbonyl groups. Some examples of such linkers include methyl dicarbonyl, ethylene-1,2-dicarbonyl, propylene-1,3-dicarbonyl, and the like.

The linker can also be or include a biological group, such as, for example, a nucleobase, nucleoside, nucleotide, dinucleotide, trinucleotide, tetranucleotide, a higher oligonucleotide, amino acid, dipeptide, tripeptide, tetrapeptide, pentapeptide, hexapeptide, a higher oligopeptide, saccharide, disaccharide, trisaccharide, tetrasaccharide, a higher oligosaccharide, lipid, or fatty acid.

In particular embodiments, the linker is a rigid linker. A rigid linker may be beneficial in some embodiments by reducing the degree of freedom of a linked molecule, or forcing at least two linked groups to remain at fixed distances from each other or from another molecule. Some examples of rigid linkers are those containing aromatic or heteroaromatic rings, such as linkers that include benzene, naphthalene, styrene, divinylbenzene, biphenyl, triphenyl, or other aromatic rings or polycyclic ring systems.

In a particular set of embodiments, the linker has a structure represented by the following generic formula:

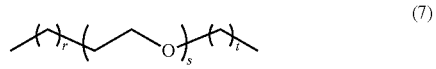

(7)

In formula (7) above, subscripts r, s, and t can independently be 0 or an integer of at least 1, provided that at least one of r, s, and t is not 0. Generally, each end of the linker generally also includes a heteroatom-containing group through which a covalent bond is formed between the linker and groups that are linked. As discussed earlier, such heteroatom-containing groups include, for example, oxo (—O—), amino (e.g., —NH—, or —N(CH$_3$)—), amido (e.g., —C(O)NH— or —C(O)N(CH$_3$)—), ester, ureido, carbonato, sulfonato, and phosphonato groups. In different embodiments, r, s, and t are independently selected from 0, or an integer of 1, 2, 3, 4, 5, 6, 7, 8, 9, 10, 11, 12, 13, 14, 15, or 16, or selected to be within a range therein, provided that at least one of r, s, and t is not 0. In one set of embodiments, r and t are 0, and s represents any of the foregoing non-zero numbers or possible ranges therein. In another set of embodiments, r is 0, while s and t independently represent any of the foregoing non-zero numbers or possible ranges therein. In another set of embodiments, s is zero while at least one of r and t represents any of the foregoing non-zero numbers or possible ranges (thereby resulting in an alkylene structure for formula 7). In another set of embodiments, r, s, and t independently represent any of the foregoing non-zero numbers or possible ranges therein. In particular embodiments, r and t are independently 1, 2, 3, or 4, or a subset therein, while s is selected from any of the foregoing non-zero numbers or possible ranges therein.

The cell-targeting agent (i.e., "targeting agent") is any chemical entity that has the ability to bind to (i.e., "target") a cell. The cell particularly considered herein is a mammalian cell. The type of cell can be any cell in which cholesterol, a cholesterol derivative, or other lipid can accumulate. Some examples of types of cells that can be targeted include cells of the blood, bone marrow, spleen, liver, skin, lungs, nerves (particularly of the peripheral nervous system), and brain. The cell-targeting agent may target any part of the cell, e.g., cell membrane, organelle, or cytoplasmic molecule. In one embodiment, the cell-targeting agent targets a cell in a selective manner. By selectively targeting a cell, the cell-targeting agent can, for example, selectively target certain types of cells over other types of cells, or target certain parts of a cell over other parts of a cell, or both. In other embodiments, the targeting agent targets cells non-selectively, e.g., by targeting components found in most or all cells.

In various embodiments, the targeting agent can be, or include, for example, a peptide, dipeptide, tripeptide (e.g., glutathione), tetrapeptide, pentapeptide, hexapeptide, higher oligopeptide, protein, monosaccharide, disaccharide, trisaccharide, tetrasaccharide, higher oligosaccharide, polysaccharide (e.g., a carbohydrate), nucleobase, nucleoside (e.g., adenosine, cytidine, uridine, guanosine, thymidine, inosine, and S-Adenosyl methionine), nucleotide (i.e., mono-, di-, or tri-phosphate forms), dinucleotide, trinucleotide, tetranucleotide, higher oligonucleotide, nucleic acid, cofactor (e.g., TPP, FAD, NAD, coenzyme A, biotin, lipoamide, metal ions (e.g., $Mg^{2+}$), metal-containing clusters (e.g., the iron-sulfur clusters), or a non-biological (i.e., synthetic) targeting group. Some particular types of proteins include enzymes, hormones, antibodies (e.g., monoclonal antibodies), lectins, and steroids.

Antibodies for use as targeting molecules are generally specific for one or more cell surface antigens. In a particular embodiment, the antigen is a receptor. The antibody can be a whole antibody, or alternatively, a fragment of an antibody that retains the recognition portion (i.e., hypervariable region) of the antibody. Some examples of antibody fragments include Fab, Fc, and F(ab')$_2$. In particular embodiments, particularly for the purpose of facilitating crosslinking of the antibody to the composition described herein, the antibody or antibody fragment can be chemically reduced to derivatize the antibody or antibody fragment with sulfhydryl groups.

In particular embodiments, the targeting agent is a ligand of an internalized receptor of the target cell. For example, the targeting agent can be a targeting signal for acid hydrolase precursor proteins that transport various materials to lysosomes. One such targeting agent of particular interest is mannose-6-phosphate (M6P), which is recognized by mannose 6-phosphate receptor (MPR) proteins in the trans-Golgi. Endosomes are known to be involved in transporting M6P-labeled substances to lysosomes.

In another embodiment, the targeting molecule is a peptide containing an RGD sequence, or variants thereof, that bind RGD receptors on the surface of many types of cells. Other ligands include, for example, transferrin, insulin, amylin, and the like. Receptor internalization is preferred to facilitate intracellular delivery of the inventive composition described herein.

In one set of embodiments, one cell-targeting molecule, or several (e.g., two, three, or more) of the same type of cell-targeting molecule are attached to the inventive composition (particularly on the active portion therein). In other embodiments, two or more different types of targeting molecules are attached to the inventive composition. At least one advantage in using several cell-targeting molecules is that uptake of the inventive composition into cells is generally increased relative to use of a single cell-targeting molecule.

In some embodiments, a fluorophore may be attached to the composition described above. Incorporation of one or more fluorophores can have several purposes, but at least in some embodiments, one or more fluorophores are included in order to quantify cellular uptake and retention of the above-described composition (e.g., by a fluorescence spectroscopic method).

As used herein, a "fluorophore" refers to any species with the ability to fluoresce (i.e., that possesses a fluorescent property). For example, in one embodiment, the fluorophore is an organic fluorophore. The organic fluorophore can be, for example, a charged (i.e., ionic) molecule (e.g., sulfonate or ammonium groups), uncharged (i.e., neutral) molecule, saturated molecule, unsaturated molecule, cyclic molecule, bicyclic molecule, tricyclic molecule, polycyclic molecule, acyclic molecule, aromatic molecule, and/or heterocyclic molecule (i.e., by being ring-substituted by one or more heteroatoms selected from, for example, nitrogen, oxygen and sulfur). In the particular case of unsaturated fluorophores, the fluorophore contains one, two, three, or more carbon-carbon and/or carbon-nitrogen double and/or triple bonds. In a particular embodiment, the fluorophore contains at least two (e.g., two, three, four, five, or more) conjugated double bonds aside from any aromatic group that may be in the fluorophore. In other embodiments, the fluorophore is a fused polycyclic aromatic hydrocarbon (PAH) containing at least two, three, four, five, or six rings (e.g., naphthalene, pyrene, anthracene, chrysene, triphenylene, tetracene, azulene, and phenanthrene) wherein the PAH can be optionally ring-substituted or derivatized by one, two, three or more heteroatoms or heteroatom-containing groups.

In other embodiments, the organic fluorophore is a xanthene derivative (e.g., fluorescein, rhodamine, Oregon green, eosin, and Texas Red), cyanine or its derivatives or subclasses (e.g., streptocyanines, hemicyanines, closed chain cyanines, phycocyanins, allophycocyanins, indocarbocyanines, oxacarbocyanines, thiacarbocyanines, merocyanins, and phthalocyanines), naphthalene derivatives (e.g., dansyl and prodan derivatives), coumarin and its derivatives, oxadiazole and its derivatives (e.g., pyridyloxazoles, nitrobenzoxadiazoles, and benzoxadiazoles), pyrene and its derivatives, oxazine and its derivatives (e.g., Nile Red, Nile Blue, and cresyl violet), acridine derivatives (e.g., proflavin, acridine orange, and acridine yellow), arylmethine derivatives (e.g., auramine, crystal violet, and malachite green), and tetrapyrrole derivatives (e.g., porphyrins and bilirubins). Some particular families of dyes considered herein are the Cy® family of dyes, the Alexa® family of dyes, the ATTO® family of dyes, and the Dy® family of dyes. The ATTO dyes, in particular, can have several structural motifs, including, coumarin-based, rhodamine-based, carbopyronin-based, and oxazine-based structural motifs.

The fluorophore can be attached to the active portion (e.g., to the cyclic oligosaccharide, polysaccharide, a linker, or other group) by any of the linking methodologies known in the art. For example, a commercial mono-reactive fluorophore (e.g., NHS-Cy5) or bis-reactive fluorophore (e.g., bis-NHS-Cy5 or bis-maleimide-Cy5) can be used to link the fluorophore to one or more molecules containing appropriate reactive groups (e.g., amino, thiol, hydroxy, aldehydic, or ketonic groups). Alternatively, the active portion of the inventive composition can be derivatized with one, two, or more such reactive groups, and these reactive portions reacted with a fluorophore containing appropriate reactive groups (e.g., an amino-containing fluorophore).

In another aspect, the invention is directed to a cholesterol-lowering composition that includes a histone deacetylase (HDAC) inhibiting compound. In a first embodiment, the HDAC-inhibiting composition includes trichostatin A (TSA) as a cholesterol-lowering active ingredient. In a second embodiment, the HDAC-inhibiting composition includes suberoylanilide hydroxamic acid (SAHA) as a cholesterol-lowering active ingredient. In a third embodiment, the HDAC-inhibiting composition includes pyroxamide as a cholesterol-lowering active ingredient. In a fourth embodiment, the HDAC-inhibiting composition includes C1-994 (N-Acetyldinaline, a substituted benzamide derivative, i.e. 4-acetylamino-N-(2-aminophenyl) benzamide) as a cholesterol-lowering active ingredient. In a fifth embodiment, the HDAC-inhibiting composition includes Bufexamac (i.e., 2-(4-butoxyphenyl)-N-hydroxyacetamide) as a cholesterol-lowering active ingredient. In a sixth embodiment, the HDAC-inhibiting composition includes LBH-589 (i.e. Panobinostat) as a cholesterol-lowering active ingredient. In other embodiments, the HDAC-inhibiting composition includes two or more of any of the foregoing cholesterol-lowering compounds. In yet other embodiments, one or more of the HDAC-inhibiting compounds are combined with the cyclic oligosaccharide-polysaccharide composition described above as a pharmaceutical composition for lowering cholesterol in a mammal.

In another aspect, the invention is directed to a cholesterol-lowering composition that includes a sphingomyelinase (SMase). As known in the art, cholesterol-enriched NPC cells have a secondary, post-translational defect in the activity of another lysosomal enzyme, acid SMase (J. W. Reagan, Jr., et al., Posttranslational regulation of acid sphingomyelinase in Niemann Pick type C1 fibroblasts and free cholesterol-enriched Chinese hamster ovary cells, J. Biol. Chem., 275 (2000) pp. 38104-38110). The resulting lysosomal accumulation of sphingomyelin (SM) appears to stabilize cholesterol in the LSOs, thereby exacerbating the cholesterol accumulation. To counteract this effect, this aspect of the invention is directed to at least partially restoring SMase activity in an effort to reduce cholesterol accumulation. In other embodiments, the foregoing SMase composition is combined with the cyclic oligosaccharide-polysaccharide composition described above as a pharmaceutical composition for lowering cholesterol in a mammal.

In another aspect, the invention is directed to a pharmaceutical composition that contains any of the above cholesterol-lowering compositions in a pharmaceutically acceptable vehicle (i.e., excipient). The pharmaceutical composition can also be formulated together with one or more medications that improves the overall efficacy of the pharmaceutical composition and/or reduces or avoid side effects.

The active ingredient(s) and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The phrase "pharmaceutically acceptable" refers herein to those compounds, materials, compositions, and/or dosage forms which are, within the scope of sound medical judgment, suitable for administration to a subject. The phrase "pharmaceutically acceptable excipient" as used herein refers to a pharmaceutically acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic composition for administration to the subject. Each excipient should be "acceptable" in the sense of being compatible with the other ingredients of the formulation and not injurious to the subject.

Some examples of materials which can serve as pharmaceutically acceptable excipients, particularly for liquid forms, include sugars (e.g., lactose, glucose and sucrose); starches (e.g., corn and potato starch); cellulose and its derivatives (e.g., sodium carboxymethyl cellulose, ethyl cellulose and cellulose acetate); gelatin; talc; waxes; oils (e.g., peanut oil, cottonseed oil, safflower oil, sesame oil, olive oil, corn oil and soybean oil); glycols (e.g., ethylene glycol, propylene glycol, and polyethylene glycol); polyols (e.g., glycerin, sorbitol, and mannitol); esters (e.g., ethyl oleate and ethyl laurate); agar, buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

Diluents increase the bulk of a solid pharmaceutical composition, and may make a pharmaceutical dosage form that is easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subject's stomach may be increased by the addition of a disintegrant to the composition. Disintegrants include alginic acid, carboxymethylcellulose calcium, carboxymethylcellulose sodium (e.g. Ac Di Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include, for example, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the modulator of bacterial adenyl cyclase and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methylcellulose, carbomer, cetostearyl alcohol and cetyl alcohol.

Liquid pharmaceutical compositions of the present invention may also contain a viscosity-enhancing agent to improve the mouthfeel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents, such as sorbitol, saccharin, sodium saccharin, sucrose, aspartame, fructose, mannitol and invert sugar, may be added to improve the taste. Flavoring agents and flavor enhancers may make the dosage form more palatable to the patient. Common flavoring agents and flavor enhancers for pharmaceutical products that may be included in the composition of the present invention include, for example, maltol, vanillin, ethyl vanillin, menthol, citric acid, fumaric acid, ethyl maltol and tartaric acid.

Preservatives and chelating agents, such as alcohol, sodium benzoate, butylated hydroxy toluene, butylated hydroxyanisole and ethylenediamine tetraacetic acid, may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting, except that they are not subjected to a final tableting step.

In another aspect, the invention is directed to methods for lowering a cholesterol level of a mammal by administering to the mammal a cholesterol-reducing composition described above. The mammal primarily considered herein is a human, although other mammals, such as dogs, cats, monkeys, cows, and others, can benefit as well.

In one embodiment, the composition is administered to the mammal in such a manner that the composition does not specifically target particular tissue or cells of the body. In the foregoing embodiment, the overall cholesterol level of the mammal is reduced. In another embodiment, the composition is administered to the mammal in such a manner that the composition selectively targets particular tissue or cells of the body. The composition can be made to selectively target particular tissue or cells within a mammal by, for example, administering the composition in a localized manner at the site of target tissue or cells (e.g., by injection into target tissue or cells). In an alternative embodiment, the composition can be made to selectively target particular tissue or cells within a mammal by administering the composition non-locally or locally, and including in the composition a selective targeting agent that selectively targets certain tissues or certain cells of the body (e.g., by employing an antibody targeting agent). The tissue being treated can be, for example, tissue of the liver, bone marrow, spleen, skin, lungs, nerves (particularly of the peripheral nervous system), and brain. The end result of the therapy is that the mammal experiences, either overall or in specific treated tissue, a reduced amount of cholesterol.

As described above, and depending on how the composition is formulated as well as the type of condition to be treated, the composition can be administered orally (e.g., by swallowing or enteral ingestion of tablets, capsules, powders, granules, pastes, solutions, suspensions, drenches, or syrups); parenterally, by, for example, subcutaneous, intramuscular or intravenous injection as; topically, by, for example, applying as a cream, ointment or spray to the skin, internal organs (e.g., lungs), or mucous membranes; or by applying as a pessary, cream or foam, or sublingually; ocularly, transdermally, or nasally.

In order to realize the therapeutic effect of a reduced cholesterol level, the cholesterol-lowering composition is administered in a therapeutically-effective amount. As is well known in the art, the dosage of the active ingredient(s) significantly depends on such factors as the extent of the lipid (e.g., cholesterol) accumulation, method of administration, size of the patient, and potential side effects. In different embodiments, depending on these and other factors, a suitable dosage of the active ingredient of the cholesterol-lowering composition may be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Further to the above embodiments, depending on the same and other factors, the composition is administered in the indicated amount by any suitable schedule, e.g., once, twice, or three times a day for a total treatment time of one, two, three, four, or five days, and up to, for example, one, two, three, or four weeks. Alternatively, or in addition, the composition is administered until a desired cholesterol level is reached. The desired cholesterol level can be any cholesterol level deemed by a professional in the medical arts to be appropriate to achieve.

The method described herein can be used to treat any condition expressing itself by an elevated level of a lipid in one or more tissues of a mammal. In one set of embodiments, the condition is a non-inherited form of hypercholesteremia caused primarily by environmental causes such as poor diet and/or other unhealthy lifestyle choices (e.g., lack of exercise and/or smoking). In another set of embodiments, the condition is inherited, as found in the lysosomal storage diseases (LSDs). The LSD being treated can be, for example, Niemann-Pick disease, Gaucher disease, GM1 gangliosidoses, GM2 gangliosidoses, Fabry disease, Krabbe disease, fucosidosis, metachromatic leukodystrophy (MLD), Wolman disease, Farber disease, or Schindler disease.

Examples have been set forth below for the purpose of illustration and to describe the best mode of the invention at the present time. However, the scope of this invention is not to be in any way limited by the examples set forth herein.

Furthermore, the complete disclosure of A. I. Rosenbaum, et al. *PNAS*, vol. 107, no. 12 (Mar. 23, 2010), pp. 5477-5482, including all exemplary information, discussion, and supporting information found therein, is herein incorporated by reference in its entirety.

Example 1

Synthesis of Cyclodextrin (CD) Polymers

General Description

The synthesis of the methyl β-cyclodextrin-PEG-dextran conjugate was designed to be fully modular such that any single piece can be modified without having to completely change the overall procedure. The PEG groups are incorporated onto the dextran polymer by amide formation between commercially available aminodextran and an appropriately protected amino-PEG-acid (e.g., BocHN-(PEG)$_n$-CO$_2$H). Removal of the N-protecting group then liberates an amine that can be coupled directly to methyl β-cyclodextrin via direct S$_N$2 displacement of the 1' tosyl group on 6$^A$-O-p-toluenesulfonyl-permethyl-β-cyclodextrin. If this final coupling is not run to completion, the remaining free amines can be used to conjugate a second molecule of interest (e.g., a fluorescent tag or a sugar).

Synthesis of Methyl-β-Cyclodextrin (MβCD or MβCD) Conjugate

Synthesis of mono(6A-O-p-toluenesulfonyl)-β-cyclodextrin (i.e., "tosylated β-cyclodextrin")

1.2 g of -β-Cyclodextrin was suspended in 10 mL H$_2$O, and 0.4 mL of NaOH aqueous solution (1.65 g in 5 mL H$_2$O) was added dropwise. After ~10 minutes, p-tosyl chloride was added gradually over about 10 minutes. Immediate precipitation was observed. The reaction was continued at ambient temperature (i.e., generally within 15-30° C.) for another two hours. The resulting solution was filtered, and the precipitate collected. The precipitate was dried under high vacuum in the presence of P$_2$O$_5$ overnight. The product at this stage is tosylated β-cyclodextrin.

Synthesis of mono(6A-O-p-toluenesulfonyl)permethyl-β-cyclodextrin (i.e., "Permethylated Tosylated β-Cyclodextrin" or "Tosyl-MβCD")

Tosylated β-cyclodextrin (0.8 g), produced as above, was dissolved in DMF and the resulting solution cooled to 0° C. After 10 minutes, 1.8 g of sodium hydride was added. The reaction mixture was stirred at the same temperature for one hour before it was warmed to ambient temperature and stirred for another hour. The mixture was then cooled to 0° C. Then 12.5 g of iodomethane was added. The reaction mixture was stirred at 0° C. for one hour, and then gradually warmed to ambient temperature. The resulting mixture was stirred for about 24 hours. After the reaction was complete, the mixture was poured into ice-water, and then extracted with CHCl$_3$. The organic layer was washed with sodium thiosulfate, water, and brine, sequentially. The volatiles were removed in vacuo and the crude product purified with 0.1-1% of methanol in ethyl acetate.

Synthesis of Boc-NH-(PEG)$_3$-CONH-aminodextran

Separately, 500 mg of aminodextran (MW of 70,000) was suspended in 10.0 mL DMF. The aminodextran used generally contains a multiplicity of amine groups. After 5 minutes, 0.4 mL (5 mmol) of pyridine was added and the mixture stirred at ambient temperature for 10 minutes. At that point, ca. 510 mg (1.4 mmol) of Boc-NH-(PEG)$_3$-COOH and ca. 540 mg of 1-ethyl-3-(3-dimethylaminopropyl) carbodiimide (EDC) were sequentially added. The resulting mixture was vigorously stirred at ambient temperature overnight (i.e., ca. 18 hours) and then purified by extensive dialysis against water (Spectra/Por tubing, MW cutoff of 12-14 kDa) to remove unreacted small molecules. Finally, the product was twice lyophilized to furnish the PEGylated aminodextran as a white powder (ca. 600 mg). If storage was necessary, the product was stored in a refrigerator at −20° C.

Synthesis of NH$_2$-(PEG)$_3$-CONH-aminodextran

Boc-NH-(PEG)$_3$-CONH-dextran (ca. 600 mg), produced as above, was added to a flask containing 15 mL of trifluoroacetic acid (TFA) at 0° C., and the mixture stirred for 30 minutes, at which time the mixture was gradually warmed to ambient temperature and stirred for an additional 45 minutes. The resulting crude product was diluted with water and purified by dialysis (e.g., three times) against water. After lyophilization (3×), the product was obtained as a white powder (ca. 600 mg).

Synthesis of
MβCD-NH-(PEG)$_3$-CONH-aminodextran

NH$_2$-(PEG)$_3$-CONH-dextran (ca. 600 mg), produced as described above, was dissolved in 45 mL of formamide. To this solution was added 560 mg (0.4 mmol) of permethylated tosylated β-cyclodextrin, prepared as above. The reaction mixture was heated to 100° C. and stirred for 48 hours. Completion of the reaction was confirmed by TLC. The reaction mixture was then diluted with water and extensively dialyzed against water. After lyophilization (twice), the product was obtained as a white powder (530 mg). The product was stored in a −20° C. refrigerator and could be used without further purification.

Synthesis of AlexaFluor546-MβCD-NH-(PEG)$_3$-CONH-aminodextran

MβCD-NH-(PEG)$_3$-CONH-aminodextran (ca. 530 mg) was added to a minimal amount of phosphate-buffered saline (PBS) solution, and the mixture stirred at ambient temperature for 1 hour. At that point, AlexaFluor546 NHS ester (0.4 mg, 0.37 pmol) was added. The reaction mixture was stirred at ambient temperature for an additional 48 hours. After extensive dialysis against water, and lyophilization (3×), a pink cotton-like solid product was obtained (427 mg). The final product was stored in a −20° C. refrigerator before used in a cell assay.

The synthesis described herein easily allows for the incorporation of other adducts, such as mannose-6-phosphate (M6P). The synthesis described herein also allows for variation, modification, or optimization of the size of the dextran, the size of the PEG linker to the MβCD, and the degree of substitution with both M6P and MβCD, all of which have an impact on the efficacy of the composition. Furthermore, the density of M6P affects the avidity of binding by altering the effective valency of the ligand-receptor interaction. Since two MβCDs are presumably required to solubilize a cholesterol molecule, the density of MβCD is important (i.e., high density of MβCD promotes cholesterol binding).

Example 2

Use of Cyclodextrins to Reduce Cholesterol

The efficacy of various MβCD-polymers (and other adducts or modifications of MβCD) in human NPC fibroblasts was tested. The two cell lines tested herein are two NPC1 lines and one or two NPC2 lines. The time and concentration dependence of the effects on cholesterol accumulation in the LSOs were tested. For the most effective polymers, a determination was made on how long they are retained in cells. In order to quantify cellular uptake and retention of the polymers, the initial test polymers also included fluorophores. The retention ability was found by measuring the loss of fluorescence of the polymers when incubated without polymer in the surrounding medium. In parallel, a determination was made on how long the reduction of cholesterol accumulation persists after removal of the polymer from the growth medium.

Figure 1:
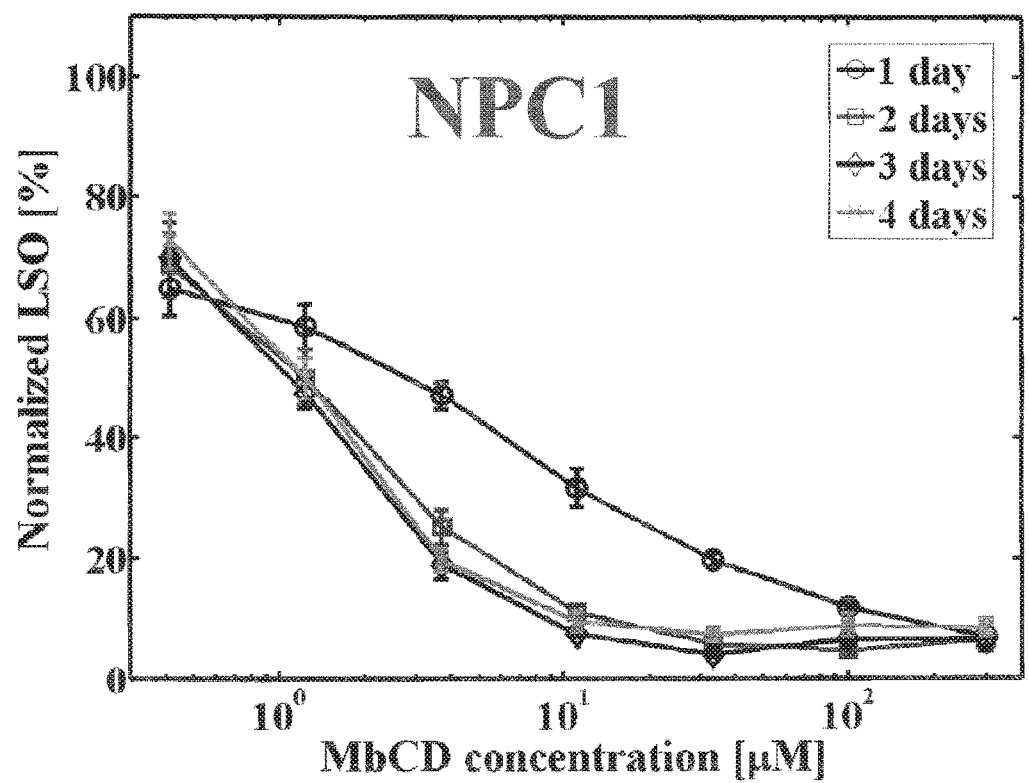
FIG. 1. Graph showing the concentration and time dependence of the removal of cholesterol from LSOs of human NPC1 cells incubated with the indicated concentrations of MβCD in complete medium for 1-4 days. Similar results were obtained with NPC2 cells.
Figure 2:
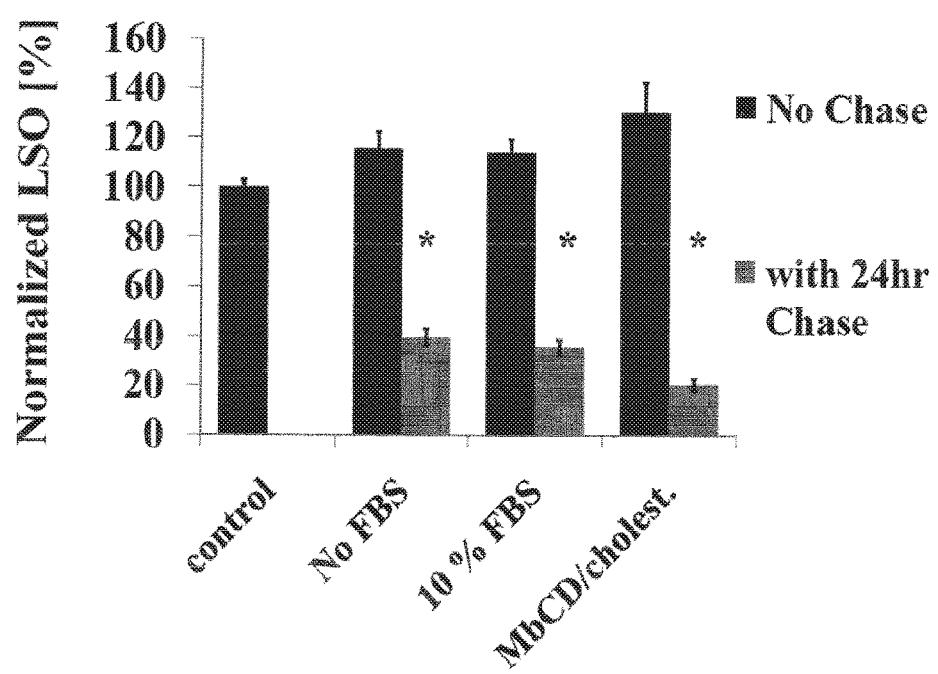
FIG. 2. Graph showing concentration of cholesterol from LSOs of NPC1 cells incubated with 0.33 mM MβCD for one hour under various conditions (i.e., no FBS, 10% FBS, and cholesterol-loaded MβCD (i.e., "MbCD/cholest."), and these with either no chase or a 24 hour chase). At the end of the incubation, cells were rinsed thoroughly, and returned to complete medium for 24 hours. Although a one-hour incubation with cholesterol-loaded MβCD increased the cholesterol in LSOs, by 24 hours the LSO cholesterol in these cells was greatly reduced, even with negligible amounts of extracellular MβCD. Similar results were obtained with NPC2 cells.

In this experiment, studies were conducted to determine the effects of MβCD on NPC1 and NPC2 cells. FIG. 1 shows the concentration and time dependence of the removal of cholesterol from LSOs as assayed by a previously described method based on filipin staining and digital image analysis (N. H. Pipalia, et al., *J. Lipid Res.*, 47 (2006) pp. 284-301, and Rosenbaum A. I., et al. *Biochim. Biophys. Acta.*, 1791 (2009), pp. 1155-1165). From FIG. 1, it can be seen that the effect reaches steady state in about 2 days, and 2-3 µM gives a half-maximal effect. Significantly, hydroxypropyl-βCD (i.e., "HPβCD"), a CD derivative that has previously been used in animal studies, required about 3-5 times higher concentrations to achieve the same effect. To distinguish between effects of extracellular MβCD and endocytosed MβCD, a brief (1 hour) incubation was conducted with a high concentration of MβCD (0.33 mM) to allow pinocytic uptake, which is well known to deliver soluble polar molecules to late endosomes and lysosomes (S. Mukhejee, et al., *Physiol. Rev.*, 77 (1997) pp. 759-803). The cells were then rinsed and incubated in complete medium for 24 hours. During the chase, there was a significant reduction in the cholesterol in LSOs, even with virtually no extracellular MβCD (FIG. 2). To further emphasize this, the one-hour loading pulse was conducted with cholesterol-loaded MβCD, which would actually increase the cellular cholesterol during the loading period. Nevertheless, there was a very significant loss of cholesterol from the LSOs during the subsequent 24 hr chase. These data provide strong evidence that endocytosed MβCD can fully account for the effects of MβCD. Similar effects were seen on NPC2 cells (not shown).

Figure 3:
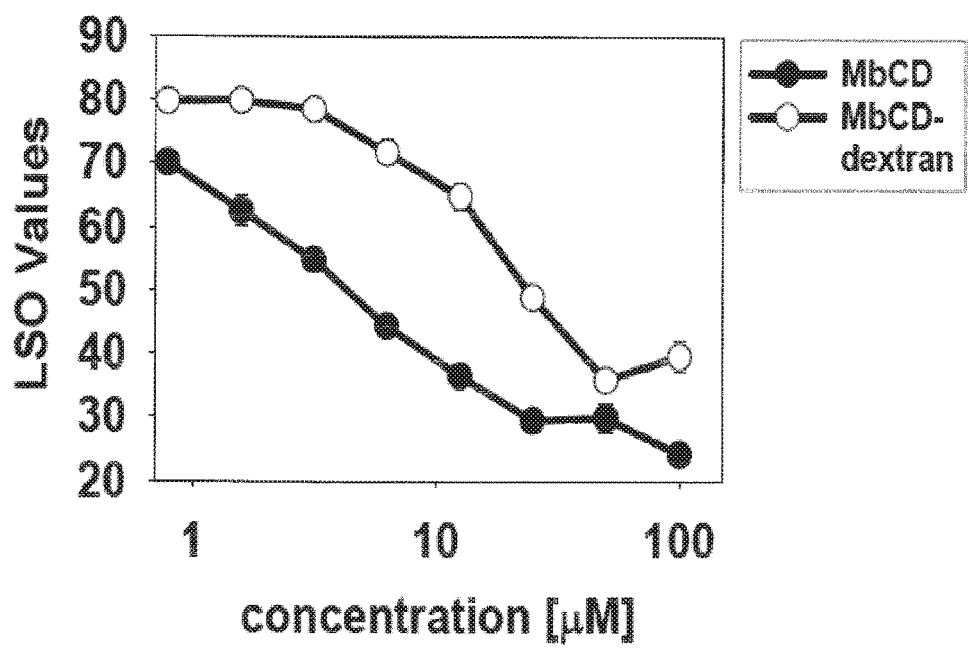
FIG. 3. Graph comparing the cholesterol-lowering ability of MβCD and a MβCD-dextran composition of the instant invention. Human NPC1 cells were incubated with MβCD (●) or Dextran-PEG-MbCD (O) for 39 hours. The polymers had about two MβCDs per polymer, and the concentration is the MβCD concentration. Since two MβCD molecules are required to solubilize a cholesterol, it is likely that higher degrees of substitution would be more effective, but even these first polymers show a significant effect.

Next, to test the idea of creating lysosomally targeted MβCD, dextran polymer conjugates with a MβCD at the end of 15 atom polyethylene glycol (PEG) spacers were prepared. The original syntheses incorporated about two MβCD per 70 KDa dextran chain; however, the number of MβCD can be significantly increased, if desired. Even with this low degree of substitution, the polymers were effective at lowering cholesterol in the LSOs (FIG. 3). Dextrans are delivered to late endosomes/lysosomes by fluid phase endocytosis (S. Mukherjee, et al., *Physiol. Rev.*, 77 (1997) pp. 759-803).

Figure 4:
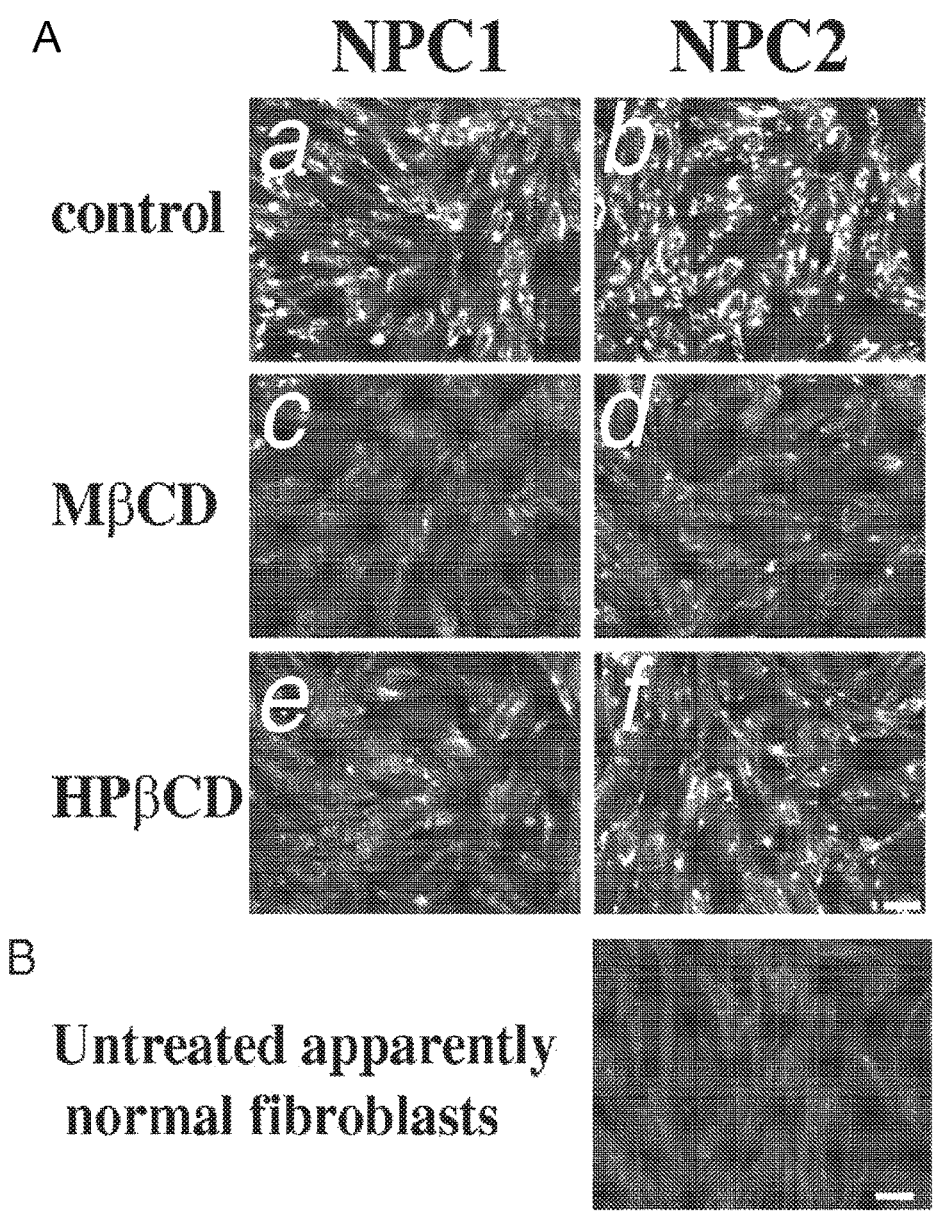
FIG. 4. Micrographs showing the effect of CDs on cholesterol accumulation in NPC1- and NPC2-deficient cells. (A) Background and shading corrected images of untreated (a and b), MβCD-treated (c and d), or HPβCD-treated (e and f) GM03123 NPC1 cells (a, c, and e) or GM18455 NPC2 (b, d, and f) mutant cells. NPC mutant cells were treated with 300 μMCD for 1 day. (B) Untreated, apparently normal GM05659 cells, shown for comparison. (Scale bars, 100 μm.)
Figure 5A:
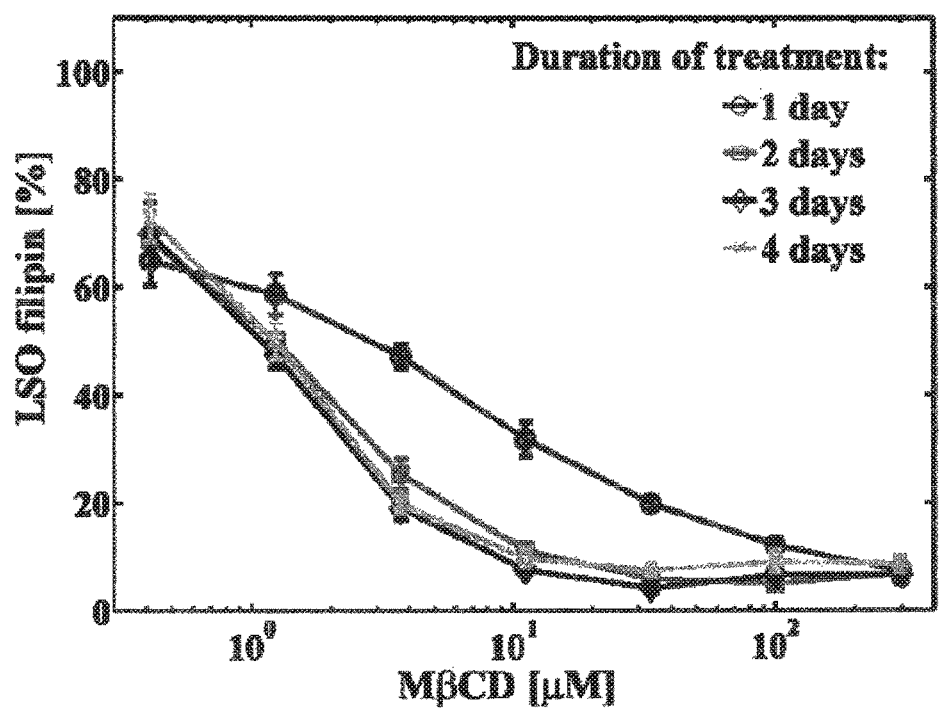
FIGS. 5 A-D. Charts showing quantification of CD effects on cholesterol accumulation in NPC1 and NPC2 mutant cells. The filipin fluorescence in LSOs was measured in NPC1 (A and B) and NPC2 (C and D) mutant cells treated with either MβCD (A and C) or HPβCD (B and D) for 1-4 days. Data are presented as percentage of the average value for untreated controls in two independent experiments±SEM (n=6 for treated samples, n=40 for control, where n is total number of wells per condition used for quantification).
Figure 5B:
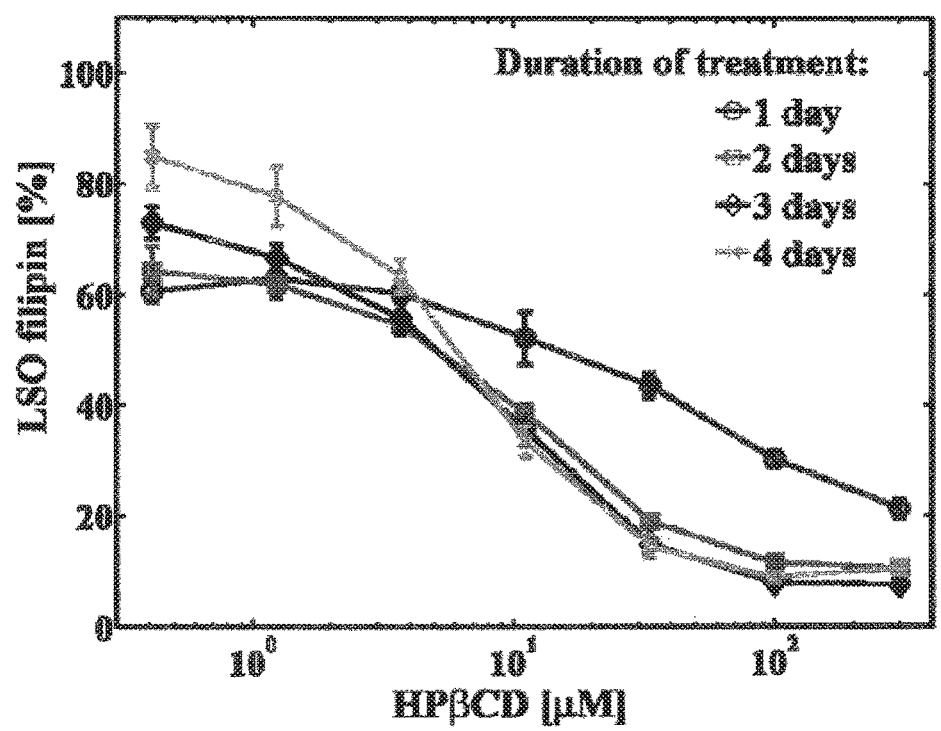
Figure 5C:
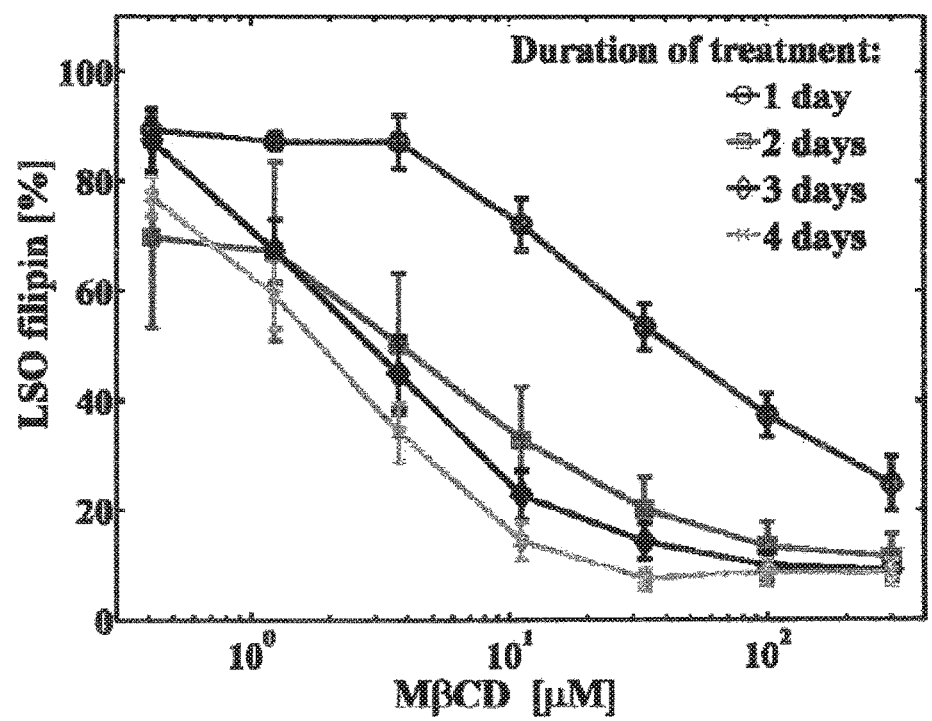
Figure 5D:
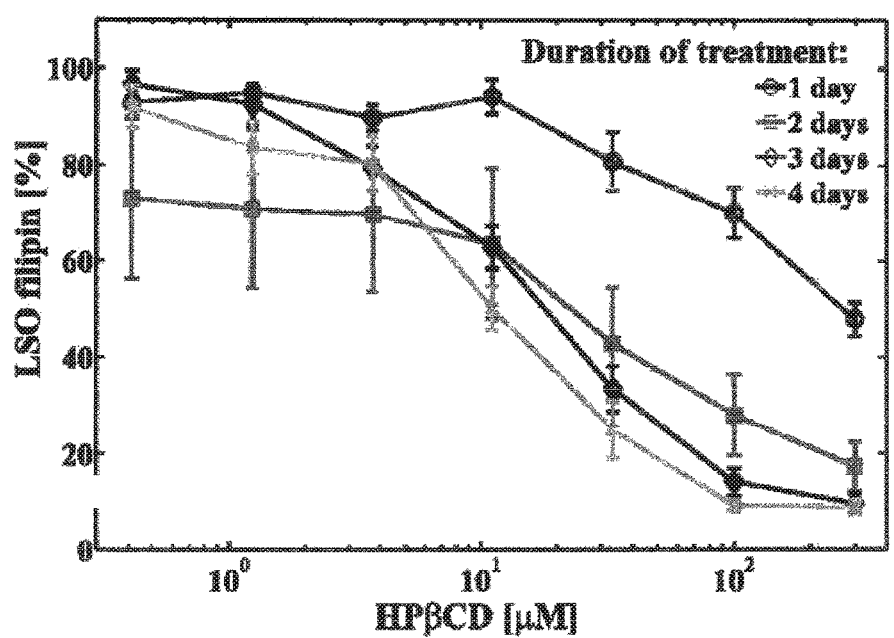
Figure 6:
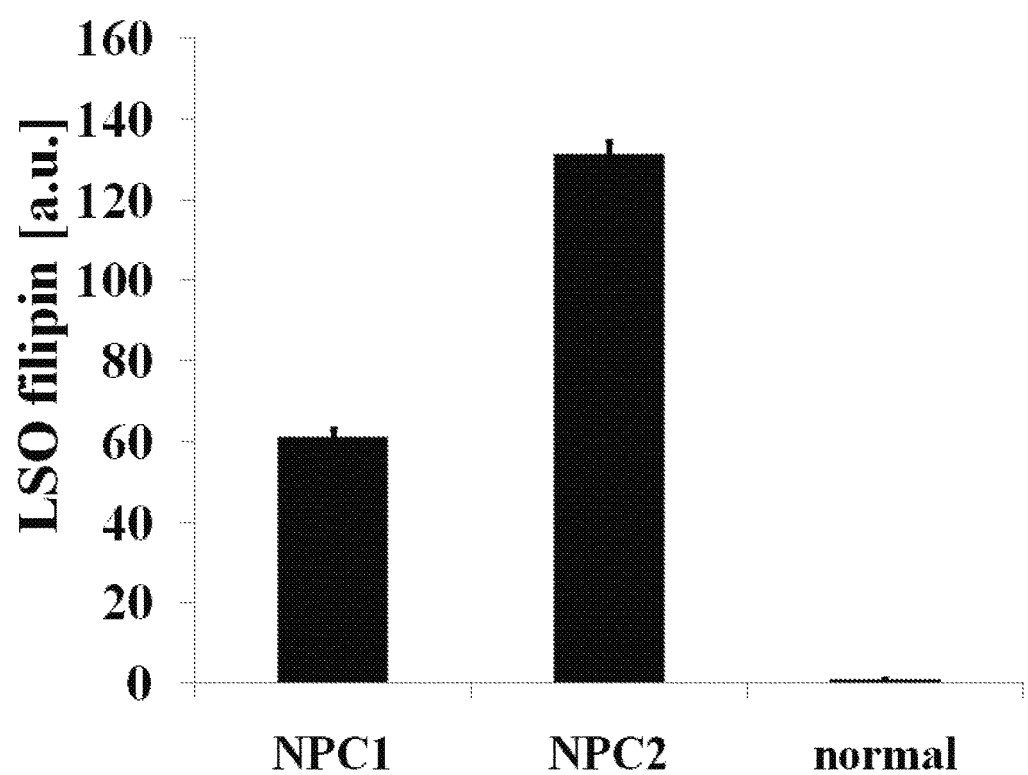
FIG. 6. Chart comparing cholesterol accumulation as measured by the LSO assay in NPC1-defective, NPC2-defective, and apparently normal human fibroblasts. Cells were plated in 384-well assay plates at a density to produce ≈80-90% confluency after 4 days. At the end of the experiment, cells were fixed with 1% PFA and stained with 50 µg/mL filipin. Images were acquired using an ImageXpress MICRO imaging system with a 10× objective. Quantification of filipin labeling of the LSOs was performed as described previously (Pipalia N H, Huang A, Ralph H, Rujoi M, Maxfield FR (2006) Automated microscopy screening for compounds that partially revert cholesterol accumulation in Niemann-Pick C cells. *J. Lipid Res.* 47:284-301). Data represent averages±SEM of one representative experiment (11≤n≤16, where n is total number of wells per condition used for quantification).
Figure 7A:
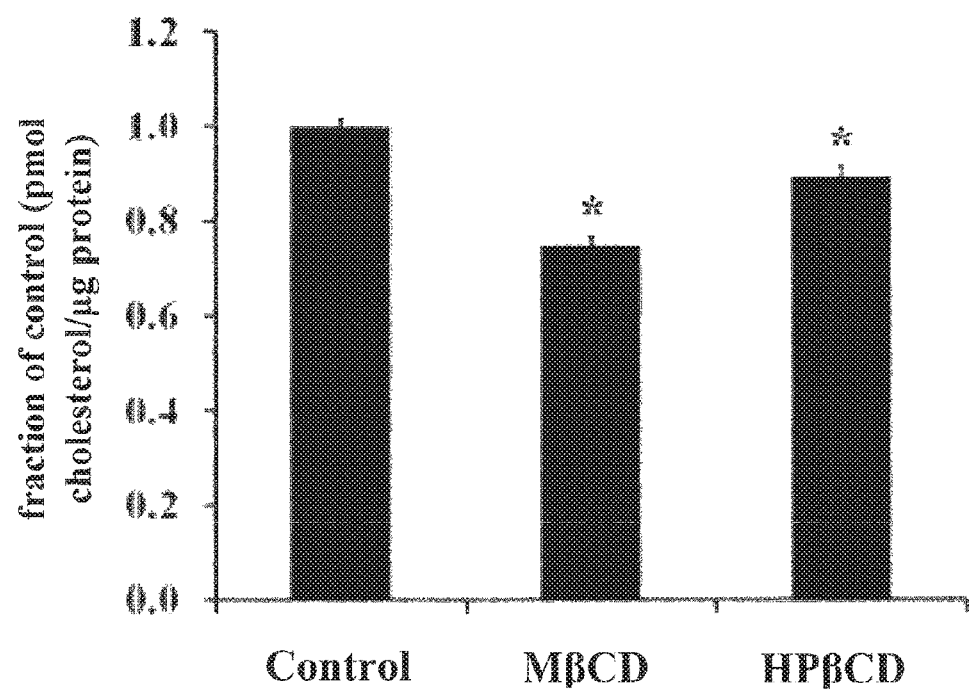
FIGS. 7 A-D. Charts showing GC/MS measurement of cyclodextrin effects on total free cholesterol levels in NPC1-deficient, NPC2-deficient, apparently normal, and U18666A-treated normal cells. Cells were plated in six-well plates at a density to produce ≈80-90% confluency by experiment completion. Cells were treated with 0.9 mM MβCD or HPβCD for 1 day in growth medium. At the end of the experiment, cellular lipids were extracted and analyzed by GC/MS. Data represent averages±SEM of two independent experiments normalized to control average value for each experiment. Control average values were as follows: 0.070±0.011 pmol free cholesterol per µg cell protein for NPC1 mutant cells (A), 0.133±0.005 pmol/µg for NPC2 mutant cells (B), 0.044±0.003 pmol/µg for normal cells (C), and 0.074±0.006 pmol/µg for normal cells treated with 1 µM U18666A (D). *$P<0.01$ vs. control (6≤n≤9, where n is total number of wells per condition used for quantification).
Figure 7B:
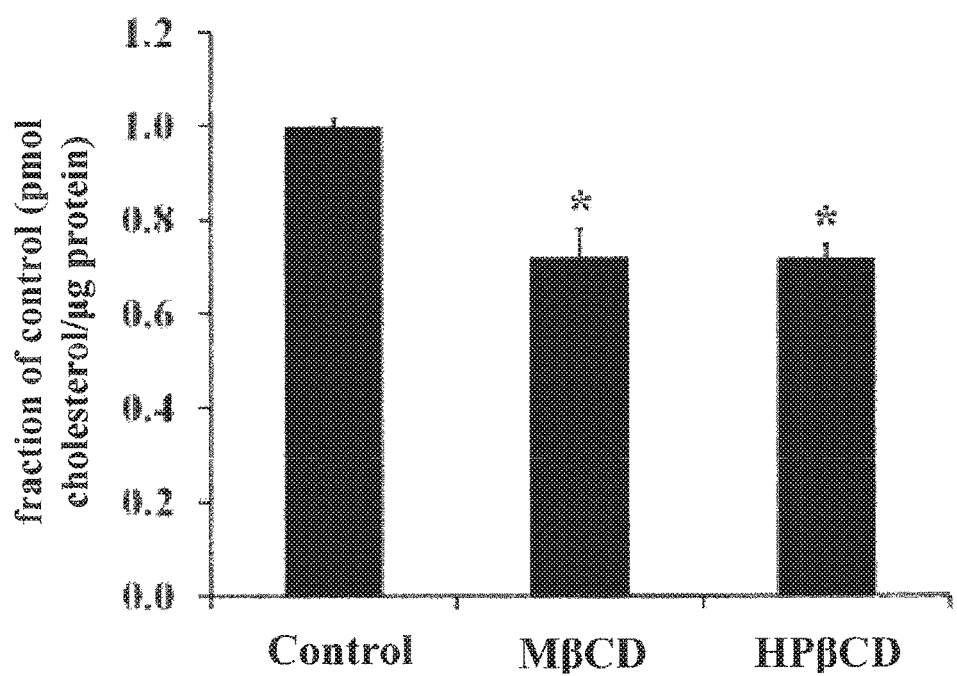
Figure 7C:
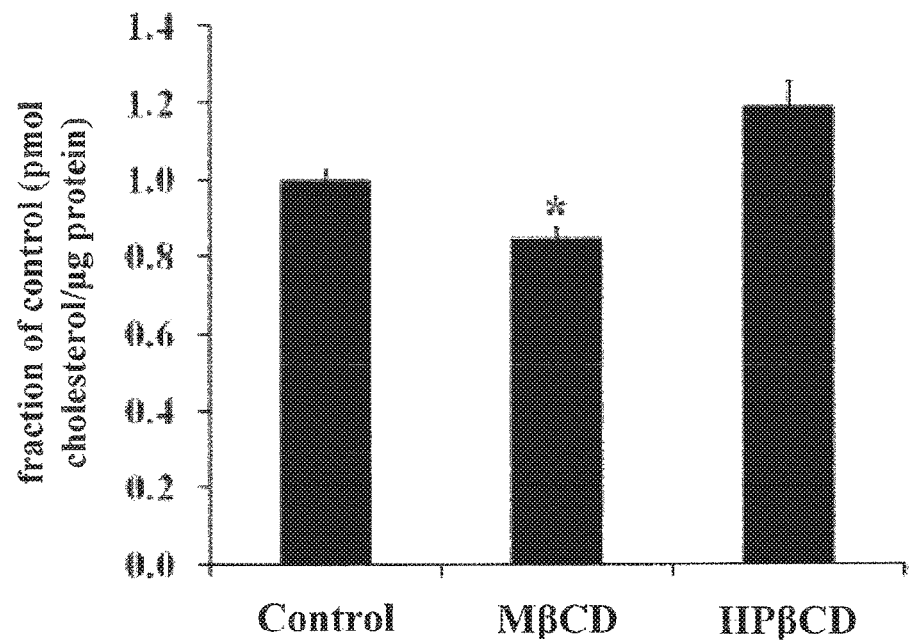
Figure 7D:
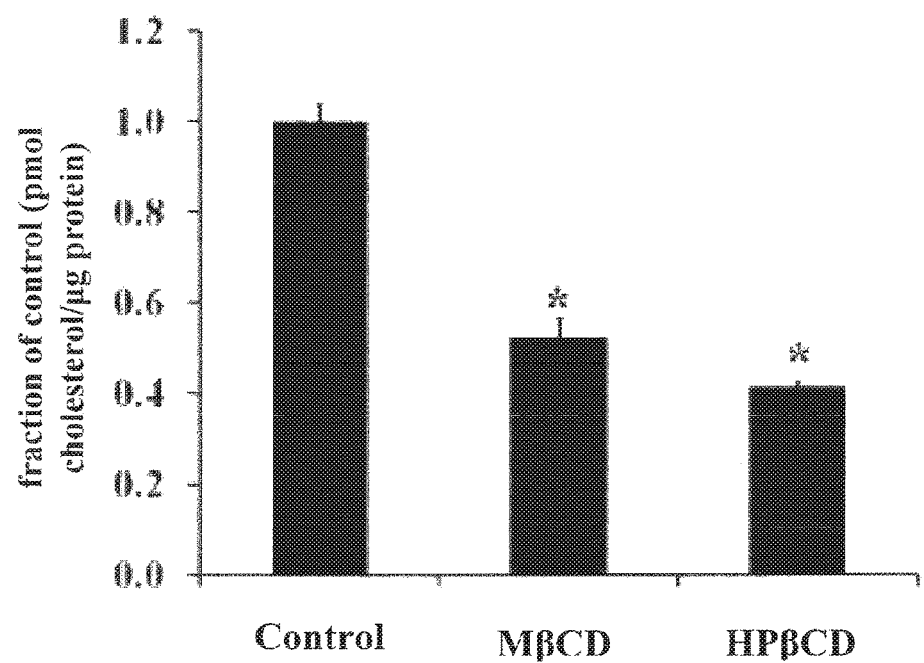
Figure 8A:
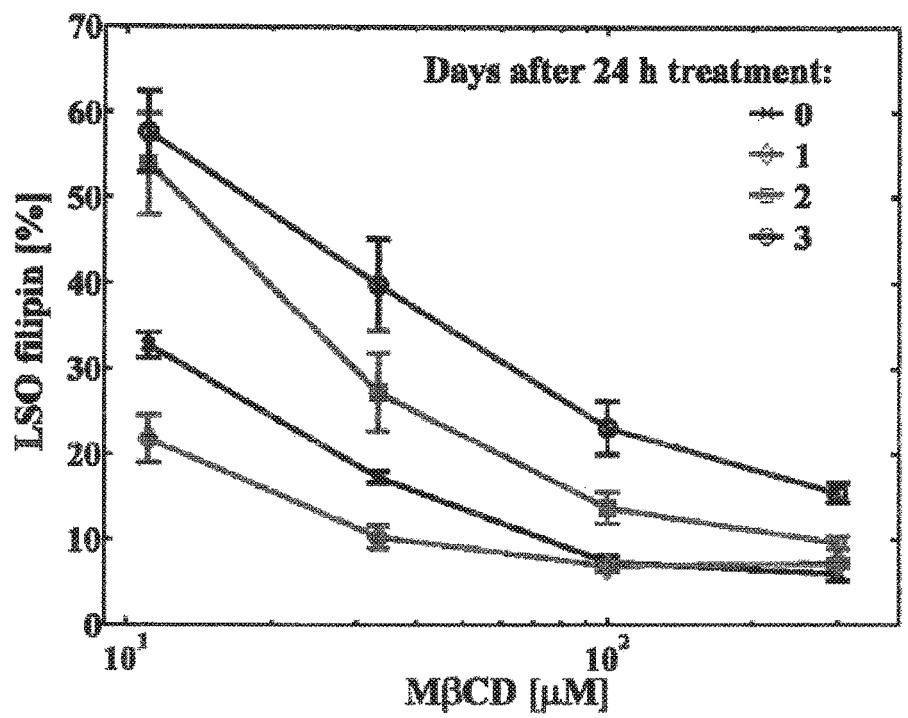
FIGS. 8 A-D. Charts showing persistence of CD effects after treatment. NPC1 (A and B) and NPC2 (C and D) treated with various concentrations of MβCD (A and C) and HPβCD (B and D) for 1 day and then fixed (0 days after 24 h treatment), or rinsed extensively, and allowed to grow in normal growth medium for up to three additional days after CD removal. Quantification of LSO filipin fluorescence power is shown. Data are presented as percentage of the average value for untreated controls in two independent experiments±SEM (n=6 for treated samples, n=24 for control, where n is total number of wells per condition used for quantification).
Figure 8B:
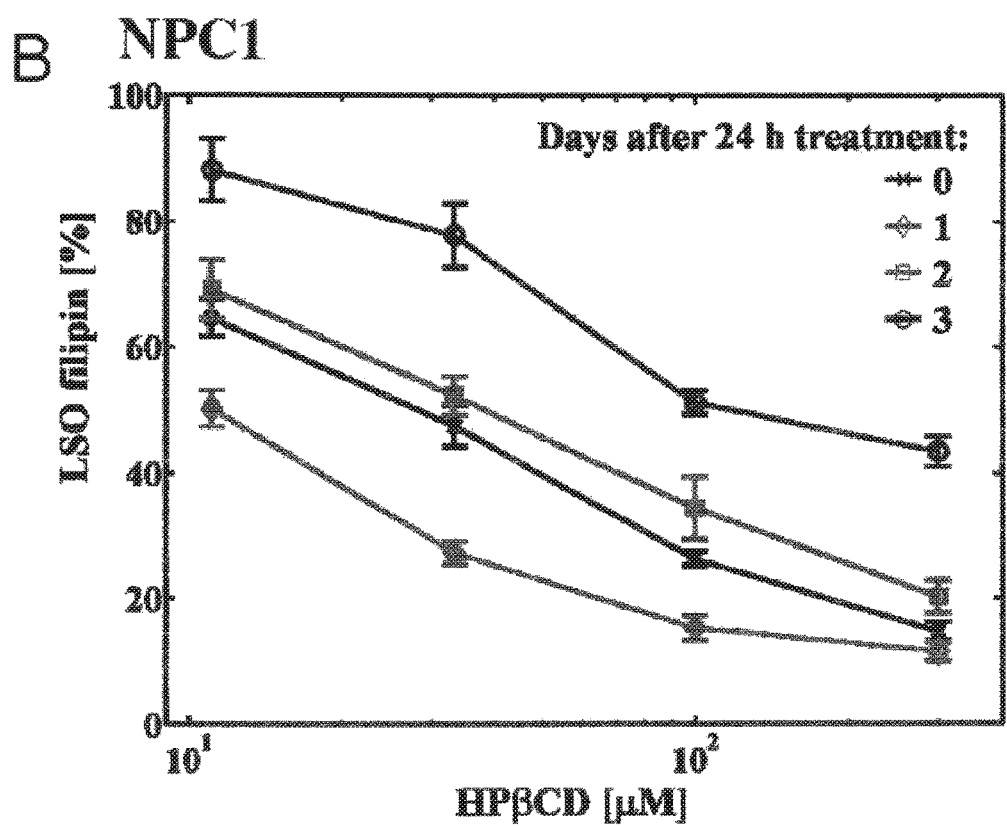
Figure 8C:
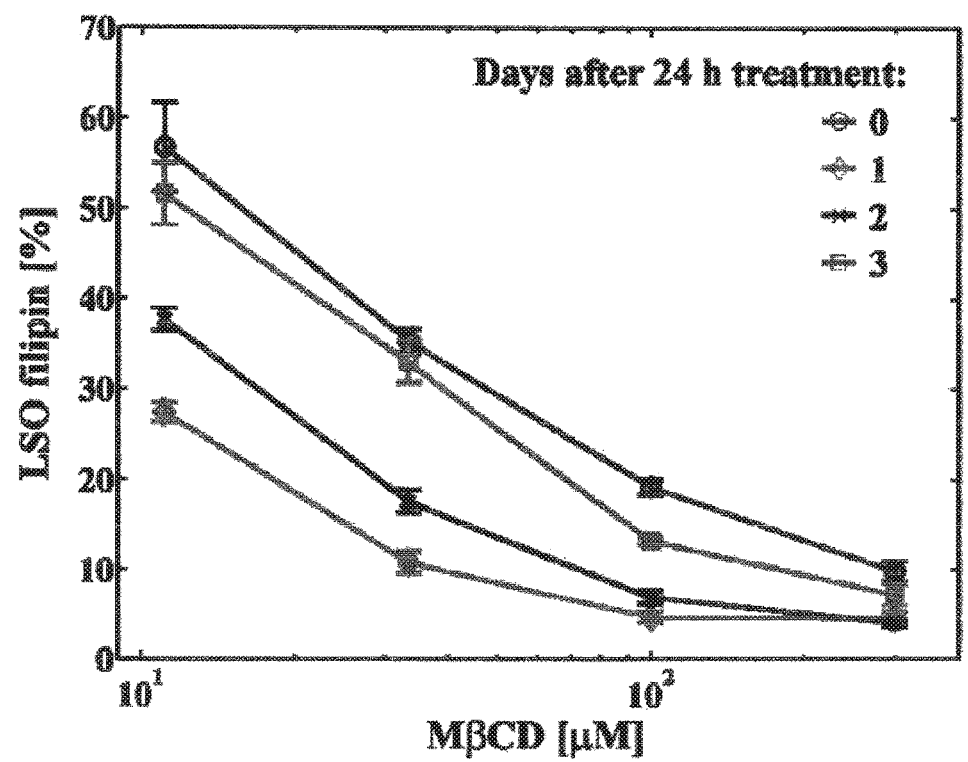
Figure 8D:
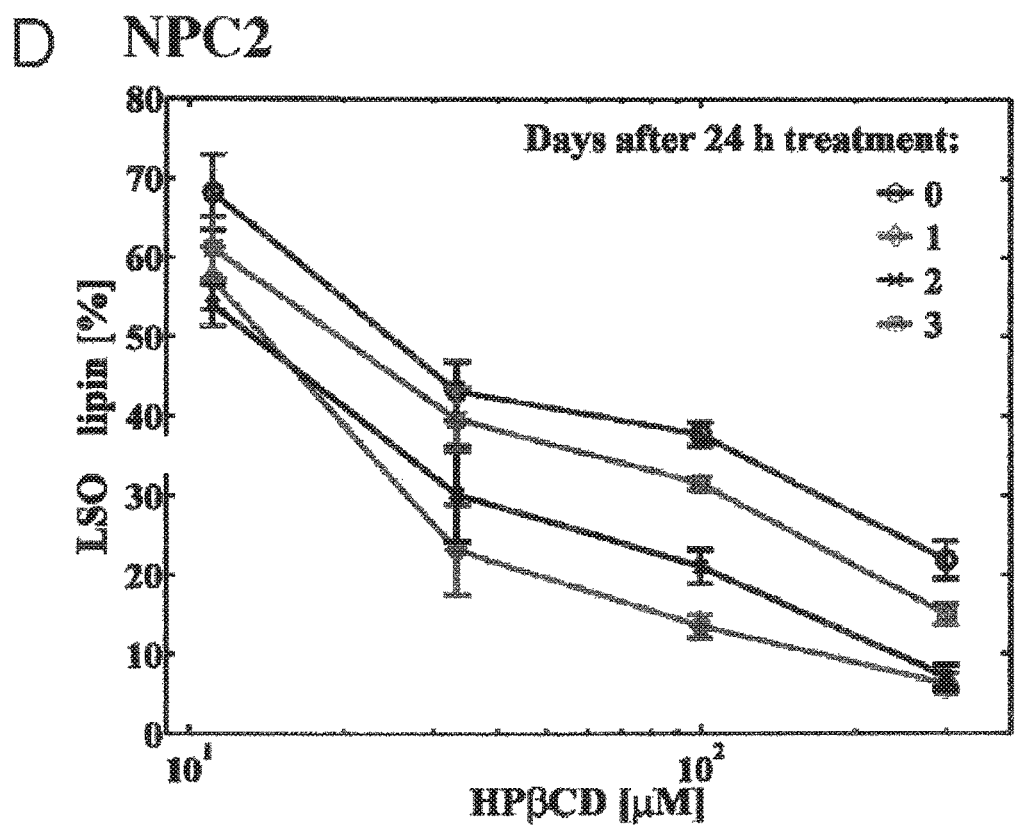

Further studies showed that treatment with either MβCD or HPβCD reduced cholesterol accumulation, as detected by filipin labeling (FIG. 4). The CD effects on LSO cholesterol accumulation in NPC1 and NPC2 mutant cells were found to be dose and time dependent (FIG. 5). As shown, both MβCD and HPβCD can reduce cholesterol accumulation in LSOs of NPC1 and NPC2 fibroblasts to near-normal levels using low micromolar concentrations. A comparison of LSO values for untreated NPC1, NPC2, and apparently normal cells is shown in FIG. 6. Most of the decrease in LSO cholesterol occurred during the first two days of incubation. MβCD is more potent than HPβCD in eliciting this reduction (see Table 1 below). This finding correlates well with previous studies, which showed that MβCD is more potent than HPβCD at extracting cholesterol from biological membranes. As shown by FIG. 7, studies employing gas chromatography and mass spectrometry further demonstrate that overall cholesterol levels were reduced significantly upon CD treatment.

TABLE 1

Apparent EC$_{50}$ values for MβCD and HPβCD
effects on LSO values of GM03123 and GM18445 cells
as function of time of incubation with the compounds.

| Cell line | Compound | Days of treatment | EC$_{50}$ (μM) | $R^2$ |
|---|---|---|---|---|
| GM03123 | MβCD | 1 | 2.22 | 0.943 |
| GM03123 | MβCD | 2 | 1.10 | 0.997 |
| GM03123 | MβCD | 3 | 0.98 | 0.995 |
| GM03123 | MβCD | 4 | 1.08 | 0.993 |
| GM18455 | MβCD | 1 | 40.39 | 0.987 |
| GM18455 | MβCD | 2 | 3.19 | 0.965 |
| GM18455 | MβCD | 3 | 2.80 | 0.999 |
| GM18455 | MβCD | 4 | 1.69 | 0.997 |
| GM03123 | HPβCD | 1 | 3.16 | 0.781 |
| GM03123 | HPβCD | 2 | 3.77 | 0.920 |
| GM03123 | HPβCD | 3 | 4.18 | 0.966 |
| GM03123 | HPβCD | 4 | 5.44 | 0.991 |
| GM18455 | HPβCD | 1 | 272.41 | 0.970 |
| GM18455 | HPβCD | 2 | 20.84 | 0.909 |
| GM18455 | HPβCD | 3 | 16.94 | 0.998 |
| GM18455 | HPβCD | 4 | 11.51 | 0.991 |

Apparent EC$_{50}$s (compound concentration at 50% reduction in LSO filipin) for MβCD and HPβCD treatment of GM03123 (NPC1) and GM18455 (NPC2) cells for 1-4 days were determined by fitting (using MATLAB, nonlinear least-squares Levenberg-Marquardt algorithm) dose-response curves (FIG. 5) to the rectangular hyperbola of the form y = m/(x + b) + c, and solving for y = 50, where y = normalized LSO filipin values (%), x = compound concentration (μM), and m, b, and c are coefficients.

Example 3

Effects of β-CDs After Treatment: Withdrawal Studies

To determine whether the CD-mediated decrease in cholesterol accumulation would be sustained after the compound has been removed from the culture medium, NPC1 and NPC2 mutant cells were treated for 1 day with varying concentrations of MβCD or HPβCD (FIG. 8). The cells were then washed extensively to remove the compounds and returned to growth medium for up to three days. Cells that were allowed to grow for one more day after treatment with CD had a further decrease in LSO values when compared with cells that were treated for the same length of time but fixed immediately after treatment. After two and three days after treatment, cholesterol accumulation in LSOs of both NPC1 and NPC2 mutant cells started to increase, but there was still a significant reduction in the LSO cholesterol accumulation even after three days in serum containing medium in the absence of extracellular CD.

The delayed nature of CD effects (i.e., a further decrease in cholesterol accumulation after CD is removed from the medium) provided an initial indication that CD is acting to transfer cholesterol within the LSOs, as opposed to eliciting net efflux from LSOs by lowering cholesterol levels in the PM.

Example 4

Acute MβCD Treatments of NPC-Defective Cells

To determine whether the reduction of free cholesterol in LSOs of NPC-defective cells resulted from extraction of cholesterol by CD from the PM or from inside the LSOs, this experiment acutely treated cells for one hour with MβCD in medium without serum (to extract cholesterol from the PM), MβCD in medium plus 10% FBS (to exchange cholesterol between serum lipoproteins and the PM (V. M. Atger, et al. (1997), *J. Clin. Invest.*, 99:773-780)), or MβCD loaded with cholesterol (≈5:1 (MβCD/cholesterol) ratio) to overload cells with cholesterol.

Figure 9A:
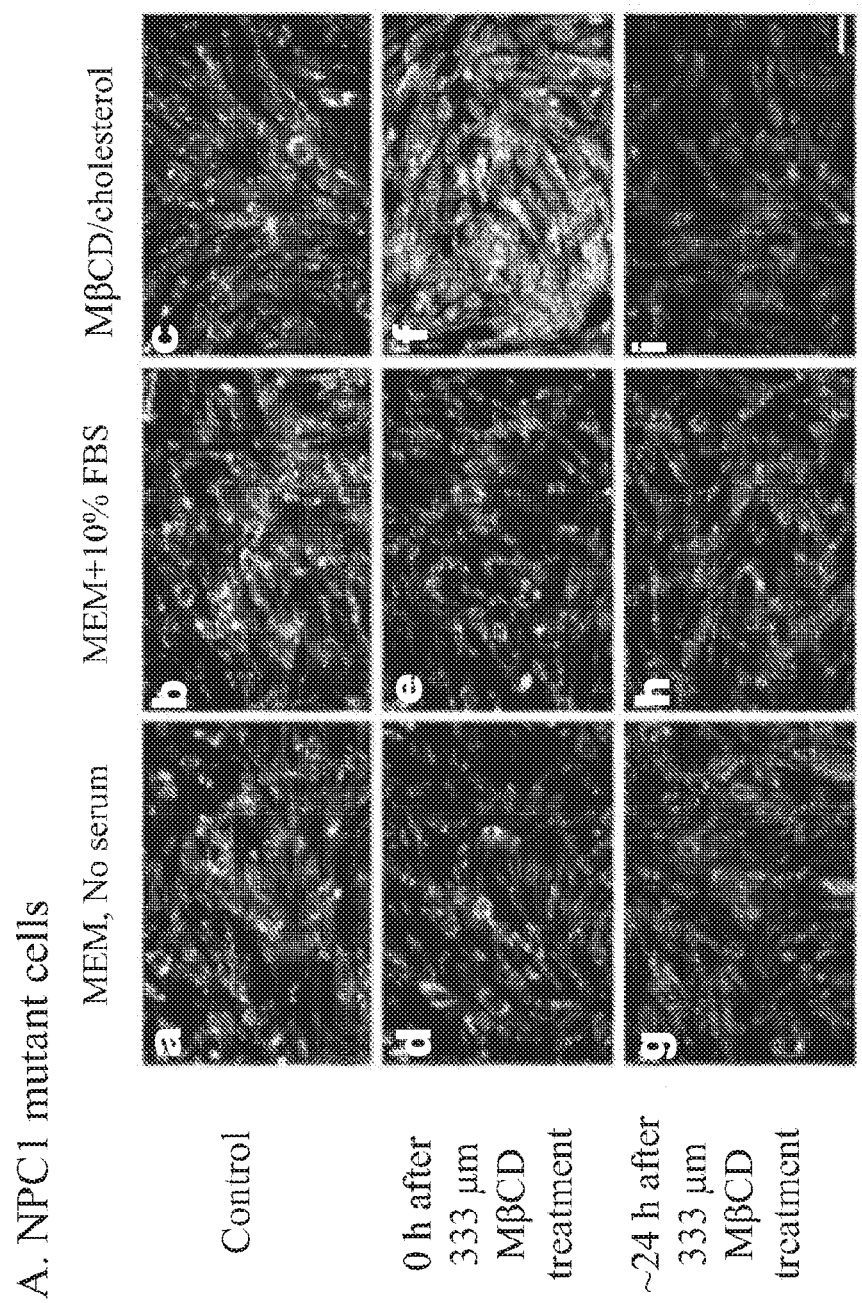
FIG. 9 A, B. Filipin micrographs showing acute cyclodextrin effects on cholesterol accumulation in NPC1- and NPC2-deficient cells. Background and shading corrected images of untreated control (panels a-c), 0 h after treatment (panels d-f), or 24 h after treatment (panels g-i) for NPC1 (A) or NPC2 (B) mutant cells were obtained as in FIG. 6. Cells were treated either with 333 µM MβCD dissolved in MEM with no serum (panels a, d, and g), in MEM with 10% FBS (panels b, e, and h), or with 333 µM MβCD loaded with cholesterol (panels c, f, and i). (Scale bars, 100 µm.)
Figure 9B:
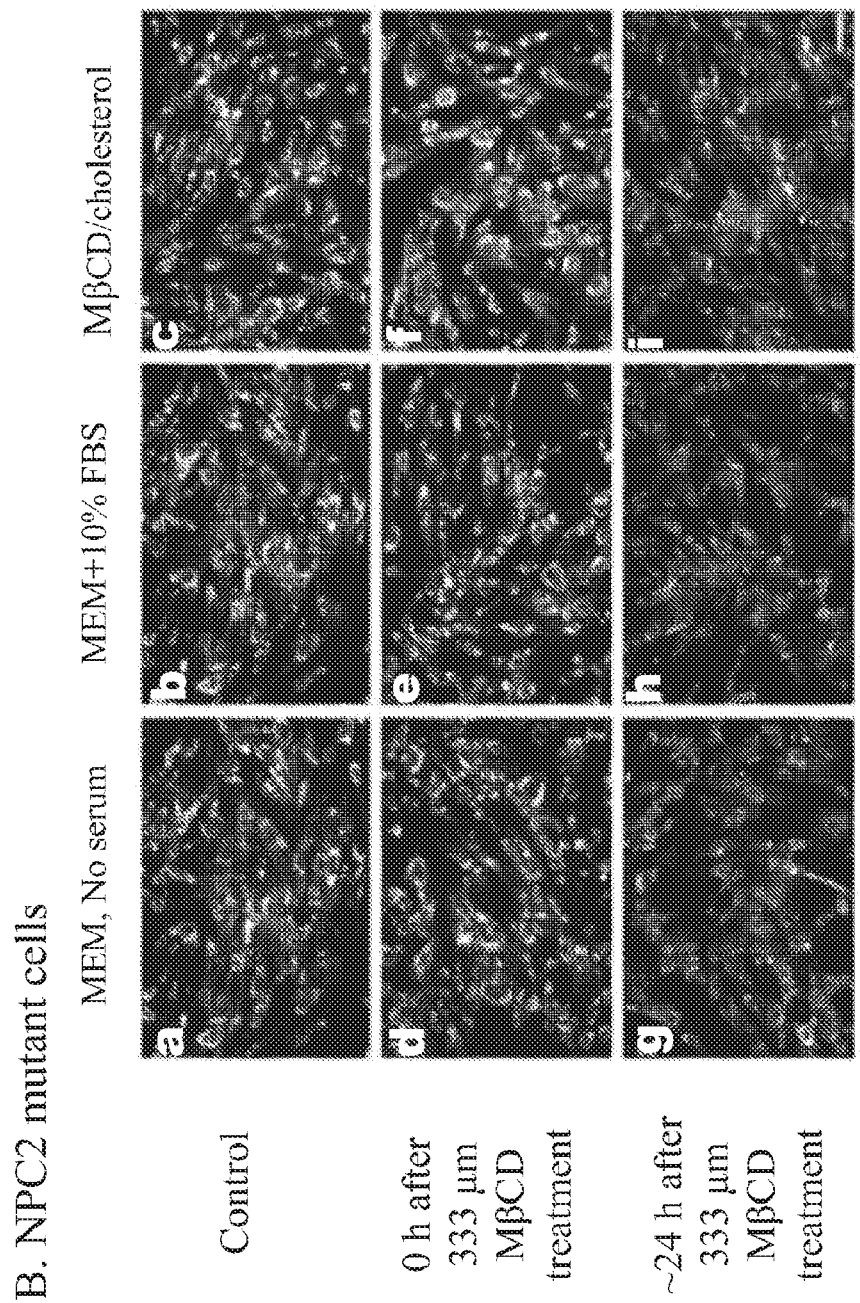
Figure 10A:
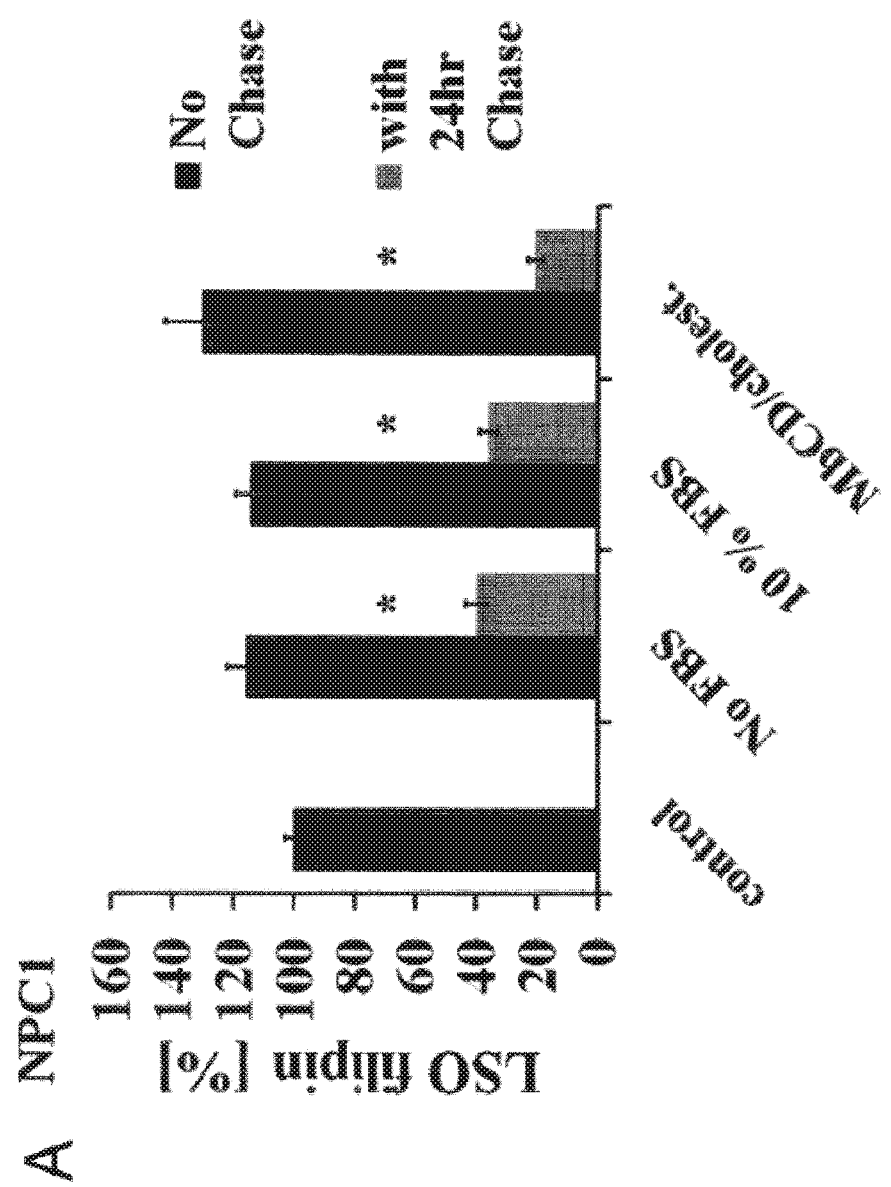
FIGS. 10 A-D. Short-term MβCD treatment. NPC1 (A and B) and NPC2 (C and D) mutant cells were treated for 1 hour with 333 µM MβCD in growth media without serum, 333 µM MβCD in media plus 10% FBS, or 333 µM MβCD loaded with cholesterol (5:1 (MβCD/cholesterol) ratio). Cells were either fixed immediately or rinsed extensively and returned to growth medium for 24 hours. Quantification of LSO filipin fluorescence power is shown (A and C). Numeric data represent averages±SEM of three independent experiments normalized to control (untreated) average value for each experiment. *$P<0.0001$ vs. control (n=12, where n is total number of wells used for quantification). Filipin images of NPC1 (B) or NPC2 (D) mutant cells treated with MβCD/cholesterol are shown. (Scale bars, 100 µm.)
Figure 10C:
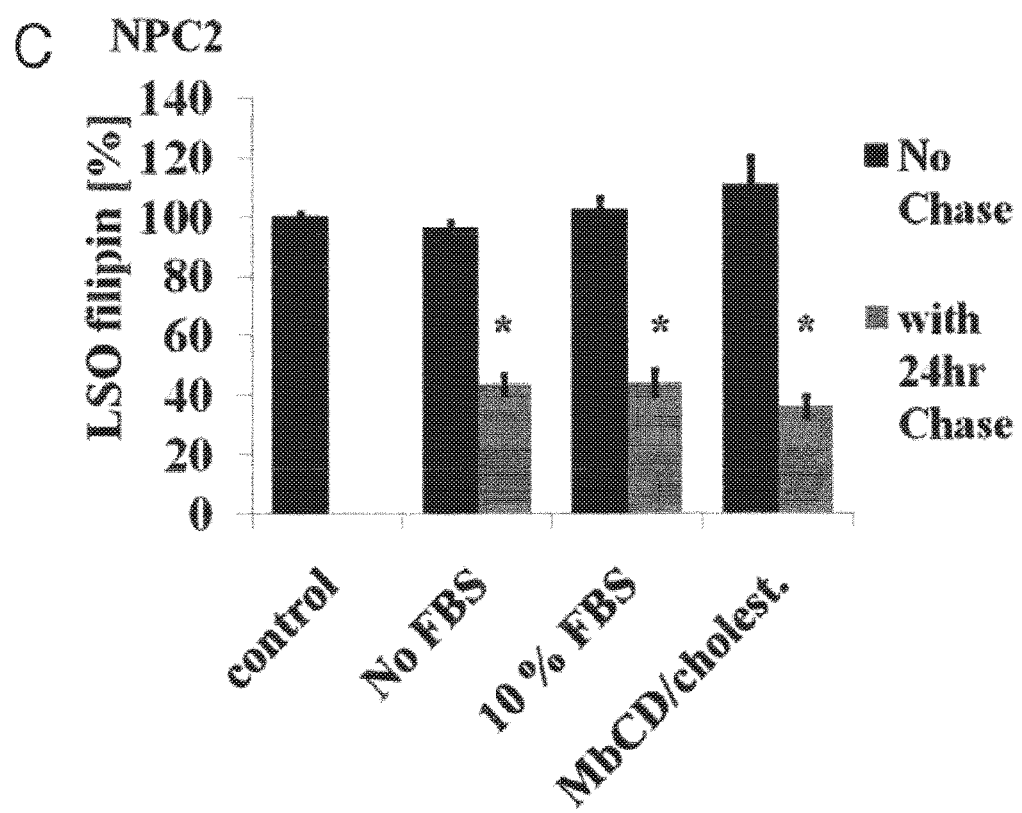

Cells that were fixed immediately after treatment with MβCD (with or without serum) showed no marked decrease in LSO filipin staining (FIG. 9). The cells that were treated with MβCD/cholesterol showed an overall increase in filipin staining (FIGS. 10B and 10D). Quantitative analysis of images taken 24 hours after the treatment with CD revealed that, regardless of the method of initial treatment, there was a significant reduction in filipin staining of LSOs of treated cells as compared with untreated controls (FIG. 10). These findings are consistent with a mechanism in which CD is acting from the inside LY/LE to compensate for the lack of functional NPC1 or NPC2.

Example 5

MβCD-Dextran Conjugates Also Reduce Cholesterol Accumulation in NPC Mutant Cells The endocytic uptake of dextran polymers and their delivery to the LE/LY has been characterized in many studies (S. Mukherjee, et al., *Physiol. Rev.*, 77 (1997) pp. 759-803). To ensure CD delivery to LSOs, MβCD was covalently conjugated to dextran polymers via a polyethylene glycol linker. As shown in FIG. 11A, MβCD-dextran can also reverse cholesterol accumulation in the LSOs of NPC1-defective cells. To visualize CD trafficking, MβCD-dextran conjugates were labeled with AlexaFluor546. This conjugate was observed to be localized to intracellular organelles that were labeled with filipin (FIG. 11B). Thus, the MβCD-dextran-AlexaFluor546 polymer has been shown to be in the LSOs.

Example 6

Effects of Acute CD Treatments on Cholesterol Esterification

Figure 12A:
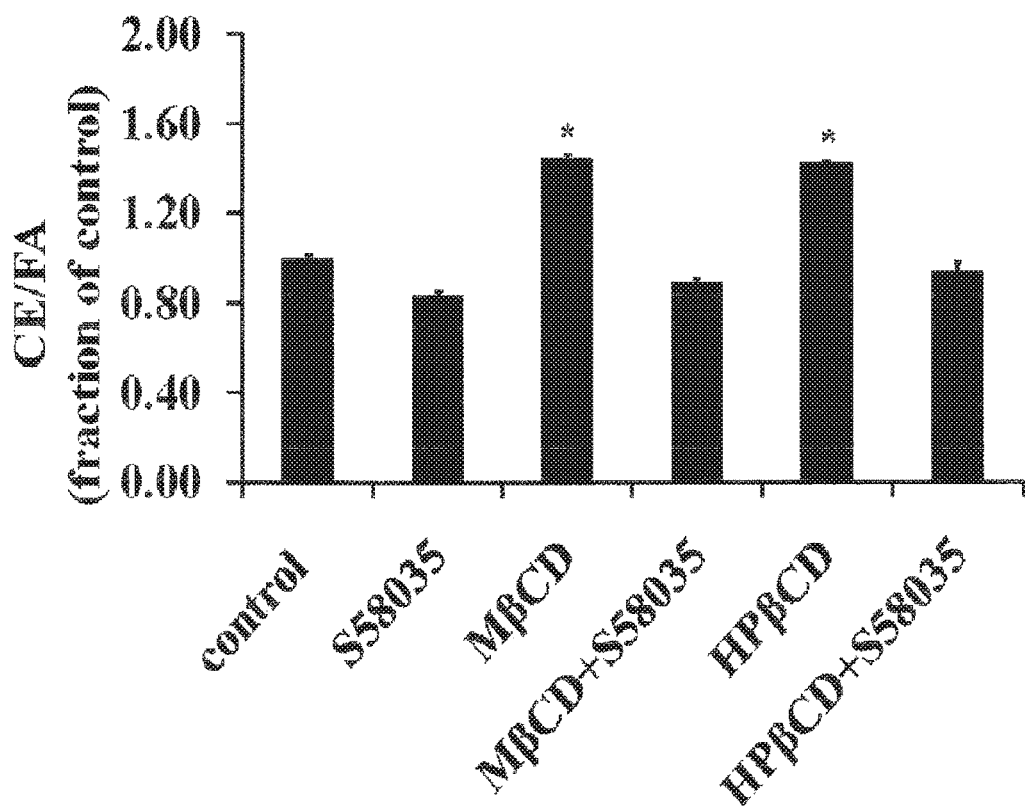
FIG. 12 A, B. Charts showing cholesterol esterification by ACAT. Cyclodextrin effects on cholesterol esterification in NPC1 (A) and NPC2 (B) mutant cells. Cells were treated for 1 hour with 3 mM MβCD or HPβCD and then allowed to recover in growth medium for 16 hours. Cells were then incubated with 3 µM 4,4-difluoro-4-bora-3a,4a-diaza-s-indacene-dodecanoic acid (BODIPY-C12) for 6 hours. The ratio of cholesteryl-BODIPY-C12 ester (CE)/BODIPY-C12 acid (FA) after TLC separation was measured and normalized to the average control value. ACAT inhibitor S58-035 was added, where indicated, at 10 µg/mL. For NPC1-defective cells, the average ratio was 0.110±0.007, which corresponded to 3.73±0.22 fmol CE formed per µg cell protein during 6 hours. Corresponding values for NPC2-defective cells were 0.089±0.003 and 2.50±0.24 fmol/µg. Data represent averages±SEM of two to three independent experiments. *$P<0.0001$ vs. control (6≤n≤16, where n is total number of wells per condition used for quantification).
Figure 12B:
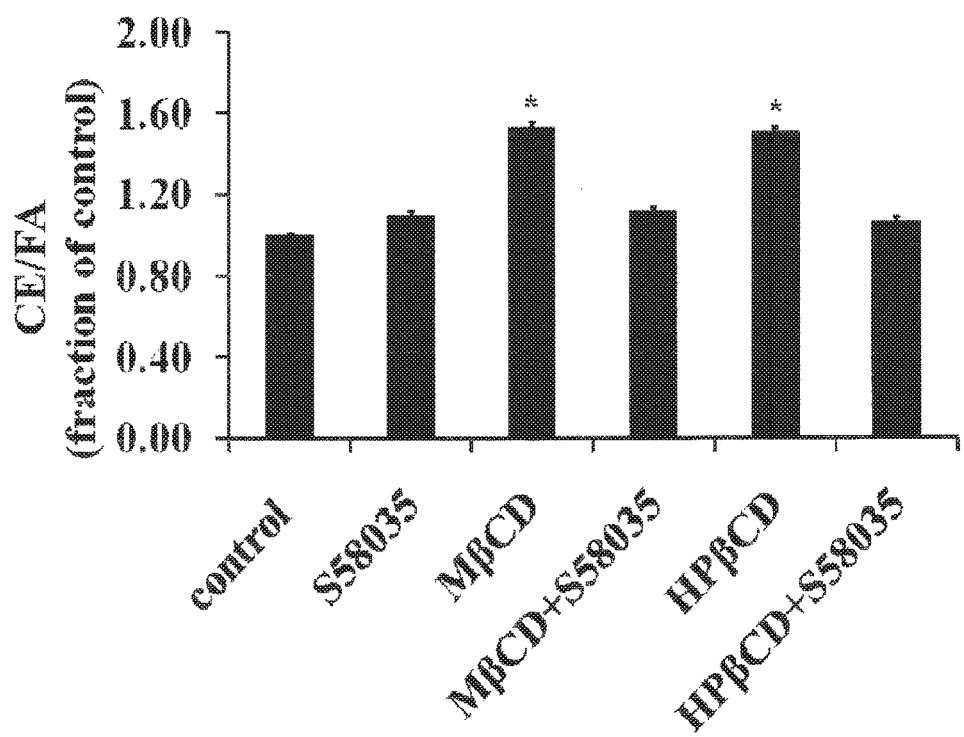
Figure 13A:
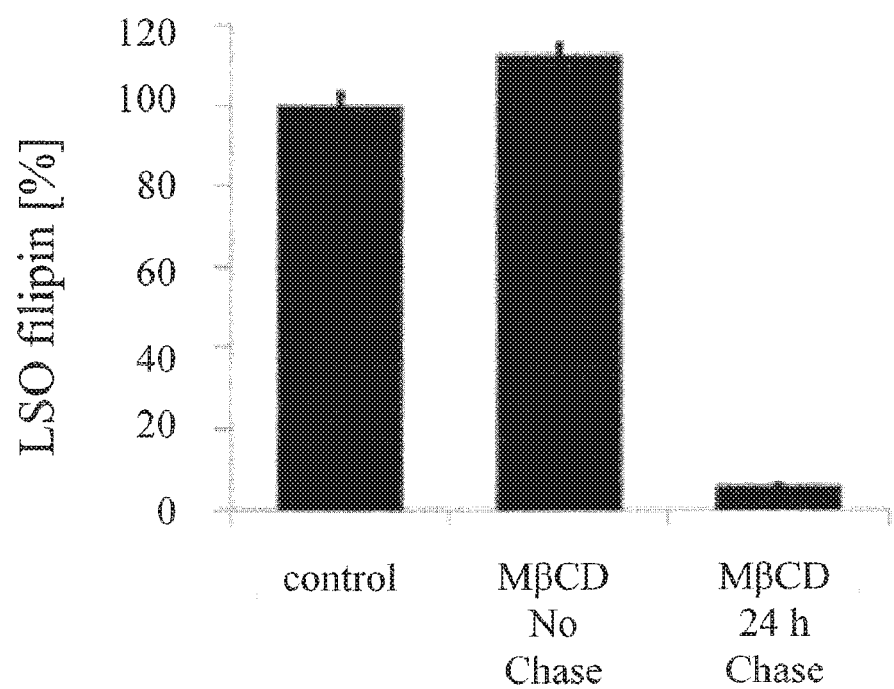
FIG. 13 A, B. Charts showing LSO filipin values for the ACAT assay. LSO filipin levels were measured immediately (no chase) or after 24-hour chase after a 1-hour 3-mM MβCD treatment in NPC1 (A) and NPC2 (B) mutant cells. Data represent averages±SEM of two independent experiments (n=8 for treated samples, n=72 for untreated control, where n is total number of wells per condition used for quantification).
Figure 13B:
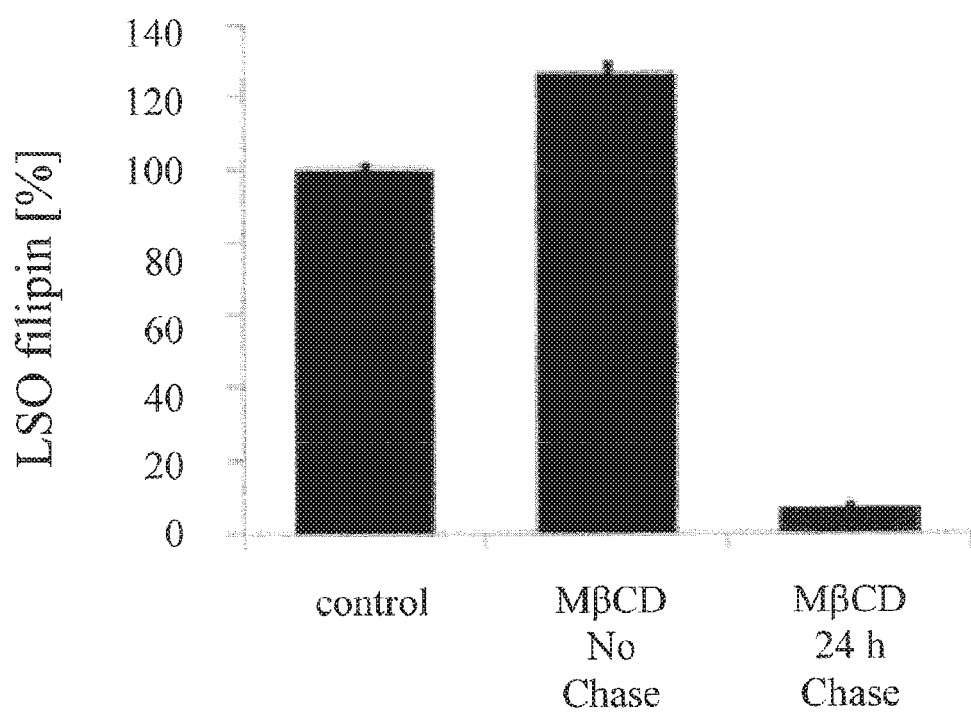

To measure cholesterol levels within the endoplasmic reticulum in response to brief CD treatments, cholesterol esterification was measured by ACAT (FIG. 12). Increased esterification of cholesterol was observed several hours after a short (1-hour) CD treatment of NPC1- or NPC2-deficient cell lines. This increase was inhibited by compound S58-035, an ACAT inhibitor (A. C. Ross et al., (1984) *J. Biol. Chem.* 259:815-819.), thus demonstrating that the increase in esterification was mediated by ACAT. Corresponding reductions in cholesterol accumulation upon MβCD treatment, as measured by the LSO filipin assay, are shown in FIG. 13.

Example 7

β-CD Effects on U18666A-Treated Fibroblasts

Figure 14A:
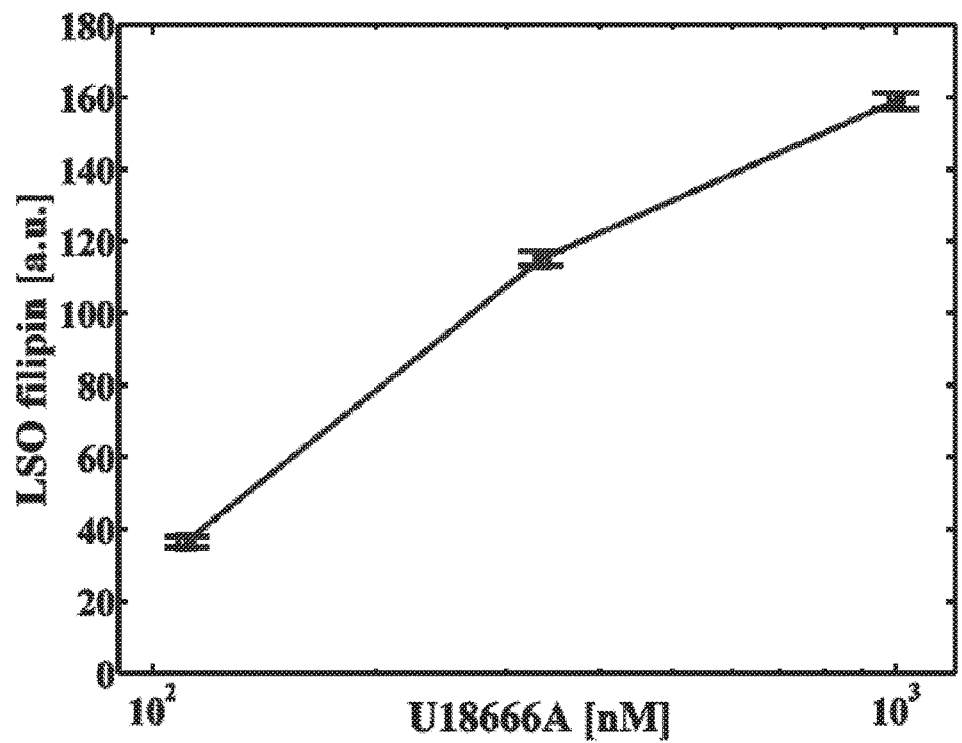
FIGS. 14 A-D. Cyclodextrin effects on cholesterol accumulation in U18666A-treated apparently normal human fibroblasts. Cells were plated in 384-well assay plates at a density to produce ≈80-90% confluency by experiment completion and treated with U18666A at indicated concentrations for 24 hour before addition of various concentrations of either MβCD or HPβCD for another 24 hours, during which indicated U18666A levels were maintained. At the end of the experiment, cells were fixed with 1% PFA and stained with 50 µg/mL filipin. Images were acquired using an ImageXpressMICRO imaging system with a 10× objective. LSO filipin quantification was performed as described previously (N. H. Pipalia, et al., Ibid.). (A) Cholesterol accumulation, as measured by the LSO filipin assay, at different concentrations of U18666A. MβCD (B) and HPβCD (C) LSO filipin dose-response curves at three different U18666A concentrations. (D) MβCD and HPβCD EC50 (from Table 2) dependence on U18666A concentration. Data represent averages±SEM of two independent experiments (n=12 for control and n=6 for treated, where n is total number of wells per condition used for quantification).
Figure 14B:
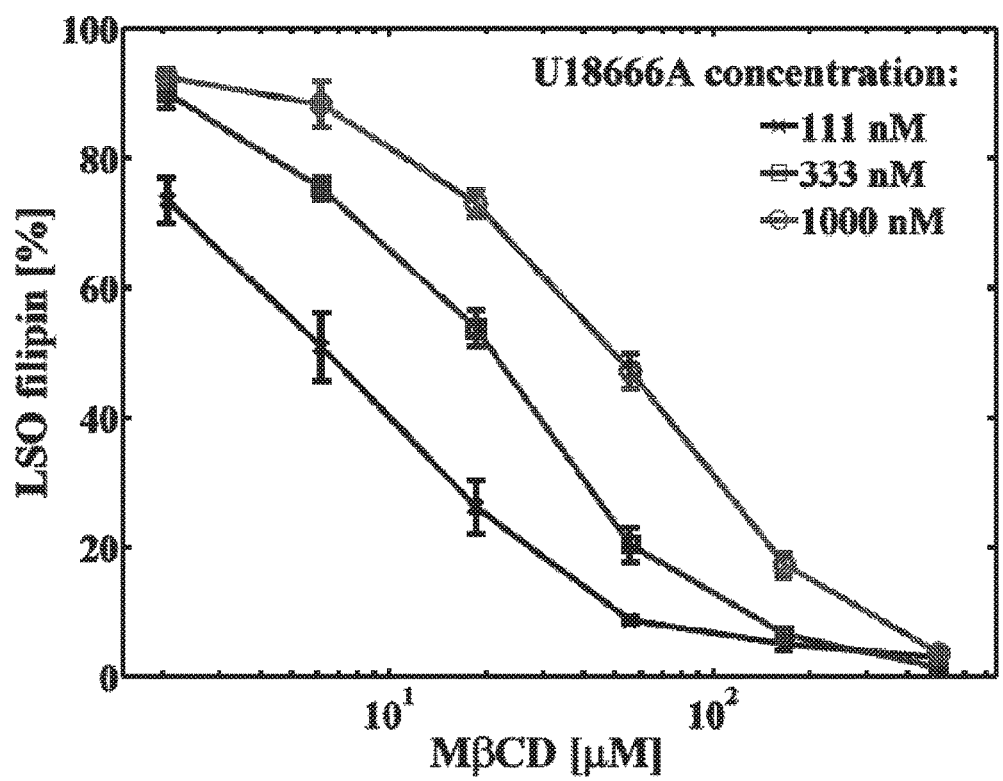
Figure 14C:
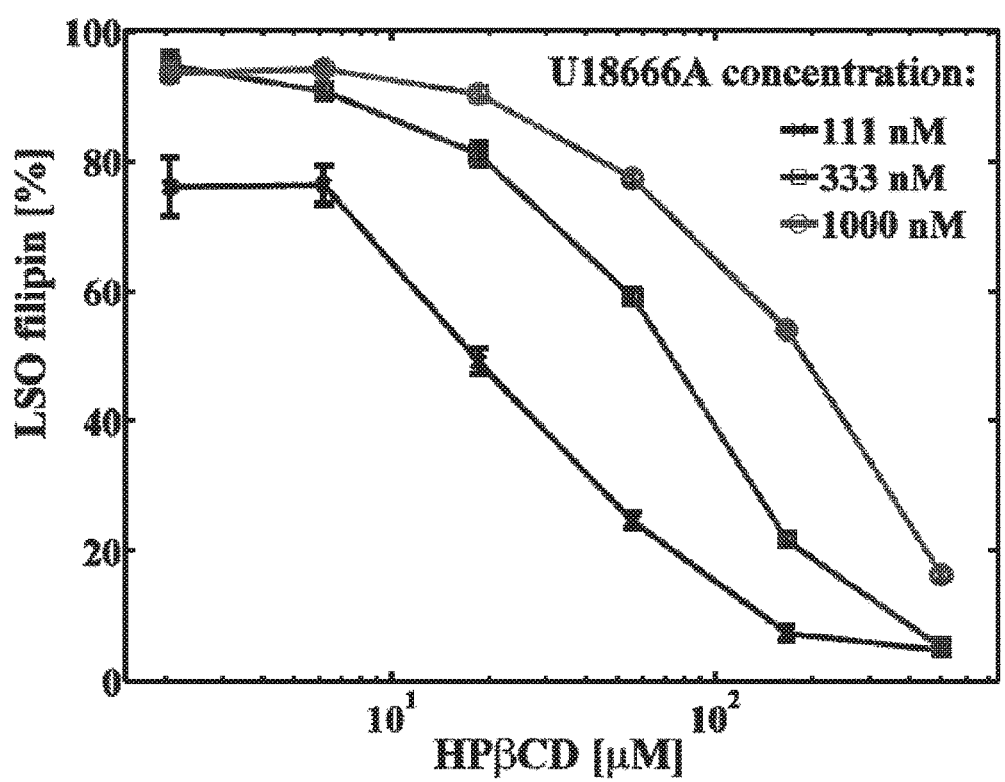
Figure 14D:
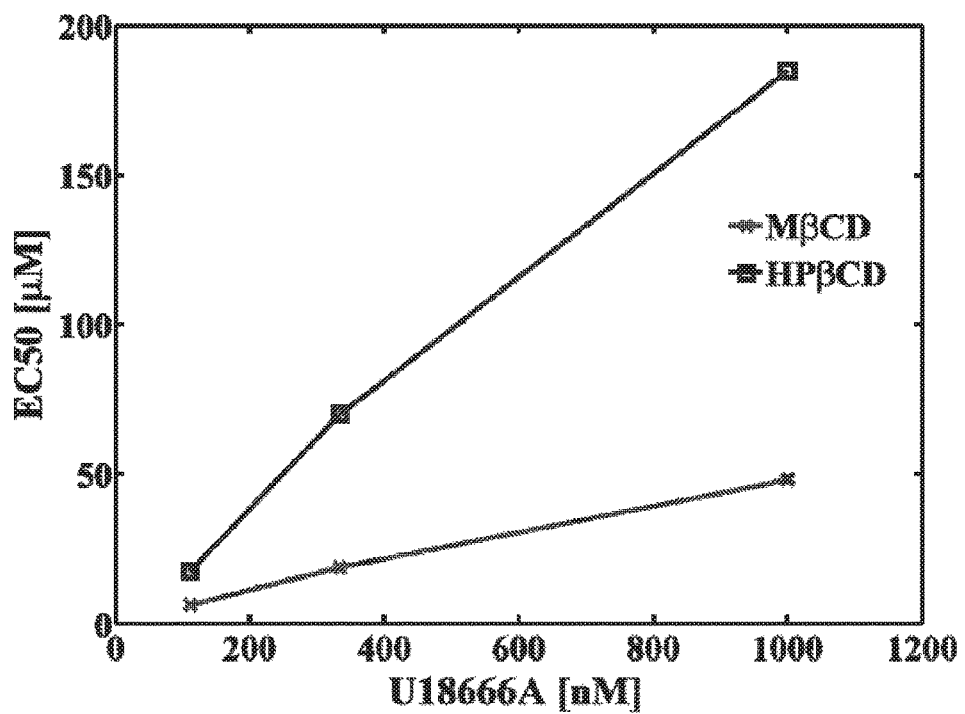

To test whether the apparent EC50 for clearance of cholesterol from LSO depended on cholesterol levels accumulated and to examine this in an isogenic background, this experiment used apparently normal human fibroblasts (GM05659) treated with various concentrations of the NPC phenotype-inducing compound U18666A (3-β-[(2-diethylamino)ethoxy]androst-5-en-17-one). U18666A is a class II amphipathic amine that has been reported to impair cholesterol efflux from LE/LY and create an NPC-like phenotype in treated cells (R. J. Cenedella, (2009) *Lipids* 44:477-487). The extent of cholesterol accumulation in LSOs of U18666A-treated cells is dose dependent (FIG. 14A). This accumulation can be reversed in a dose-dependent manner by using either MβCD or HPβCD (FIGS. 14B and 14C). The EC50s for clearance of cholesterol from U18666A-treated cells are summarized in Table 2 (below), and the dependence of EC50 on U18666A concentration is displayed in FIG. 14D. Higher levels of cholesterol in the cells require higher concentration of CD for clearance. The increased potency of MβCD vs. HPβCD has thus been demonstrated once again, and it seems to be more prominent for higher levels of cholesterol accumulation.

TABLE 2

Apparent $EC_{50}$ values for MβCD and HPβCD effects on LSO values of U186664-treated GM05659 cells as function of U18666A concentration.

| | Concentration U18666A (nM) | | |
|---|---|---|---|
| | 111 | 333 | 1,000 |
| $EC_{50}$ MβCD (μM) | 6.2 | 18.9 | 48.1 |
| $EC_{50}$ HPβCD (μM) | 17.4 | 69.9 | 184.9 |

Apparent $EC_{50}$S (compound concentration at 50% reduction in LSO filipin) for MβCD and HPβCD treatment of GM05659 apparently normal fibroblasts treated with 1M U18666A. Cells were pretreated with 1 μM U18666A for 1 day and then treated with the respective cyclodextrin for another day, in the continued presence of 1 μM U18666A compound. $EC_{50}$s were calculated as in Table 1. All fits had $R^2 \geq 0.97$.

Example 8

Effects of 3-CDs on BMP Accumulation in NPC-Defective Cells

Figure 15A:
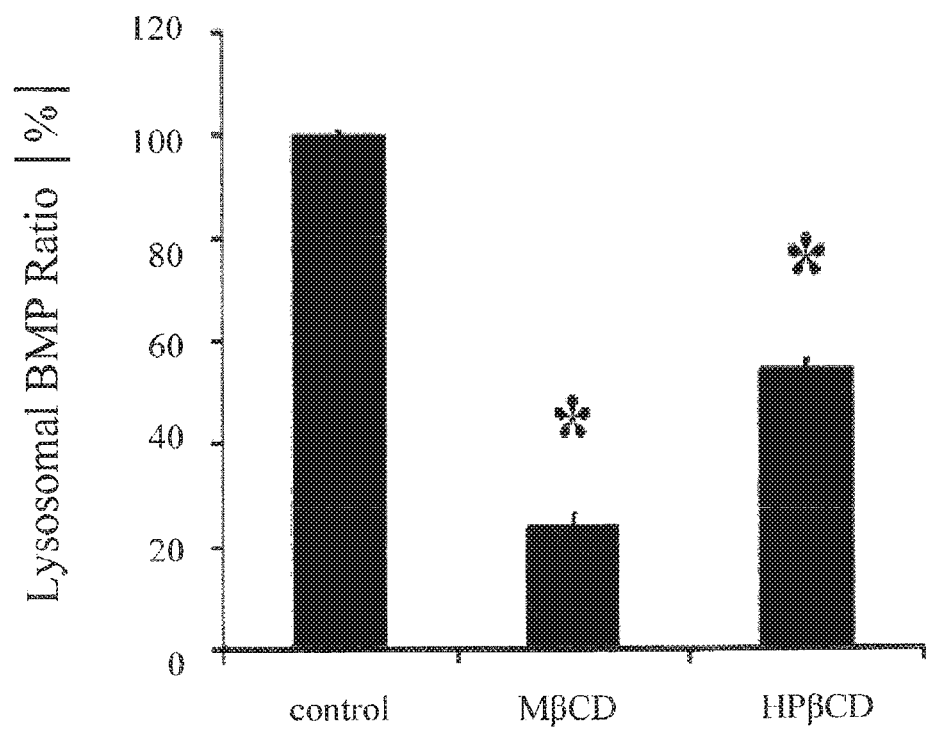
FIGS. 15 A-C. CD effects on BMP accumulation in NPC mutant cells. BMP levels were quantified using fluorescence microscopy from images obtained with a 20× objective of cells stained with anti-BMP antibody and AlexaFluor488-conjugated secondary antibody in NPC1 (A), NPC2 (B) mutant, and 1 µM U18666A-treated normal (C) cells. Cells were incubated with 0.9 mM CD for ≈1 day. Data represent averages±SEM of two independent experiments normalized to control (untreated) average value for each experiment. *P<0.0001 vs. control (n=16 for treated samples, n=64 for control, where n is total number of wells per condition used for quantification).
Figure 15B:
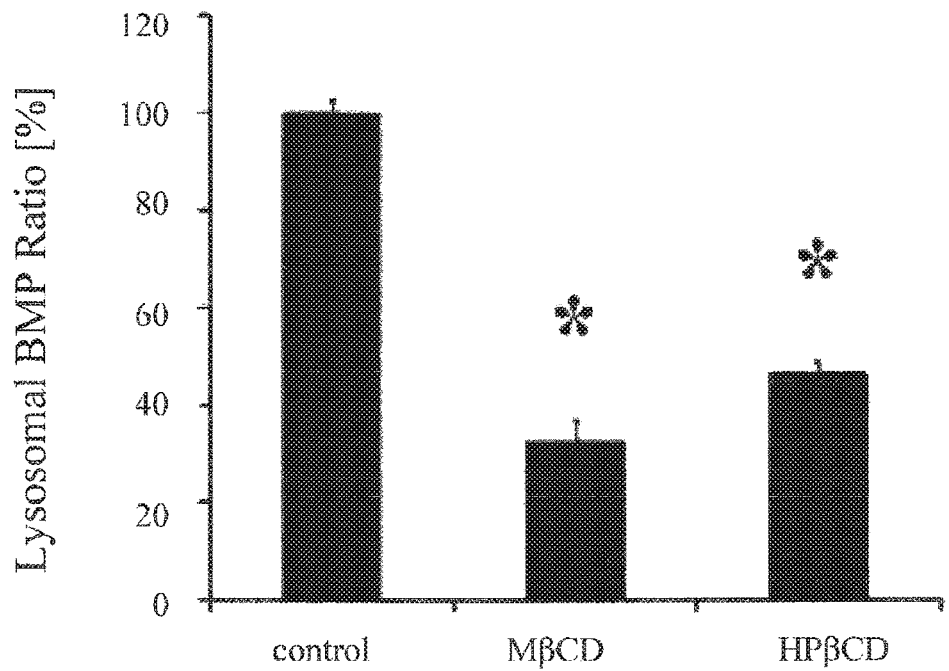
Figure 15C:
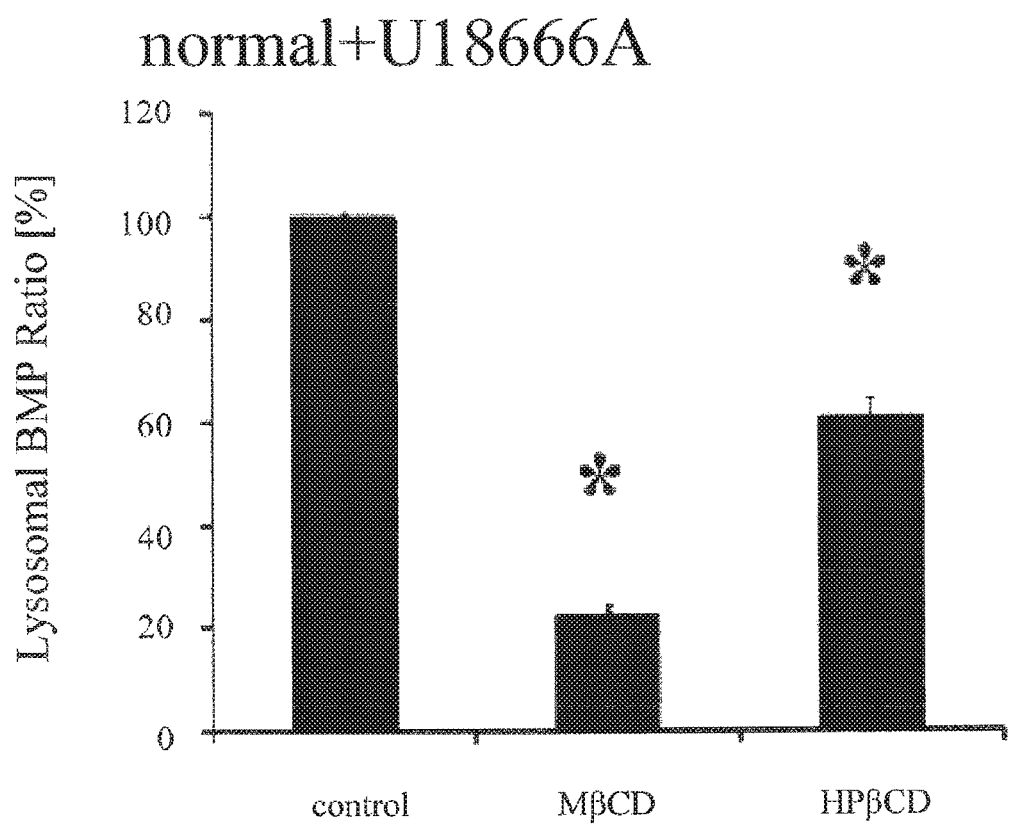
Figure 16:
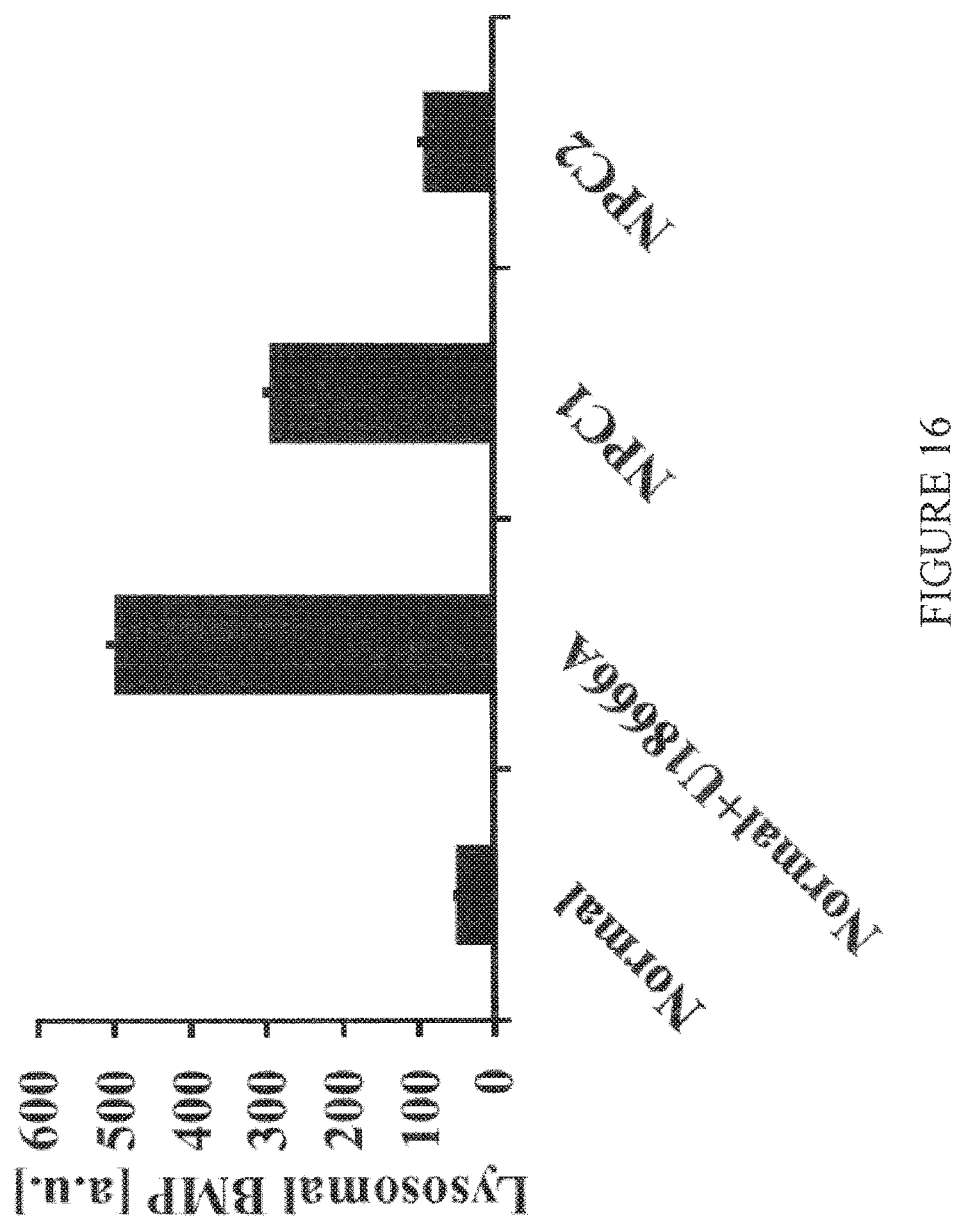
FIG. 16. Comparison of BMP accumulation in NPC1-defective, NPC2-defective, normal, and U18666A-treated normal fibroblasts. BMP levels were quantified using fluorescence microscopy from 20× magnification images obtained with anti-BMP antibody (clone 6C4) and AlexaFluor488-conjugated goat anti-mouse secondary antibody. Data represent averages±SEM of one representative experiment (n=32, where n is total number of wells per condition used for quantification).

Because levels of BMP are also elevated in the LSOs of NPC mutant cell (J. Chevallier, et al. (2008) *J. Biol. Chem.* 283:27871-27880), this experiment examined the effects of CDs on BMP accumulation in NPC mutant cells. Both MβCD and HβCD significantly reduced BMP accumulation, as measured by quantification of images of cells stained with anti-BMP antibody (FIG. 15). This indicates that secondary lipid accumulation was reduced along with cholesterol changes. Relative BMP levels in NPC1, NPC2, normal, and normal cells treated with U18666A are shown in FIG. 16.

Example 9

Discussion of Results

Studies in npc1−/− mice have demonstrated that single injections of HPβCD can extend their lifespan (e.g., F. Camargo, et al. (2001) *Life Sci.* 70:131-142; B. Liu et al. (2008) *J. Lipid Res.* 49:663-669; B. Liu, et al. (2009) *Proc. Natl. Acad. Sci. USA,* 106::2377-2382; S. Lope-Piedrafita, et al. (2008) *J. Neurosci. Res.* 86:2802-2807.). Subsequent studies with repeated injections of HPβCD have shown further prolongation of lifespan as well as clearance of various glycosphingolipids (C. D. Davidson, et al. (2009) *PLoS One* 4:e6951). These animal studies did not address the mechanism of action of CDs. A recent study (L. Abi-Mosleh, (2009) *Proc. Natl. Acad. Sci. USA* 106:19316-19321) used cultured NPC1- and NPC2-deficient cells to show that HPβCD treatment increased ACAT-mediated esterification of cholesterol even in the absence of functional NPC proteins.

In these experiments, the role of CD in reducing cholesterol accumulation in NPC mutant cells has been examined. CDs are hydrophilic, membrane impermeant molecules that can reach the inside of LE/LY via pinocytosis, similar to other membrane-impermeant molecules (Mukherjee 1997, Ibid.). Mammalian cells lack the enzymes for degradation of CDs (M. E. Davis et al., (2004) *Nat. Rev. Drug. Discov.* 3:1023-1035), and thus, CDs delivered to LE/LY are expected to remain intact.

Several lines of evidence suggest that the major effect of CDs in reducing cholesterol accumulation is attributable to endocytosed CD. The effects on cholesterol reduction in LSOs continue for several days after extracellular CD has been removed from the medium (FIG. 8). The slow loss of effectiveness of the CD would be consistent with reduced concentrations in the endocytic system as a consequence of cell division and vesicular transport out of lysosomes. It was also found that brief (1 hour) incubations with CD leads to a reduction in LSO cholesterol after about 24 hours in the absence of extracellular CD. This was observed even when the initial incubation was with cholesterol-loaded CD, which caused an initial increase in cellular cholesterol levels (FIG. 10). In experiments where MβCD was conjugated to dextran polymers to ensure its delivery to the LSOs, it was found that this compound was able to correct NPC1 deficiency (FIG. 11A). Additionally, it was found that these conjugates were delivered to LSOs (FIG. 11B). These observations further demonstrate that CDs can act from inside the lumen of the LSO.

Both NPC1 and NPC2 mutant cells were tested in this study, and both cell types responded well to treatment by CDs. These findings indicate that CDs are capable of replacing the function of either NPC1 or NPC2. Because NPC2 is a small, soluble protein that has been shown to transfer cholesterol between membranes in vitro (J. Storch, et al. (2009) *Biochim. Biophys. Acta.* 1791:671-678.), its functional replacement by CD can be envisaged easily. The mechanism underlying the ability of a CD to bypass the requirement for functional NPC1 is less clear. NPC1 is a large transmembrane protein residing in the limiting membrane of LE/LY, and its role in cholesterol efflux is not well understood despite recent advances in understanding its cholesterol binding properties (H. J. Kwon, et al. (2009) *Cell* 137:1213-1224; R. E. Infante, et al. (2008) *Proc. Natl. Acad. Sci. USA* 105:15287-15292). It is possible that to facilitate cholesterol egress from LE/LY, NPC2 has to interact with NPC1 to deliver cholesterol to the limiting membrane for egress (L. Abi-Mosleh, (2009) Ibid.; H. J. Kwon, et al. (2009) Ibid.), whereas a CD can bypass that requirement and deliver cholesterol directly to the limiting membrane. Once in the limiting membrane, cholesterol could leave the LE/LY by vesicular or nonvesicular transport processes (B. Mesmin, (2009) *Biochim. Biophys. Acta.* 1791:636-645) to be delivered to other organelles.

To verify that the cholesterol liberated by CD treatments reaches the cytosolic compartment, other experiments were conducted to measure esterification of cholesterol by ACAT. In those experiments, it was found that short treatments of either NPC1 or NPC2 cells with either CD, followed by a ~16-hour chase, lead to an increase in cholesterol esterification by ACAT, thus indicating that more cholesterol is delivered to the endoplasmic reticulum in CD-treated cells (FIG. 13).

BMP is an unusual lipid that is present in high levels in late endosomes, and elevated levels of cholesterol associated with NPC mutations or treatment with U18666A lead to elevated levels of BMP in the LSOs (J. Chevallier, et al. (2008) Ibid.; T. Kobayashi, et al. (1999) *Nat. Cell Biol.* 1:113-118). To verify that the effects of CD treatment go beyond merely cholesterol reduction, BMP levels were measured in treated and untreated cells. From these experiments, it was found that the BMP levels were reduced significantly by CD treatments (FIG. 15). This is consistent with the observation in npc1−/− mice that CD treatments reduce levels of storage of other lipids in addition to cholesterol (C. D. Davidson, et al. (2009), Ibid.).

The work described herein supports the utility of the instant CD-based compositions for the treatment of NPC disease. Furthermore, it has been found herein that MβCD produces effects equivalent to those of HPβCD at approximately three-fold lower concentrations. This is consistent with the better ability of MβCD to extract cholesterol from biologic membranes. This observation may be important because relatively high amounts of HPOCD need to be injected to obtain a partial therapeutic effect (e.g., F. Camargo, et al. (2001) Life Sci. 70:131-142; B. Liu et al. (2008) J. Lipid Res. 49:663-669; B. Liu, et al. (2009) Proc. Natl. Acad. Sci. USA, 106::2377-2382; S. Lope-Piedrafita, et al. (2008) J. Neurosci. Res. 86:2802-2807). Additionally, the observation that CD works from inside LE/LY suggests that modifications that target CDs for endocytic uptake and retention might significantly enhance its potency.

While the main focus in these examples has been optimizing intracellular targeting of MβCD, the methods described herein are also useful for targeting compounds within the body. In particular, it has been reported that some peptides, such as a 29 residue peptide from the rabies virus coat protein, can bind to receptors on brain endothelial cells and facilitate transcytosis into the brain (P. Kumar, et al., Nature, 448 (2007) pp. 39-43). It is relatively easy to link such peptides to the polymeric compositions of the instant invention. Such peptides have been found to not interfere with the intracellular targeting and cholesterol reduction properties of the polymers.

Example 10

HDAC Inhibitors

Figure 17:
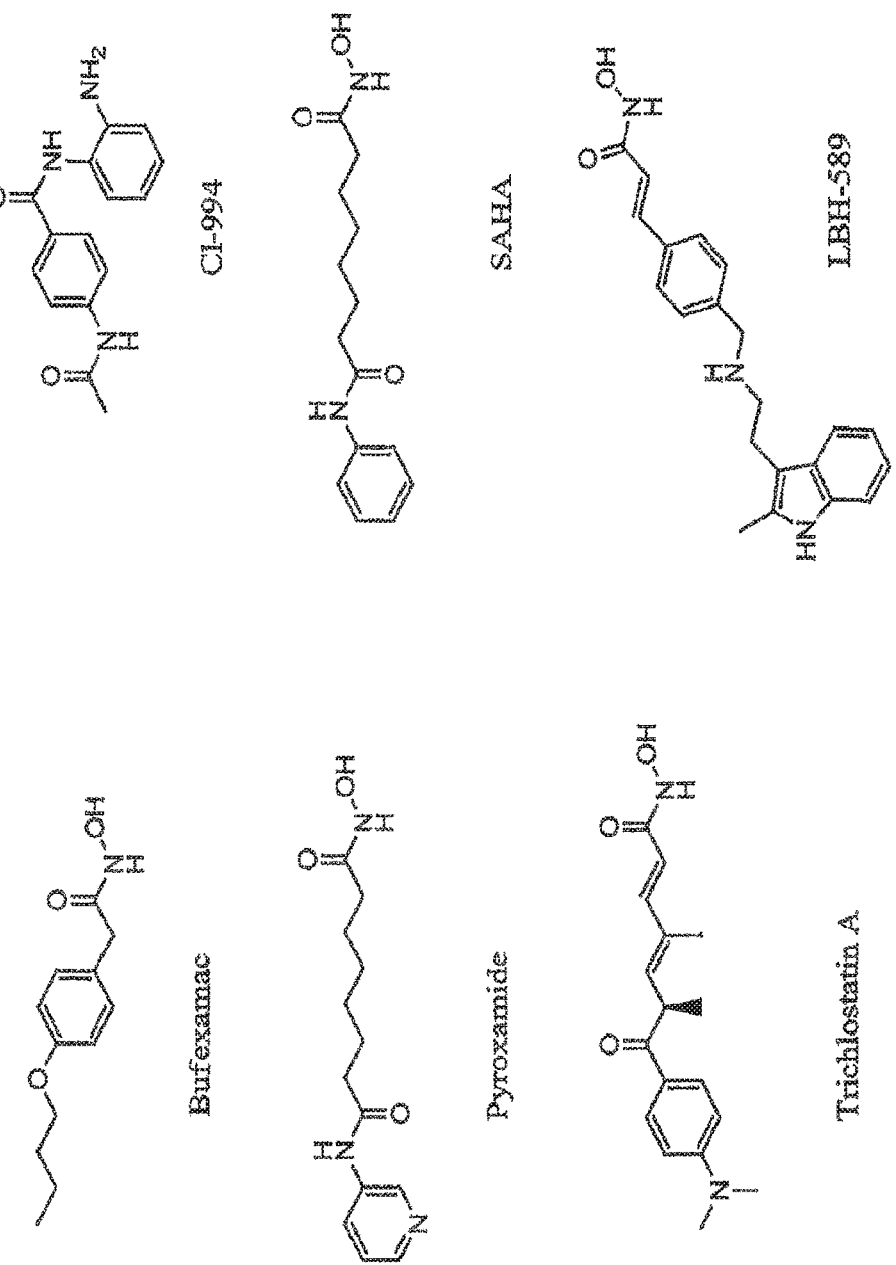
FIG. 17. Chemical structures of various HDAC inhibitor compounds (bufexamac, C1-994, pyroxamide, SAHA, trichostatin A, LBH-589).
Figure 18A:
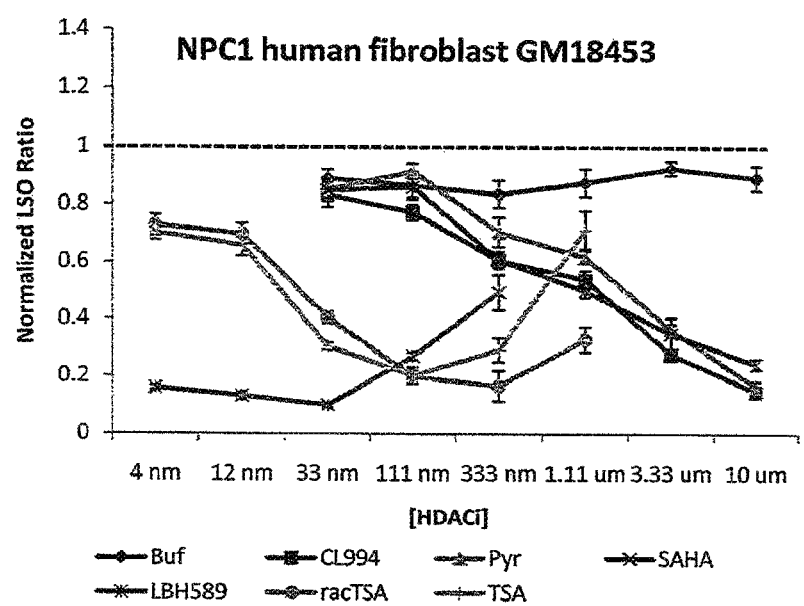
FIG. 18 A, B. Graphs showing the dose dependent effect of HDAC inhibitors on cholesterol accumulation in human NPC1 fibroblasts. Cells were treated in complete medium for two days (48 hours). The dashed horizontal line is 3SD below the mean for untreated cells. (A) results for NPC1 human fibroblast GM18453, (B) results for NPC2 human fibroblast GM18445.
Figure 18B:
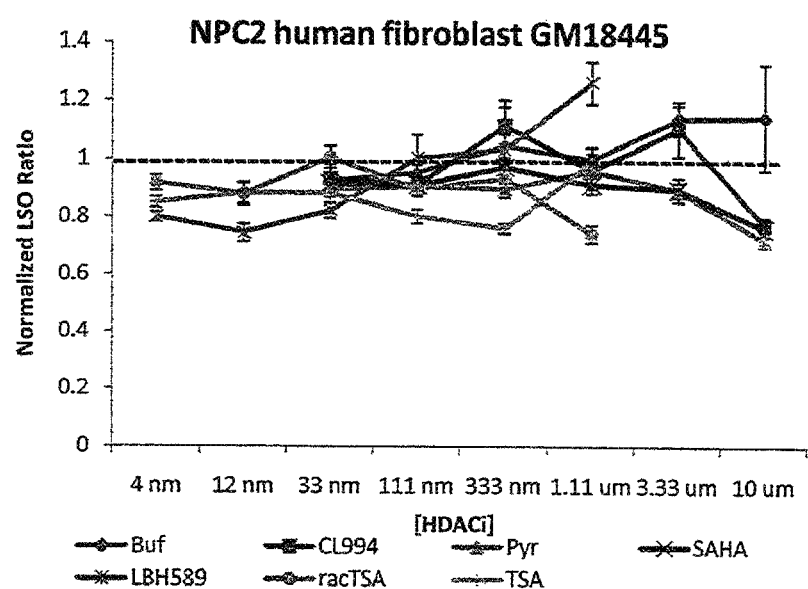

Tests were conducted to determine the ability of several HDAC inhibitors (HDACi) to reduce cholesterol in the LSOs following a 48-hour treatment at various concentrations. The structures of six of the HDAC inhibitors used in this study are shown in FIG. 17. The dose dependence of various HDACi inhibitors after the 48-hour treatment is shown in FIGS. 18A and 18B. FIG. 18A shows the results for NPC1 human fibroblast GM18453. FIG. 18B shows the results for NPC2 human fibroblast GM18445. Each data point in the plot is representative of a total of 32 images from two independent experiments. The standard deviation (SD) for DMSO is 0.07, error bar=SE. The dotted line represents the DMSO control. As shown, both trichostatin A (TSA) and LBH-589 were significantly effective at 37 nM, and LBH-589 was effective at 4 nM.

Figure 19:
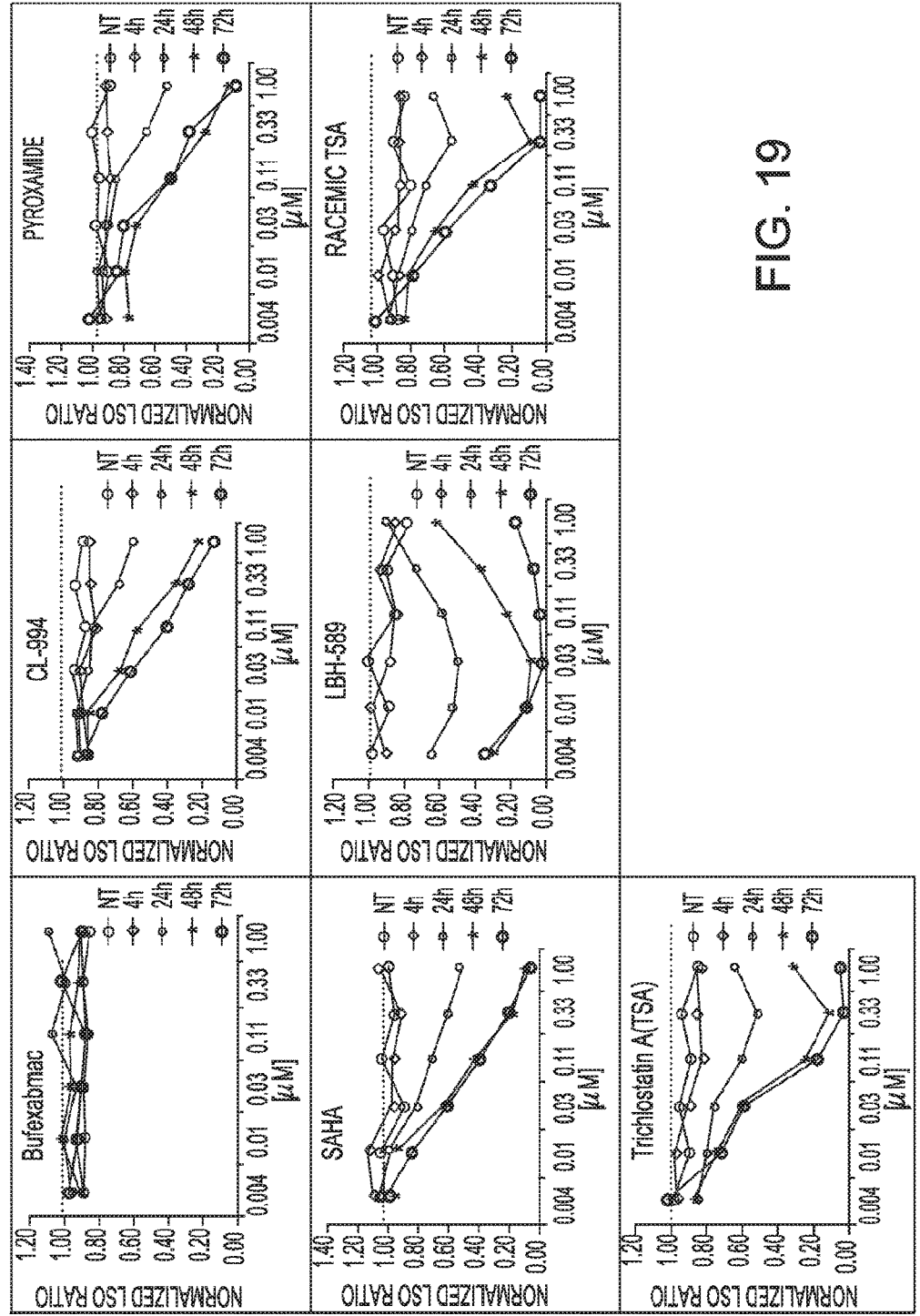
FIG. 19. Plots showing the dose and time dependence for each of the studied HDACi compounds as a function of time on NPC1 fibroblast GM03123.

Dose and time dependence for each of the studied HDACi compounds as a function of time on NPC1 fibroblast GM03123 are shown in the plots of FIG. 19. Each data point in the plot is representative of a total of 32 images from two independent experiments. The SD for DMSO is 0.07, error bar=SE. The dotted line represents the DMSO control. SAHA was somewhat effective at 1 M, and it was much more effective in other experiments at 10 μM (not shown). Both SAHA and LBH-589 target class I & H HDACs, and the relative potency in the cholesterol reduction parallels their relative potency for inhibition of HDAC (M. Dokmanovic, et al., Histone deacetylase inhibitors: overview and perspectives, Mol. Cancer Res., 5 (2007) pp. 981-989).

Some HDAC inhibitors were found to be remarkably effective in reducing cholesterol accumulation in LSOs. It should be noted that some of these HDAC inhibitors are in use for treating neuroblastoma, so they apparently cross the blood-brain barrier easily.

Several other HDAC inhibitors were assayed. Concentration dependence was assayed as before, and assays were conducted at a range of exposure times from 4 hours to 4 days. The results show that two inhibitors of the Class I and II HDACs are very potent in reducing cholesterol accumulation.

Effects of the HDACs on LDL uptake, cholesterol synthesis, lysosomal acid lipase activity, ACAT activity, and cholesterol efflux were also characterized to identify which cellular processes are responsible for lowering accumulated cholesterol. HDACs have many cellular targets, and their effects can be pleiotropic. In addition to histones, in which the acetylation state can affect expression of many genes, many cytoplasmic proteins are also regulated in their function by acetylation/deacetylation. For some of the HDAC inhibitors most effective at reducing LSO cholesterol, a variety of routine biochemical assays were employed to determine which step(s) of cholesterol transport or metabolism are being affected.

Figure 20:
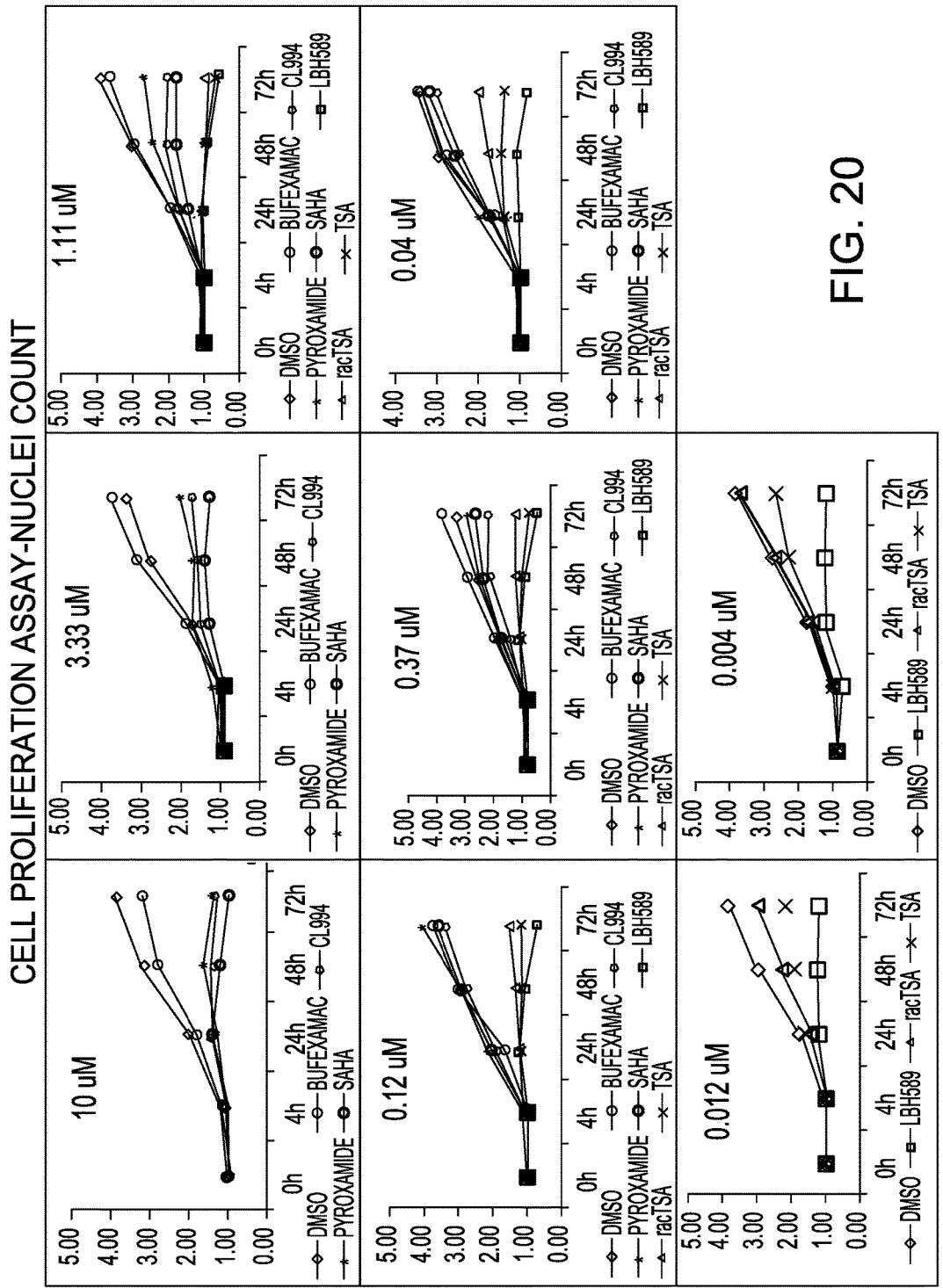
FIG. 20. Plots showing the effect of various HDACi compounds on cell proliferation. The effect was monitored at 4 h, 24 h, 48 h and 72 h post treatment by counting the number of nuclei. Each data point in a plot is representative of a total of 32 images from two independent experiments. Error bar=SE.

FIG. 20 shows the effect of various HDACi compounds on cell proliferation. The effect was monitored at 4 h, 24 h, 48 h and 72 h post treatment by counting the number of nuclei. Each data point in a plot is representative of a total of 32 images from two independent experiments. Error bar=SE.

Figure 21:
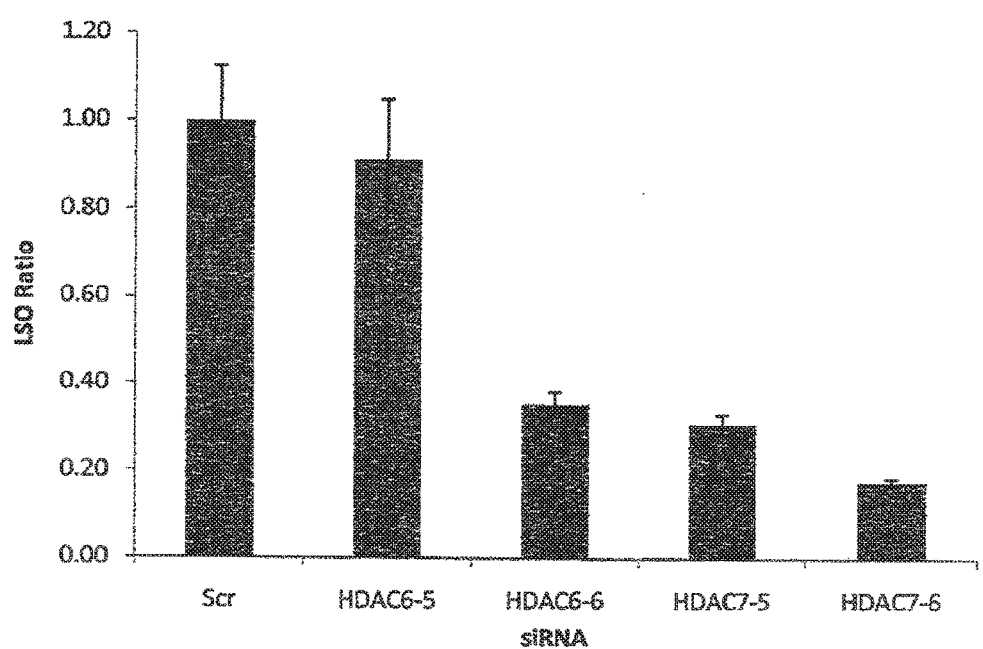
FIG. 21. Plot showing a filipin assay after HDAC silencing in GM03123 cells by electroporation. The plot is representative of three independent experiments for HDAC 6 and two independent experiments for HDAC7A.

FIG. 21 shows data from a filipin assay after HDAC silencing in GM03123 cells by electroporation. The plot is representative of three independent experiments for HDAC 6 and two independent experiments for HDAC7A.

The results above demonstrate that HDAC inhibitor treatment dramatically reduces cholesterol accumulation in lysosomal storage organelles of NPC skin fibroblasts.

Example 11

Acid SMase Restoration

Materials and Methods

The tissue culture plasticware used in these experiments was purchased from Fisher Scientific Co. Tissue culture media and other tissue culture reagents were purchased from Invitrogen Corp. FBS was obtained from Gemini Bio-Products. LDL (d, 1.020-1.063 g/mL) from fresh human plasma was isolated by preparative ultracentrifugation as described elsewhere (Havel 1955). Radiochemicals were purchased from either Perkin-Elmer Life and Analytical Sciences, Inc., or American Radiolabeled Chemicals, Inc. All restriction enzymes, Antarctic phosphatase and T4 DNA ligase were purchased from New England BioLabs. Recombinant human acid SMase was prepared from transfected CHO cells and purified as previously described (He 1999). All other chemicals and reagents were from Sigma-Aldrich, and all organic solvents were from Fisher Scientific Co.

Cells.

CHO, 25RA (Chang 1980) and CT60 cells (Cadigan 1990; Watari 1999) were grown in monolayer cultures in Ham's F12 medium containing 10% FBS. Human WT (GM05659) and NPC (GM03123) Fbs, from Coriell Institute of Medical Research, were cultured in Modified Eagle's Medium (MEM) containing 10% FBS. The NPC Fbs were derived originally from a 9-year-old compound heterozygote female, with missense mutations in exon 6 of one allele (P237S) and exon 21 of the other allele (I061T). The fibroblasts from this subject expressed no detectable NPC1 protein by immunoblot analysis and, as expected, had a severe defect in the trafficking lipoprotein-derived cholesterol (Yamamoto 2000; Pentchev 1985). The GM18453 NPC Fbs were derived from a male donor with a homozygous mutation at I1061T. All cells were plated at a minimum of 24 h prior to commencement of the experiment.

Acid SMase Activity Assay.

Cell extracts were prepared by scraping cells into ice-cold 250 mM sucrose, followed by sonication on ice twice for 10 seconds each using a Branson Sonifier 450. To prepare the substrate, solvent from 0.1 µCi [cholinemethyl-$^{14}$C] SM (52 mCi/mmol; Perkin-Elmer Life and Analytical Sciences) was evaporated, and the labeled SM was resuspended in 20 µL of assay buffer (100 mM sodium acetate pH 5.0, 100 µM ZnCl2) containing 2.7% Triton X-100 and vortexed for 2 minutes. The assay solution, which was added to 1.5-mL microcentrifuge tubes on ice, consisted of 50 µL assay buffer, 20 µL substrate and 20 µL of cell extract. After incubation for 60 minutes at 37° C., the reaction was terminated by adding 125 µL of chloroform:methanol (2:1, v/v). The assay tubes were vortexed for 1 minute and then centrifuged 5000×g for 5 minutes at 4° C. A 50-µL aliquot of the upper aqueous phase was removed for scintillation counting to determine the amount of [$^{14}$C] phosphorylcholine released from [$^{14}$C] SM. The protein content of the cell extracts was assayed using the method of Lowry (Lowry 1951).

Cellular cholesterol mass determination by gas chromatography. In Ham's F12 growth medium supplemented with 10% FBS, 25RA, CT60, CT60-VEC, CT60-WT and CT60-C629 cells were grown. Lipids were extracted from the cells with hexane:2-propanol (3:2) and separated on a Varian Factor Four capillary column (VF-1 ms 30 m×0.25 mm IDDF 0.25) using Varian 4000 GC/MS/MS system. The injector temperature was 270° C. The following temperature gradient was used: initial temperature was 115° C., which was raised to 260° C. at 9° C./min and held for 2.89 minutes, then raised to 269° C. at 3° C./min and again to 290° C. at 9° C./min and held for 4.67 minutes. Flow rate was 5 mL/min He(g). Electron ionization was used with the current set at 10 µA. Total ionic current was used for detection (50-1000 m/z). β-Sitosterol was used as an internal standard for quantification of µg free cholesterol per mg cell protein. Protein concentration was determined with modified Lowry reagent (Bio-Rad).

Sphingomyelin Mass Assay.

Total cellular SM mass was quantified in lipid extracts of cells using the TLC-Bartlett procedure as previously described (Okwu 1994; Bartlett 1959), except that the scraped thin-layer chromatography (TLC) spot was extracted with methanol:chloroform (2:1).

Preparation of WT or C629S SMPD1 Constructs.

A plasmid containing the human cDNA for acid SMase (SMPD1)(56) was digested with EcoRI to release the cDNA. The cDNA was then ligated to phosphatase-treated, EcoRI-digested pBSIISK (Stratagene) to generate pBS.SMPD1. To obtain the 3 ends of the cDNA designed to encode WT or C629S acid SMase, polymerase chain reaction (PCR) was conducted using the high-fidelity Platinum Pfx DNA polymerase (Invitrogen) and the pBS.SMPD1 plasmid as the template. For both constructs, a NotI site was created after the stop codon to assist in the cloning process. The primers for the WT construct consisted of the sense primer SMPD11469 (SEQ ID NO. 1: 5-ACTGTCT-GAAGAGCTGGAGCT-3) and the antisense primer SEQ ID NO. 2: 5TTTTATTGCGGCCGCCTAGCAAAACAGTG-GCCTTGG-3. The sense primer for the C629S construct was SMPD11469 and the antisense primer was SEQ ID NO. 3: 5-TTTTATTGCGGCCGCCTAGGAAAACAGTGGC-CTTGG-3 (the codon for serine in position 629 is underlined). Each PCR product was digested with SphI (which cuts at position 1860 of SMPD1 cDNA) and NotI, and then separately ligated to the 4.8-kb SphI-NotI fragment from pBS.SMPD1 to generate pBS.WT or pBS.C629S, in which the polyadenylation sequence was removed from the SMPD1 cDNA. The final vectors were created in the expression vector pIRES-hrGFP II (Stratagene) by ligating the 6-kb EcoRI-NotI fragment from the vector with the 2-kb EcoRI-NotI fragment from either pBS.WT or pBS.C629S to generate pIRES.WT or pIRES.C629S. The DNA sequence was confirmed for each construct. The vector pIREShrGFP II consists of the SV40 promoter driving the expression of the neomycin-resistance gene and a bicistronic expression cassette under the control of the human cytomegalovirus promoter which contains a multiple cloning site followed by an internal ribosome entry site (IRES) that is linked to the GFP coding sequence.

Transfection of Cells with the WT or C629S SMPD1 Constructs.

For transient transfection, CT60 cells in 16-mm wells were transfected with 340 ng empty vector (pIRES-hrGFP II; VEC), pIRES.WT or pIRES.C629S using Lipofectamine 2000. For stable transfection, CT60 cells were transfected with the empty vector, pIRES.WT or pIRES.C629S, and then selected for growth in G418 (0.5 mg/mL) and named, respectively, CT60-VEC, CT60-WT and CT60-C629S. Human fibroblasts were transiently transfected using a reverse format with Effectene (Qiagen, Valencia, Calif.) as the transfection reagent. Briefly, VEC, WT and C629S vectors (above) were mixed with Effectene transfection reagent, enhancer and manufacturer-supplied buffer (EC) in the ratio recommended by the manufacturer and dispensed in different wells of a six-well plate. The fibroblasts were then added to the above mixture in suspension and incubated overnight at 37° C. in a tissue culture incubator. Fresh growth medium was added to the cells and, after an additional 6 h of incubation, the cells were fixed and analyzed for filipin and/or GFP staining (as described below).

Acid SMase Enzyme Replacement.

Normal (GM05659) and NPC1 human fibroblasts (GM03123) were incubated in a medium containing 3 µg/mL recombinant human acid SMase (rhASM). Two days later, the cells were washed thoroughly with PBS, and either lysed and assayed for acid SMase activity or fixed and stained with filipin for imaging and quantification. NPC1 human fibroblasts GM18453 were treated with 3 µg/mL rhASM for 24 h before fixing, staining with filipin, imaging and quantifying.

Alexa555-Conjugated rhASM Enzyme Replacement.

For identifying the localization of rhASM in the cells, recombinant enzyme was conjugated with Alexa555 (Invitrogen) according to the manufacturer's protocol. Normal (GM05659) and NPC1 human fibroblasts (GM03123) were incubated in a medium containing 3 µg/mL Alexa555-rhASM for 24 h prior to fixing and staining with filipin. Images were acquired using standard UV and TRITC filters for filipin and Alexa555-labeled rhASM, and quantified.

Filipin Staining.

Cells were plated onto poly-d-lysine-coated 35-mm coverslip dishes in a medium containing 10% FBS. After 1-2 days of growth, the cell monolayers were washed three times with PBS and then fixed with 3% paraformaldehyde in PBS for 20 minutes at room temperature, followed by three more washes with PBS. To detect free cholesterol, filipin was added to the fixed cells (50 µg/mL in PBS) for 45 minutes at room temperature. Finally, the cells were washed three times with PBS, and images were acquired immediately after labeling.

Fluorescence Microscopy.

Fluorescence microscopy and digital image acquisition were carried out using a Leica DMIRB microscope (Leica Mikroscopie und Systeme GmbH) equipped with a cooled Charge Coupled Device (CCD) camera (Princeton Instruments) and driven by MetaMorph Imaging System acquisition software (MDS Analytical Technologies). All images were acquired using an oil immersion objective (63×, 1.25 NA). Filipin was imaged using an A4 filter cube obtained from Chroma Technology Corp.: 360-nm (40-nm bandpass) excitation filter, 365 DCLP (DiChroic Long Pass) filter and 480-nm (40-nm bandpass) emission filter. To minimize photo-bleaching of the filipin signal, a neutral density filter transmitting 1.5% light was used to acquire images. GFP was imaged using a standard FITC filter cube. Fluorescence crossover from one channel to another was measured using single-labeled samples of each probe and was found to be insignificant.

Image Analysis.

Images were analyzed using Metamorph (version 7.0 r4) image analysis software from Molecular Devices (MDS Analytical Technologies). All images were corrected for background before analysis. The average filipin and LSO ratio was calculated as described previously (Pipalia 2006). The LSO ratio was calculated based on low-thresholded region and high-thresholded intensities in the filipin image as described previously (Pipalia 2006).

Cholesterol Efflux Assay.

[$^3$H]cholesteryl ester (CE)-labeled LDL was prepared as described by Krieger, 1986. Briefly, the lipid core of LDL was replaced with [1,2,6,7-$^3$H(N)] cholesteryl oleate (American Radiolabeled Chemicals, Inc.). The specific activity of the labeled LDL was 13.7 cpm/ng of protein. Cells were plated in 24-well plates and incubated for 2 days in F12 medium containing 10% lipoprotein-deficient serum. The cells were labeled by incubation for 4 h in F12 medium containing 0.2% BSA and 10 µg/mL [$^3$H]CE-labeled LDL. At the end of this pulse period, the cells were washed and the medium was replaced with F12/BSA medium containing 50 µg/mL HDL3. At the indicated time points, 100 µL of media was removed and centrifuged for 5 minutes at 14000×g to remove cellular debris, and the radioactivity in this portion of the media was determined by liquid scintillation counting. After the last time point, the cells were washed and the monolayer was dissolved in 250 µL of 0.1N NaOH at room temperature for a minimum of 4 hours. A 100-µL aliquot of the cell lysate was measured, and the percent efflux was calculated as [(media cpm)/(cell+media cpm)]×100. To obtain the value for HDL3-stimulated efflux, the percent efflux in the absence of HDL3 was subtracted from the percent efflux in the presence of acceptor.

Transferrin Efflux Kinetics as a Measure of TR Recycling.

CT60 cells expressing the human TfR (CT60hTfR cells) (Pipalia 2007) were stably transfected with the empty vector pIRES-hrGFPII, pIRES.WT or pIRES.C629S and sorted for high levels of green fluorescence. The cells were maintained in a medium containing G418 (0.5 mg/mL). The resulting stable cell lines were named, respectively, CT60hTfR-VEC, CT60hTfR-WT and CT60hTfR-C629S. The recycling of TfR from endosomes to cell surface was measured as previously described elsewhere (Johnson 2001). Briefly, the cells were plated in 12-well culture dishes in bicarbonate-buffered McCoy's medium. For each experiment and for each cell type, six plates were prepared for six time points (3, 5, 10, 15, 30 and 60 min). Four wells in each plate were pulsed with 5 µg/mL [$^{125}$I]-labeled Tf, and the remaining two wells were pulsed with 5 µg/mL [$^{125}$I]-labeled Tf, with a 200-fold excess of unlabeled Tf to ascertain non-specific binding. All plates were incubated for 30 minutes and washed once with serum-free McCoy's medium, once with acid wash buffer (pH 5.0), and twice with efflux medium. Finally, the efflux medium was added to each plate and incubated for varying time periods. At the end of each chase time, the efflux medium was transferred to collection tubes, and the cells were quickly washed once with the same medium, which was then added to the collection tube. Solubilization solution was added to each well, triturated and transferred to another collection tube. The cells were washed with water, and the washings were added to the solubilization medium. The amount of [$^{125}$I]-labeled Tf was measured for all the efflux and cellular fractions, and the recycling rate of TfR was determined.

BMP Labeling.

Cells seeded in poly-d-lysine-coated coverslip dishes and grown for 2 days were fixed with 3% paraformaldehyde in PBS for 20 minutes at room temperature. Fixed cells were subsequently permeabilized with 0.5% saponin (to ensure complete immunolabeling of BMP within multivesicular lysosomal compartments) and incubated with primary murine anti-BMP antibody (Echelon Biosciences Inc.) for 45 minutes. The cell monolayers were washed three times with PBS and then incubated with Alexa546-labeled goat anti-mouse IgG for 1 hour in the presence of 0.1% saponin. Finally, the cells were washed three times with PBS. Images were acquired using wide-field epifluorescence microscopy at 63× magnification and standard TRITC filters.

Assay for Uptake of LDL-Derived Cholesterol.

Cells were incubated for 2 hours with 5 µg/mL [$^{14}$C]CE-labeled LDL, which was produced using the same method described above for [$^3$H]CE-labeled LDL. Lipids were extracted in hexane:isopropanol (3:2) and subjected to thin-layer chromatography to separate free cholesterol and CE.

Statistics.

Data are presented as mean±SEM of triplicate experiments. Statistical significance was determined using the Student's t-test with unequal variance or one-way ANOVA and the Tukey's multiple comparison test using GraphPad Prism version 4.03 for Windows (GraphPad Software).

Experiments in Acid SMase Restoration

Different primary lysosomal trafficking defects lead to common alterations in lipid trafficking, suggesting cooperative interactions among lysosomal lipids. However, cellular analysis of the functional consequences of this phenomenon is lacking. As a test case, this experiment studied cells with defective Niemann-Pick C1 (NPC1) protein, a cholesterol trafficking protein whose defect gives rise to lysosomal accumulation of cholesterol and other lipids, leading to NPC disease. NPC1 cells also develop a secondary defect in acid sphingomyelinase (SMase) activity despite a normal acid SMase gene (SMPD1). When acid SMase activity was restored to normal levels in NPC1 deficient CHO cells through SMPD1 transfection, there was a dramatic reduction in lysosomal cholesterol. Two other defects, excess lysosomal bis-(monoacylglycerol) phosphate (BMP) and defective transferrin receptor (TfR) recycling, were also markedly improved. To test its relevance in human cells, the acid SMase activity defect in fibroblasts from NPC1 patients was corrected by SMPD1 transfection or acid SMase enzyme replacement. Both treatments resulted in a dramatic reduction in lysosomal cholesterol. These data show that correcting one aspect of a complex lysosomal lipid storage disease can reduce the cellular consequences even if the primary genetic defect is not corrected.

Lysosomal lipid storage diseases (LSDs) are caused by mutations in specific lysosomal hydrolases, trafficking proteins or their co-factors, leading to the accumulation of substrate compounds in late endosome-derived structures called lysosomal storage organelles (LSOs). The primary cellular abnormality often perturbs the trafficking of multiple lipids and proteins, which probably contributes to the overall pathophysiology of the disease. These trafficking abnormalities and other secondary defects may, in turn, amplify the cellular pathophysiology triggered by the primary mutation. Identification and functional assessment of these secondary defects may therefore offer new therapeutic opportunities even if the primary genetic defect is not corrected.

To test this concept, this experiment studied cells lacking the late endosomal protein Niemann-Pick C1 (NPC1). NPC1, a membrane protein, co-operates in some manner with NPC2, a cholesterol-binding protein in the lumen of endosomes, to transfer endocytosed cholesterol from the lumen to the membrane of late endosomes. The cholesterol is then transferred from the endosomal membrane to peripheral cellular sites through one or more processes that are still under intense investigation. Cells lacking functional NPC1 and NPC2 show defects in the transport of cholesterol and other lipids from late endosomes to peripheral sites in the cell. Mutations in NPC1 and NPC2 give rise to Niemann-Pick C disease, which is characterized by hepatosplenomegaly, liver disease and potentially devastating neurological disease.

At the cellular level, cells with defective NPC1 accumulate cholesterol along with excess sphingomyelin (SM), glycosphingolipids and bis-(monoacylglycerol) phosphate (BMP). It remains unclear whether the primary defect in NPC1 mutants is directly associated with cholesterol transport or whether the cholesterol accumulation is secondary to accumulation of other lipids, which associate with cholesterol in membranes. In this regard, it is noteworthy that cholesterol-enriched NPC cells and tissues from NPC1-mutant mice and humans have a secondary, post-translational defect in the activity of a lysosomal enzyme, acid sphingomyelinase (SMase). This alteration in acid SMase activity can be observed in wild-type (WT) cells with increased levels of late endosomal cholesterol resulting from incubation with low-density lipoprotein (LDL) and progesterone. Thus, elevated cholesterol and elevated SM appear to be synergistically linked in a positive feedback loop.

Although the mechanism of suppression of acid SMase activity by cholesterol is not known, it can be surmised that this defect might have functional significance. In particular, primary deficiency of acid SMase (types A and B Niemann-Pick disease) leads to cellular defects and disease characteristics that share certain features with NPC disease. For example, both types A/B and type C Niemann-Pick disease patients are known to have hepatosplenomegaly and neurological abnormalities, and it has previously been shown that macrophages lacking acid SMase have defective late endosomal cholesterol trafficking (A. R. Leventhal, et al., J. Biol. Chem., 2001, 276:44976-44983). This study, therefore, aimed to better understand whether some of the trafficking defects in cells with NPC disease could be corrected by correcting the secondary enzymatic activity defect (i.e. acid SMase). The cell culture data presented in this study certainly support this initially formulated concept.

Restoration of Acid SMase Activity in NPC1-Defective CT60 Cells by Transfection with WT and/or C629S Acid SMase (SMPD1) cDNA As a model of NPC1 cells, this experiment studied CT60 cells, which are NPC1-deficient CHO cells derived from a parental line called 25RA (Cadigan 1990; Watari 1999). CT60 cells were observed to exhibit much lower acid SMase activity than the 25RA cells (FIG. 22A) despite no decrease in acid SMase protein. In preparation for studies addressing the role of defective acid SMase activity in CT60 cells, this experiment sought to restore enzymatic activity in these cells through human acid SMase gene (SMPD1) transfection. For this purpose, this experiment used two cDNA constructs: WT SMPD1 cDNA and a site-directed mutant cDNA (C629S SMPD1), which encodes acid SMase in which C-terminal Cys-629 of the enzyme is replaced with Ser. Qiu et al. (Qiu 2003) proposed that C629S acid SMase mimics a naturally occurring processed form of the enzyme that has increased enzymatic activity.

Figure 22A:
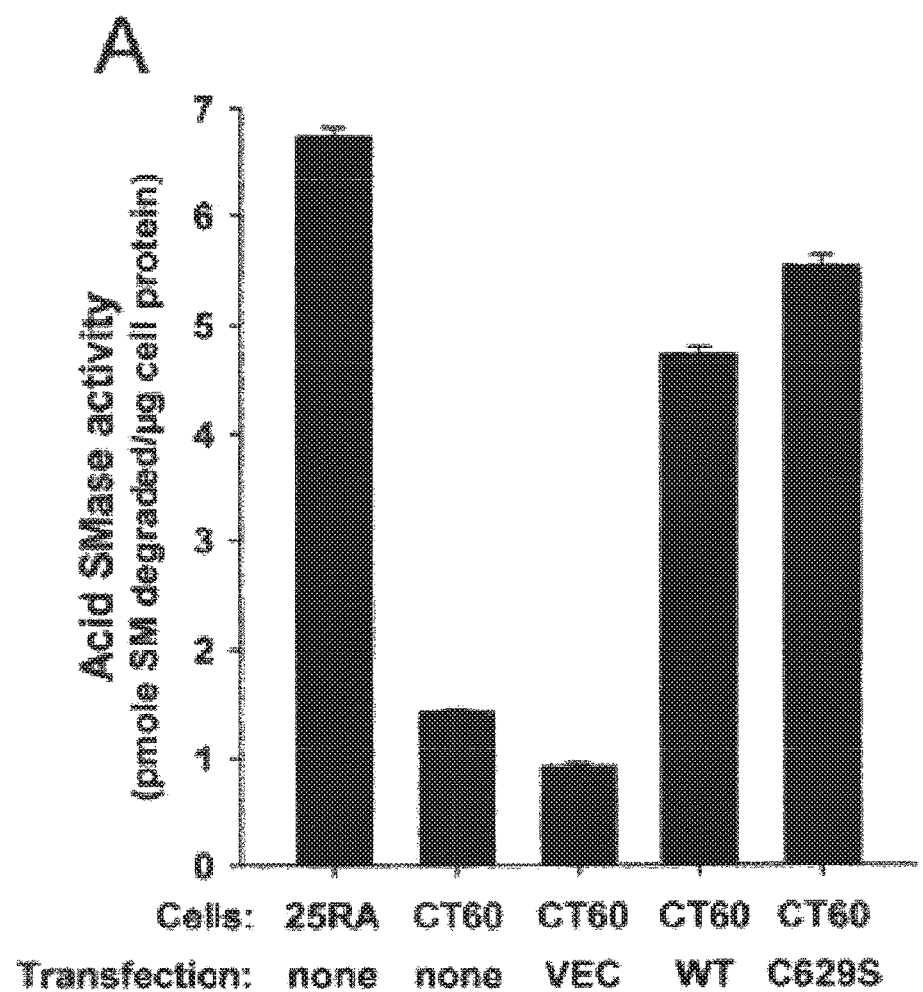
FIGS. 22 A-F. Decrease in cholesterol accumulation in LSOs by restoration of acid SMase activity in CT60 cells. A) Acid SMase activity plot: CT60 cells were transfected with empty vector (VEC) or with vector containing either the WT or the C629S SMPD1 cDNA constructs. Two days later, extracts of these cells and non-transfected 25RA and CT60 cells were assayed for acid SMase activity. The activity levels in CT60-WT and CT60-C629S cells were significantly different from those in non-transfected CT60 cells and CT60-VEC cells (p<0.0001). B) Micrographs: the five cell groups described in (A) were fixed and stained with filipin. The images are displayed with the same gray scale range. Scale bar, 20 µm. C) LSO filipin intensity plot: quantification of filipin fluorescence in the LSOs, and D) in whole cells. Each bar in the data quantification represents the average of 30 images from two independent experiments±SEM. The CT60-WT and CT60-C629S values were significantly different from the CT60 and CT60-VEC values (p<0.0001). NB: The 25RA and CT60 cells used in this experiment are the same ones used in FIG. 26, i.e. they express the hTfR. However, they have the same level of cholesterol accumulation in LSOs and the same response to acid SMase restoration as cells not expressing the TfR (data not shown). E) Plot of relative cellular cholesterol mass: free cholesterol levels in each of the five cell groups described in (A) were assayed by gas chromatography. Each bar represents an average of four samples from two independent experiments and is normalized to CT60-VEC value, which was 45.7±1.7 µg cholesterol/mg cell protein. The CT60-WT and CT60-C629S values were significantly different from the CT60 and CT60-VEC values (p<0.0001). F) Monolayers of the five groups of cells described above were incubated for 2 hours with 5 µg/mL LDL reconstituted with [$^{14}$C] cholesteryl ester (CE). Lipid extracts of the cells were then fractionated by thin-layer chromatography, and the areas of the plate corresponding to cholesterol and CE, which accounted for all of the radioactivity, were scraped and counted for [$^{14}$C]cpm. [$^{14}$C]cholesterol represents hydrolyzed LDL-CE in the cells, and [$^{14}$C]CE represents either unhydrolyzed LDL-CE or hydrolyzed LDL-cholesterol that was re-esterified in the cells to CE. The data shown are derived from the total LDL-derived cholesterol in the cells (free cholesterol+CE) and are mean of 5 values±SEM. The values for cellular-free cholesterol derived from LDL were similar among all the five cell types: 1.92, 1.88, 1.93, 2.05, 1.72 pmol/µg cell protein, respectively. None of the differences in total or free LDL-derived cellular cholesterol among the five groups of cells reached statistical significance.

As shown in FIG. 22A, cells transfected with either form of the cDNA demonstrated restoration of acid SMase activity to a level similar to that in the parental 25RA cells, whereas those transfected with a construct not containing the SMPD1 cDNA (VEC) had a level of acid SMase activity similar to that in non-transfected CT60 cells. Despite this initial hypothesis on the potential functional consequences of acid SMase in NPC1 cells, it was predicted that the overall quantitative effect of the NPC1 mutation and subsequent acid SMase correction on total cellular SM mass would be relatively modest, because only the pool of SM in late endosomes/lysosomes should be accessible to this enzyme. The observation was made that total cellular SM mass was 20% higher in CT60 and CT60 cells transfected with empty vector (CT60-VEC) compared with that in 25RA cells ($p<0.05$), and transfection of CT60 cells with WT or C629S SMPD1 cDNA lowered SM mass close to the value in 25RA cells (data not shown). In summary, it was found that WT levels of acid SMase activity can be functionally restored in CT60 cells through transfection with either WT or C629S SMPD1 cDNA, thus allowing an assessment of whether this restoration can correct trafficking defects in these cells.

Restoration of Acid SMase Activity in CT60 Cells Leads to a Decrease in Cholesterol Accumulation in LSOs Previous mechanistic studies have shown that enrichment of membranes with SM can disturb cholesterol trafficking because of SM-cholesterol interactions, perturbations in membrane biophysical properties and defective interaction of cholesterol transport proteins with SM-rich membranes (Cheruku 2006; Levanthal 2001; Ridgway 2000; Megha 2004). This experiment, therefore, considered whether it would be possible to correct some of the trafficking defects in NPC cells by restoring normal levels of acid SMase activity. To test this hypothesis, the experiment quantified LSO filipin fluorescence in CT60 cells stably transfected with the cDNA constructs, as described in Materials and Methods. Shown in FIG. 22B (a-c) is the expected increase in LSO filipin fluorescence in CT60 or CT60-VEC cells compared with that in 25RA cells.

Figure 22B:
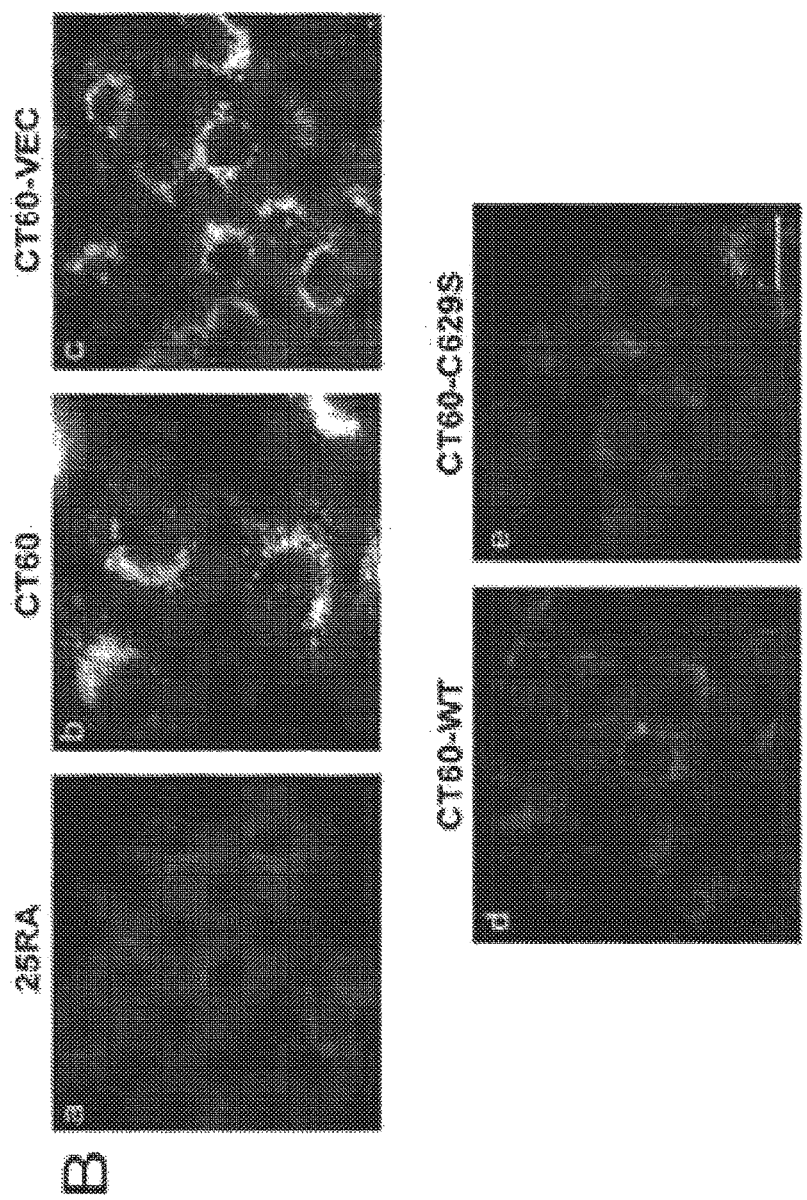
Figure 22C:
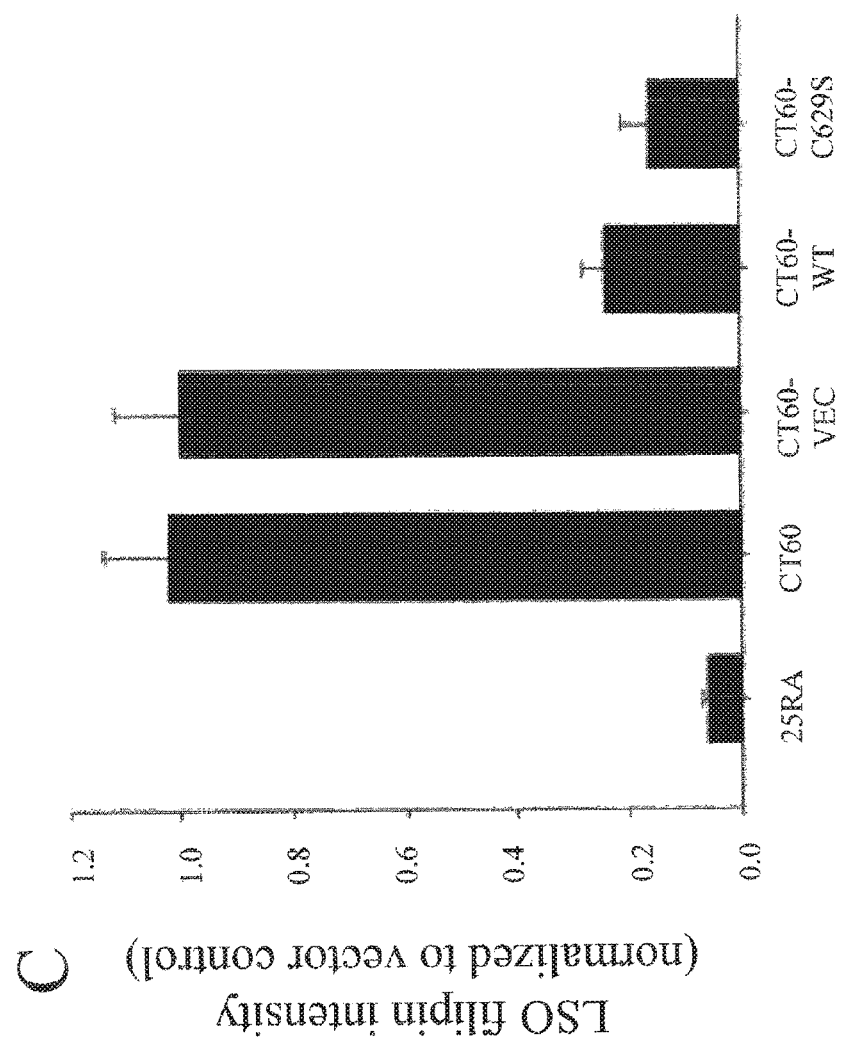
Figure 22D:
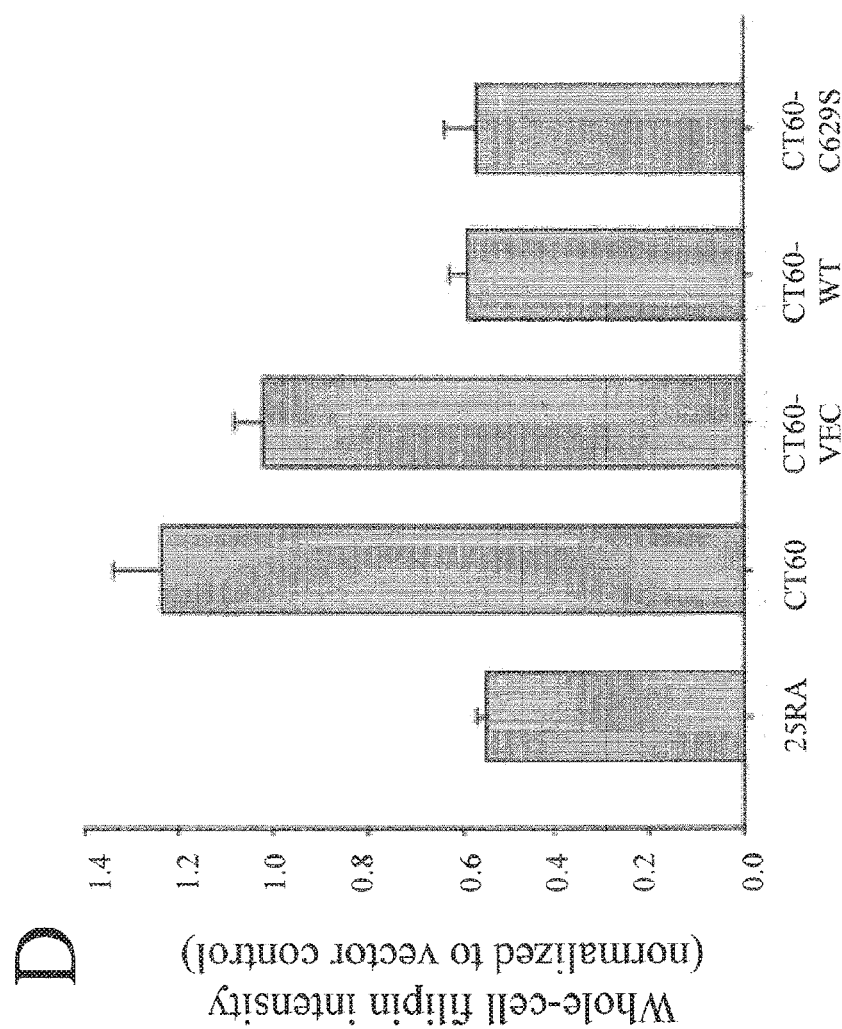
Figure 22E:
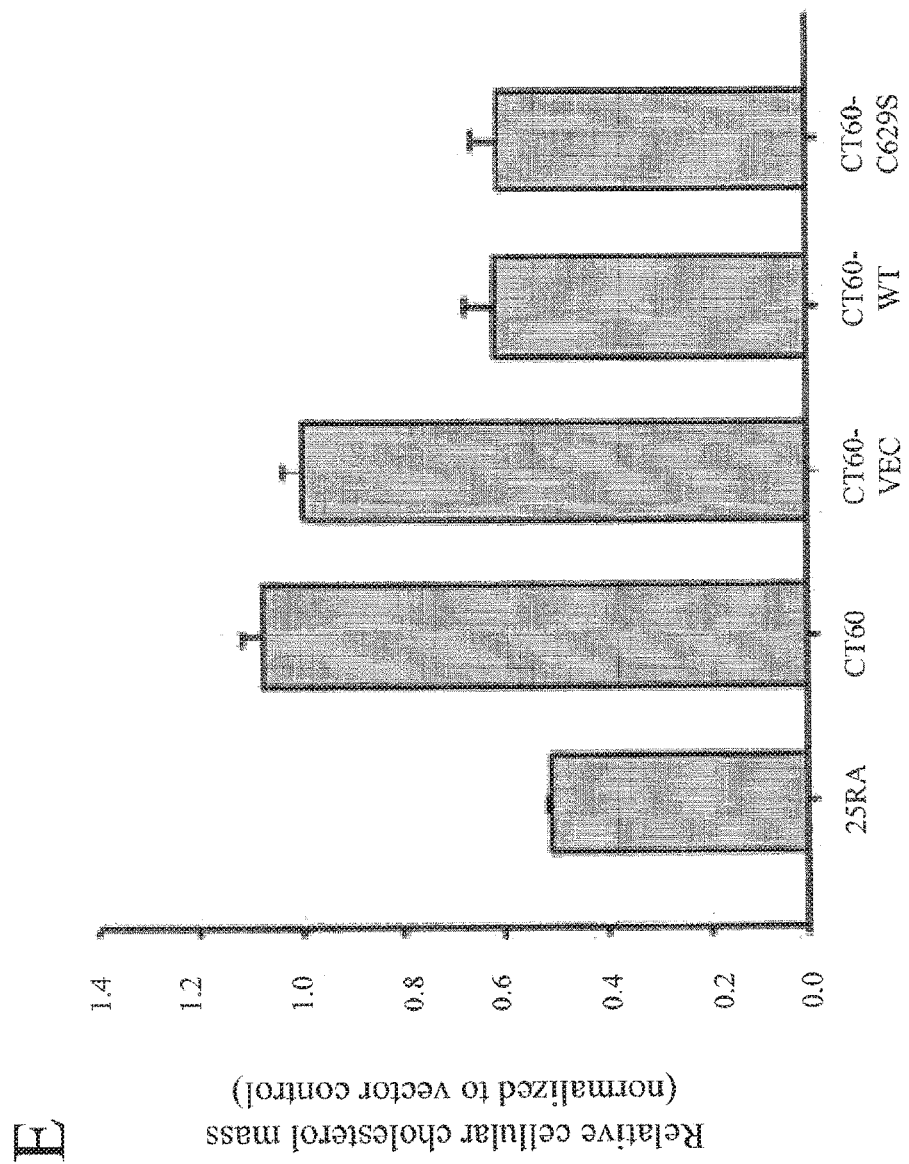
Figure 22F:
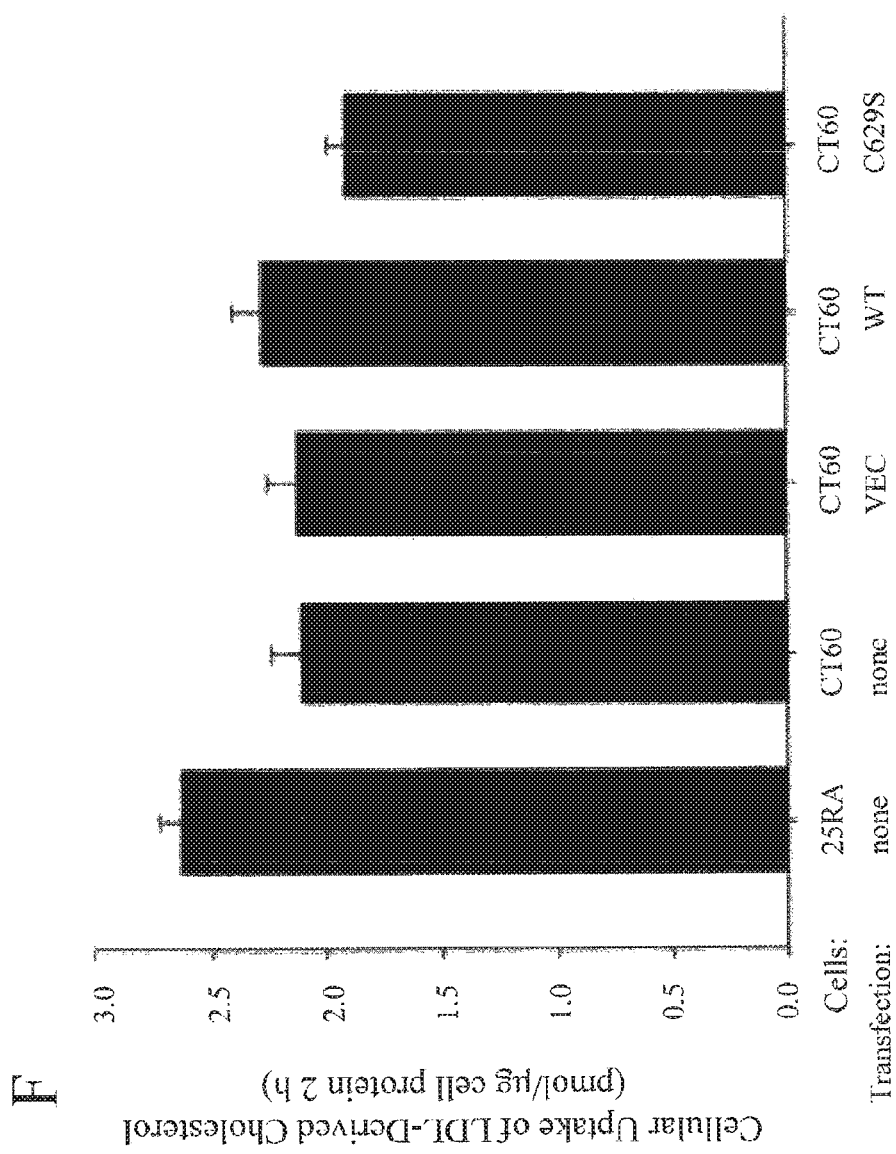

Most importantly, the data show a striking loss of LSO filipin fluorescence in the cells expressing WT or C629S acid SMase (FIG. 22B, d and e therein). Quantification of LSO and whole-cell fluorescence confirmed these observations (FIG. 22 C,D). It has previously been shown that estimation of cholesterol levels using filipin assay is comparable with free cholesterol levels quantified by biochemical methods (Qin 2006; Bartz 2009). To confirm these filipin results, this experiment also estimated the free cholesterol using gas chromatography (FIG. 22E). A previous report showed that the free cholesterol in control 25RA cells is only ~40% compared with that of CT60 cells (Maguire 2005). This experiment obtained similar data, as shown by the ~45-50% decrease in free cholesterol content in control 25RA cells compared with that in CT60 or CT60-VEC cells. In agreement with these whole-cell filipin results, it was found that the level of free cholesterol was markedly decreased in CT60-WT and CT60-C629S cells and approached the level found in 25RA cells. It is noted that the loss of LSO filipin fluorescence in the SMPD1-transfected cells could not be explained by a decreased uptake of LDL-cholesterol, which was similar among all five cell types (FIG. 22E). Thus, correcting the acid SMase activity defect in NPC1-mutant CT60 cells has a dramatic effect on improving a fundamental characteristic of these cells, namely, cholesterol accumulation in LSOs.

Cholesterol leaving LSOs in acid SMase-transfected CT60 cells might accumulate in other cellular membranes, become esterified by acyl-CoA:cholesterol acyltransferase and/or get effluxed from the cells. The fact that whole-cell filipin fluorescence is lower in the SMPD1-transfected cells and becomes comparable with that in the parental 25RA cells suggests that accumulation of high concentrations of unesterified cholesterol in non-LSO sites is not a major fate of the cholesterol.

Figure 23A:
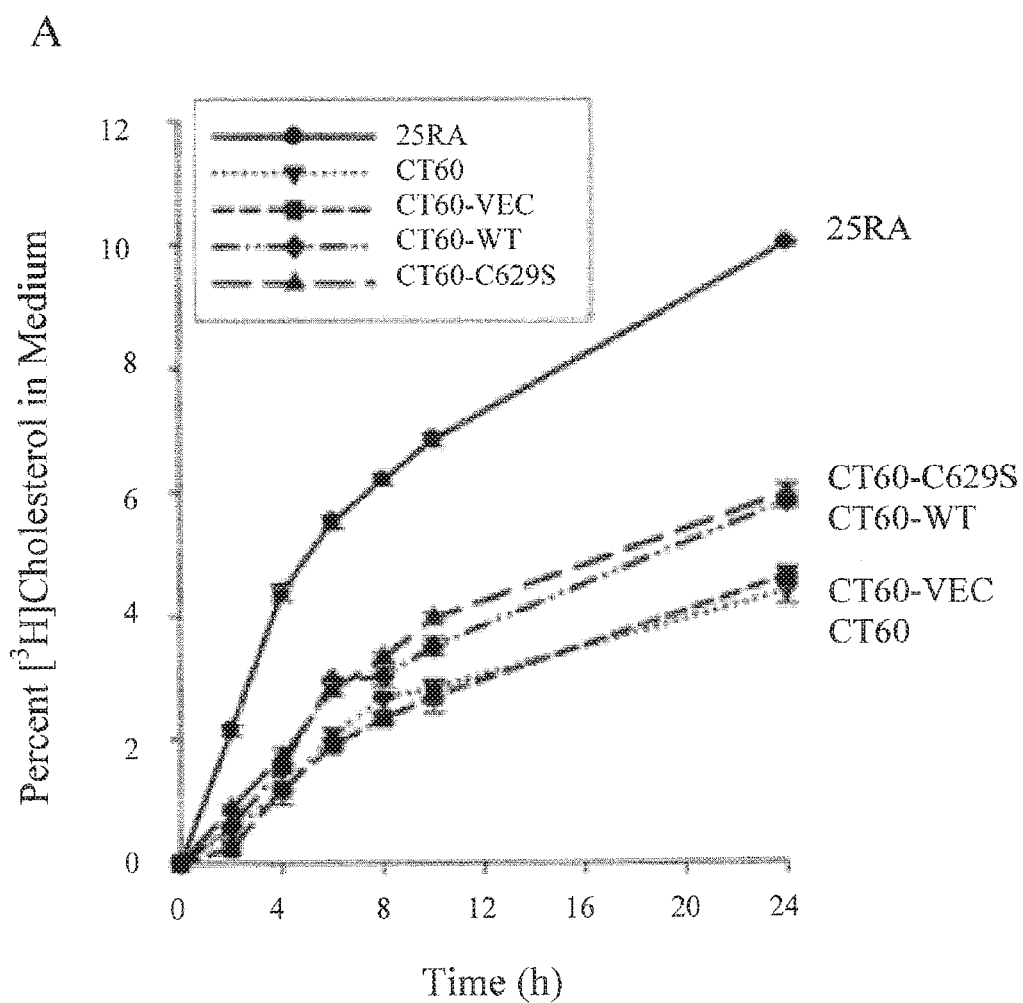
FIG. 23 A, B. Partial correction of efflux of LDL-derived [$^3$H]cholesterol from CT60 cells by restoration of acid SMase activity. A) Monolayers of 25RA, CT60, CT60-VEC, CT60-WT and CT60-C629S were incubated for 4 h in serum-free medium containing 10 µg/mL [$^3$H]CE-labeled LDL. The cells were then rinsed and incubated with fresh medium containing 50 µg/mL HDL3 for the indicated times. Tritium radioactivity in the media and cells was measured to calculate the percent [$^3$H]cholesterol in the medium. The values for CT60-WT and CT60-C629S cells were significantly different from the other three values at 24 h (p<0.005). B) The bottom graph shows acid SMase activity in the five groups of cells at 0, 8 and 24 hours after incubation in conditions nearly identical to those in (A), except that cells were incubated with unlabeled LDL. The values for CT60-WT and CT60-C629S cells were significantly different from that of CT60 and CT60-VEC (p<0.005).
Figure 23B:
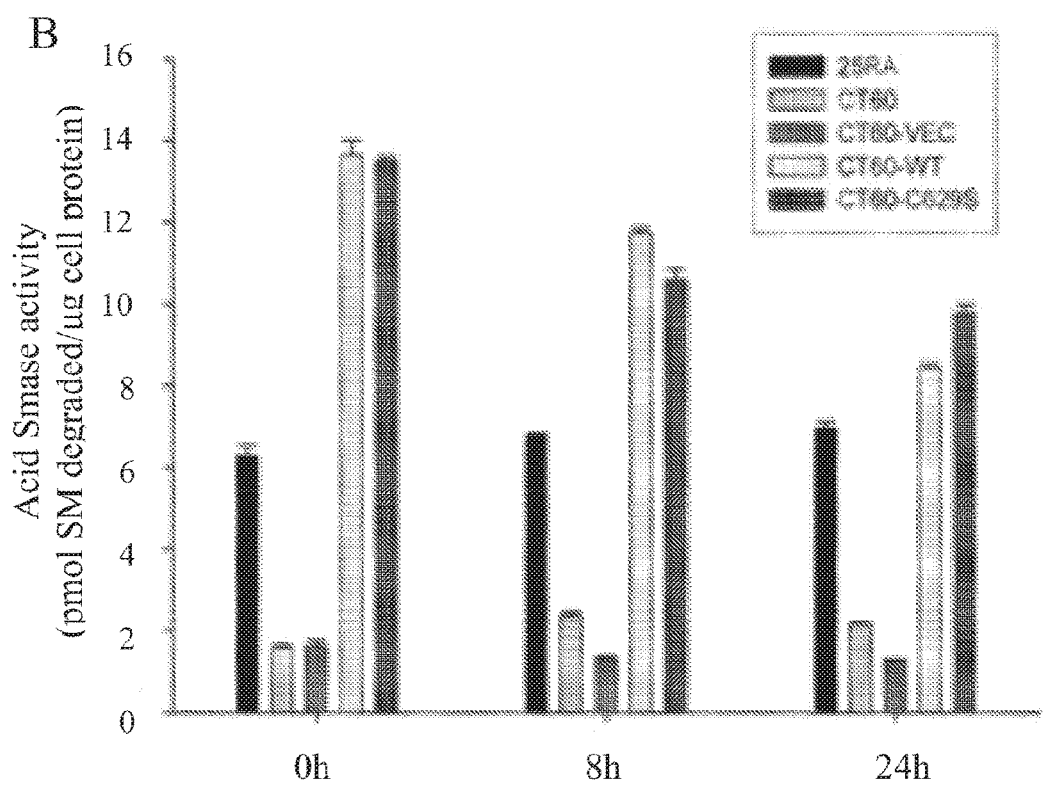

Moreover, when cells were incubated with [$^3$H]cholesterol-labeled LDL for 4 hours and then chased for up to 24 hours, an increase in esterification was not observed in CT60 cells transfected with SMPD1 versus CT60-VEC cells (data not shown), thus suggesting that trafficking to and esterification by ACAT in the endoplasmic reticulum (ER) are also not a major fate of the acid SMase-mediated released LSO-derived cholesterol. However, efflux of the LDL-derived [$^3$H]cholesterol, which is markedly decreased in CT60 cells, was restored by 20% after 24 h in SMPD1-transfected cells (FIG. 23A). The corresponding acid SMase activity measurements are shown in FIG. 23B. These data suggest that a portion of the cholesterol exiting the LSO in acid SMase-restored CT60 cells is effluxed, with the rest probably being distributed diffusely to other cellular membranes.

Figure 24A:
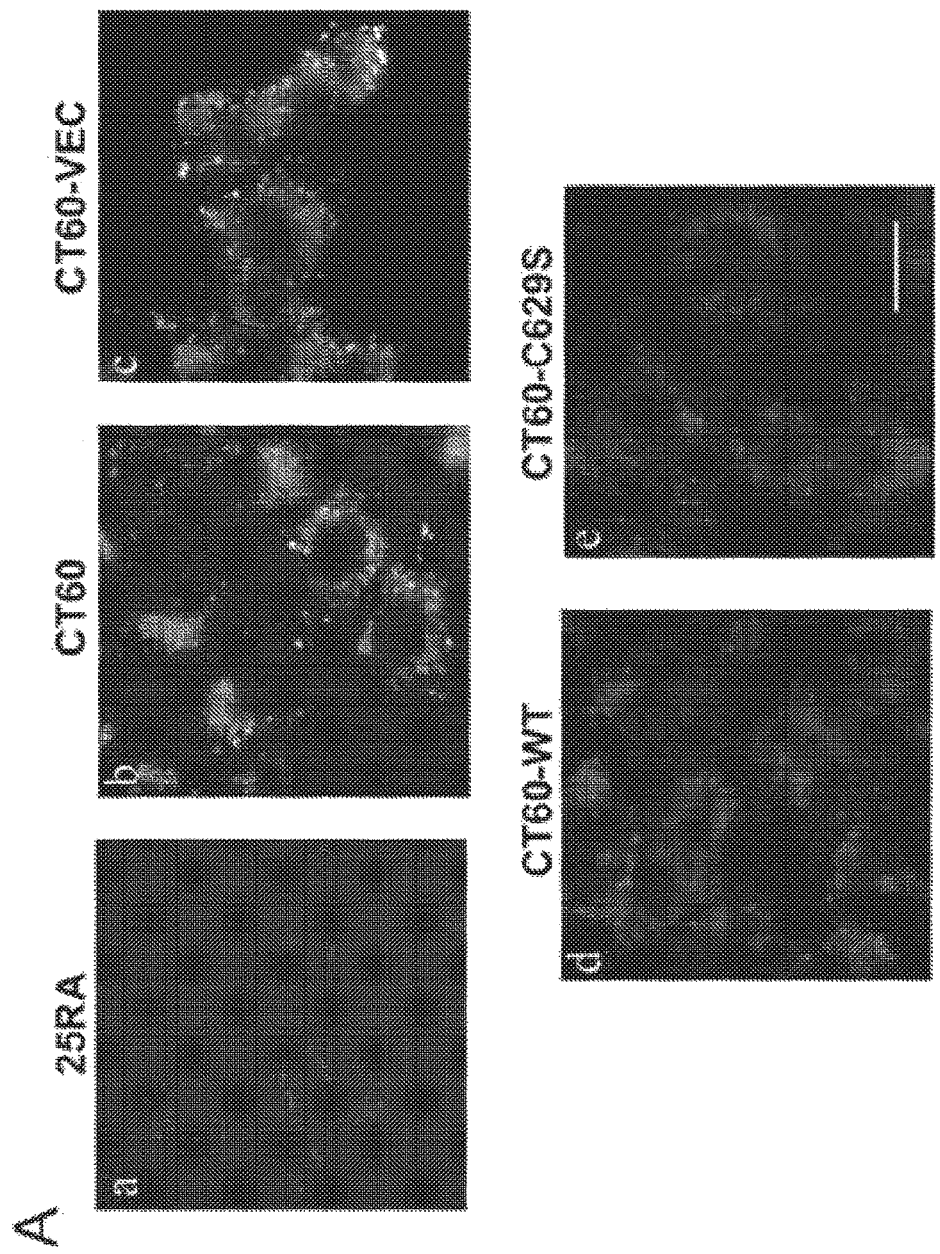
FIG. 24 A, B. Decrease in BMP accumulation in CT60 cells by restoration of acid SMase activity. A) Anti-BMP immunofluorescence in 25RA, CT60, CT60-VEC, CT60-WT and CT60-C629S cells. Scale bar, 20 µm. B) Quantitation of anti-BMP immunofluorescence intensity. Each bar in the data quantification represents the average of 20 images from two independent experiments±SEM. The values for CT60-WT and CT60-C629S cells were significantly different from that of CT60 and CT60-VEC cells (p<0.01). NB: As in FIG. 1, the cells used here express the hTfR, but they have the same level of BMP accumulation in LSOs and the same response to acid SMase restoration as the cells not expressing the TfR (data not shown).
Figure 24B:
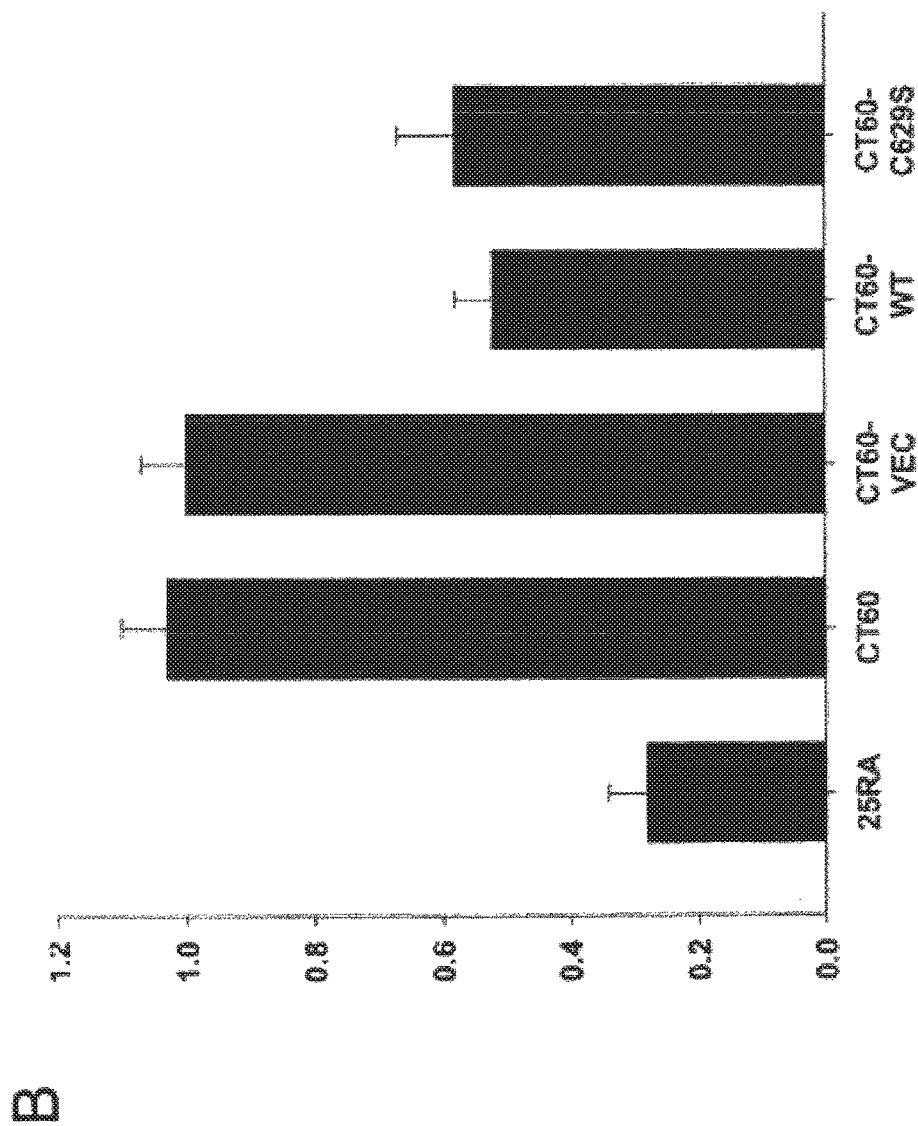

Restoration of Acid SMase Activity in CT60 Cells Leads to a Decrease in BMP Accumulation and an Increase in the Half-Life of Transferrin Receptor (TfR) Recycling The hydrophobic, acidic phospholipid, BMP, also called lysobisphosphatidic acid (LBPA), has been shown to accumulate within NPC1 cells (Pipalia 2007; Salvioli 2004). To test the possibility that restoration of acid SMase activity could have a broad corrective effect on NPC cells, this experiment investigated whether BMP accumulation was also diminished in SMPD1-transfected CT60 cells. Consistent with the data cited above, CT60 cells accumulated much more BMP than 25RA cells (FIG. 24A, a-b therein). Cells transfected with non-SMPD1-containing control vector also accumulated large amounts of BMP (FIG. 24A, c therein). In contrast, cells transfected with WT or C629S SMPD1 had greatly diminished accumulation of BMP (FIG. 24A, d-e therein). The quantified data are shown in FIG. 24B. Thus, it has been shown that defective BMP accumulation, like defective cholesterol accumulation, can be partially corrected by restoration of acid SMase activity in NPC1-deficient cells.

Figure 25:
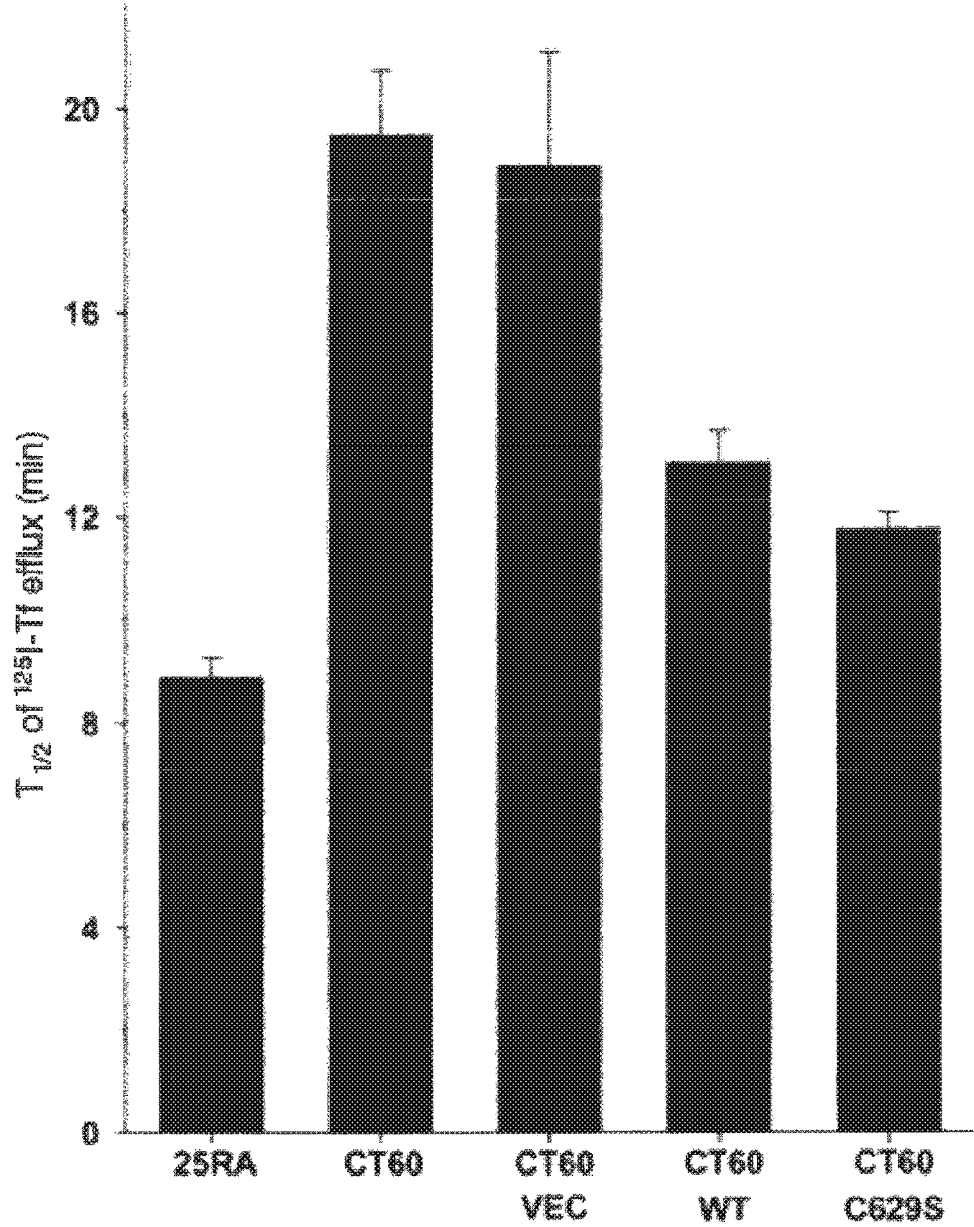
FIG. 25. Plot showing that recycling of the transferrin receptor in CT60 cells is improved by restoration of acid SMase activity. The efflux kinetics of [$^{125}$I]-transferrin was measured in 25RA, CT60, CT60VEC, CT60-WT and CT60-C629S cells expressing the hTfR, as described in Materials and Methods. The values for CT60-WT and CT60-C629S cells were significantly different from that of CT60 and CT60-VEC cells (p<0.05).

It was previously reported that the recycling rates of TfRs are decreased in NPC1 cells compared with that in normal fibroblasts (Pipalia 2007; Choudhury 2004). Using 25RA and CT60 cells that express the human transferrin receptor (hTfR) (Pipalia 2007), this experiment assessed TfR cycling in the control and SMPD1 transfected cells and determined whether the decrease in recycling in NPC1-deficient cells could be corrected by restoration of acid SMase activity. To assay TfR recycling, the cells were incubated with [$^{125}$I]Tf to achieve steady-state occupancy of the TfR with Tf. The Tf bound to the cell surface was then removed, and the release of internal Tf from the cells was monitored as a function of time. The [$^{125}$I]Tf released into the medium reflects the return of TfR from endosomes to plasma membrane. The fraction of [$^{125}$I]Tf remaining in the cells decreases as a function of time as a first-order process, and therefore the decrease in cell-associated [$^{125}$I]Tf fits an exponential decay curve. It was previously reported that the Tf efflux kinetics yielded a $t_{1/2}$ of 11.3 minutes for 25RA cells and 21.7 min for CT60 cells (Pipalia 2007), which is consistent with the instant current results (FIG. 25). As expected, the TfR recycling defect persisted in CT60-VEC cells. In contrast, cells expressing either WT or C629S acid SMase displayed a marked improvement in Tf trafficking, showing a $t_{1/2}$ value close to that of 25RA cells. Thus, it has been shown that the defect in TfR recycling in CT60 cells, similar to the defect in LSO cholesterol and BMP accumulation, can be substantially corrected by restoration of acid SMase activity.

Figure 26A:
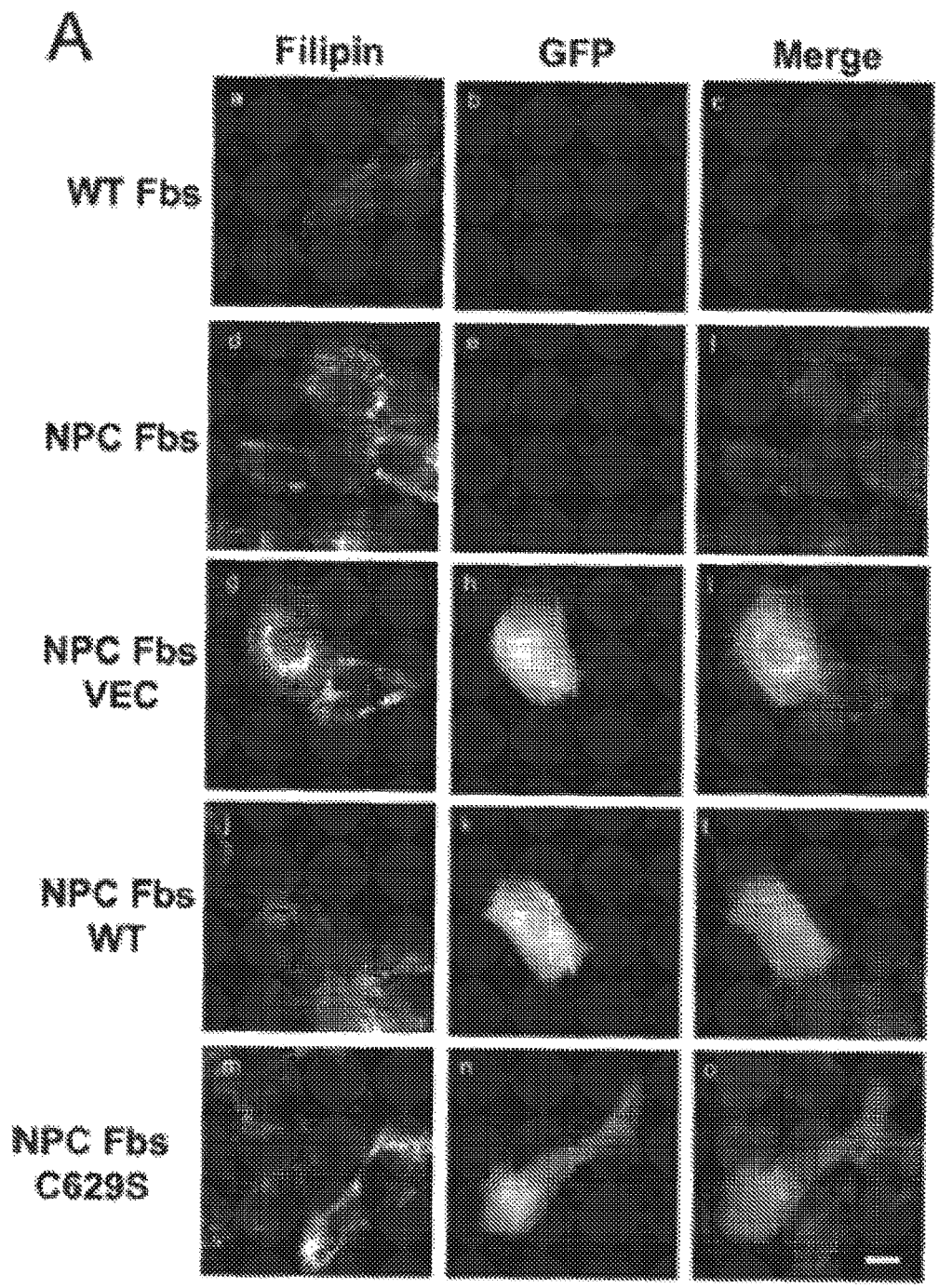
FIG. 26 A, B. Decrease in cholesterol accumulation in LSOs by genetic restoration of acid SMase activity in human fibroblasts. A) Human WT (GM05659) and NPC (GM03123) Fbs were left untransfected or were transiently transfected with empty GFP-expressing vector (VEC) or with GFP-vector containing either WT or C629S SMPD1 cDNA constructs. Two days later, the cells were washed with PBS, fixed and stained with filipin. Standard UV and FITC filters were used for filipin imaging (all cells) or GFP imaging (transfected cells), respectively. The displayed filipin images and GFP images are on the same gray scale range, respectively. Scale bar, 30 µm. B) The bar graph shows LSO ratio values normalized to the NPC-VEC values (average of 20-30 images from three independent experiments±SEM). The values for NPC and NPC-VEC fibroblasts were significantly different from those for NPC-WT and NPC-C629S fibroblasts ($p<0.0001$).
Figure 26B:
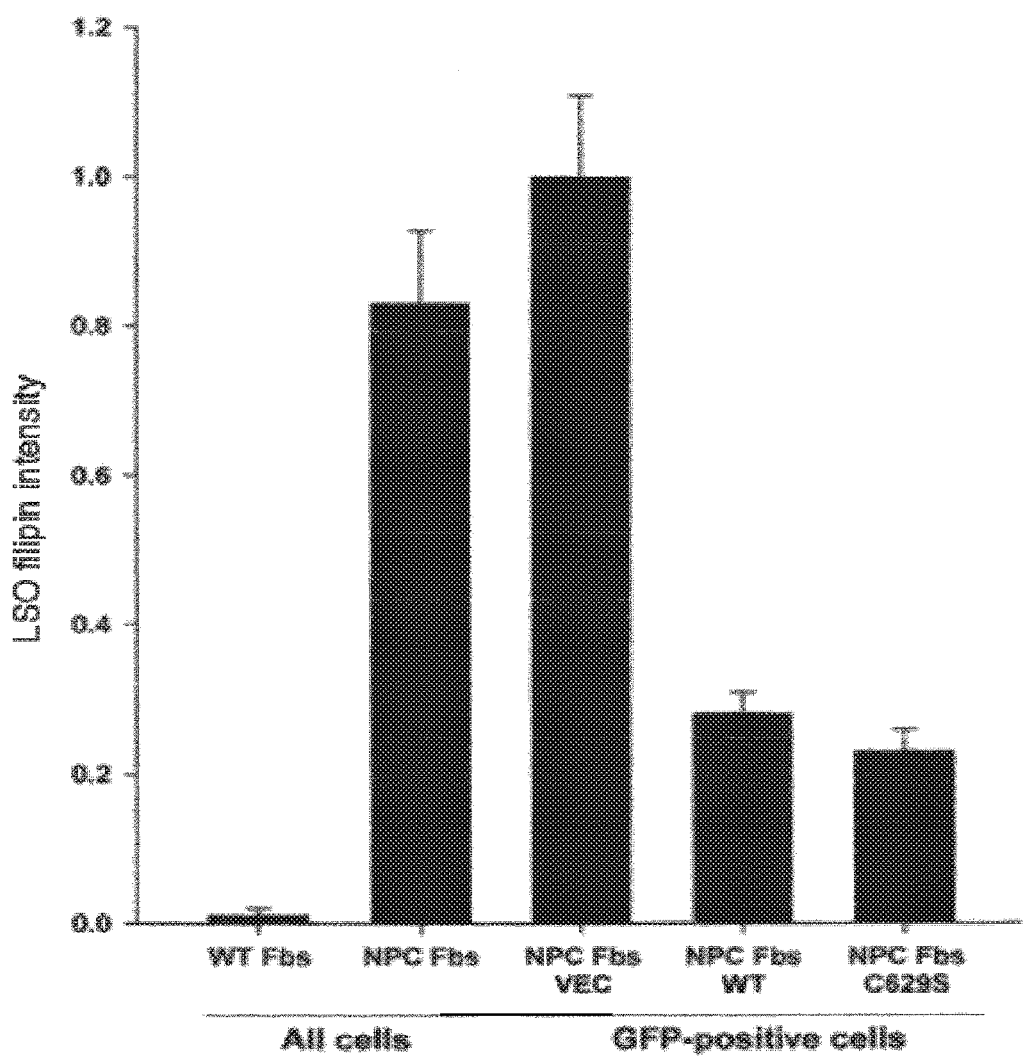

Genetic Restoration of Acid SMase Activity in Human NPC1 Cells Leads to a Dramatic Decrease in Cholesterol Accumulation in LSOs To the extent that the secondary defect in acid SMase activity observed in NPC1 cells and in tissues from NPC mice and humans contributes to one or more aspects of NPC disease pathology (see Discussion), the data shown herein raise the possibility that correction of this enzyme activity defect may be clinically beneficial. Moreover, because lysosomal pH is the same in control and NPC1 fibroblasts (NPC Fbs) (Lloyd-Evans 2008), the loss of acid SMase activity was not due to abnormal lysosomal pH. To explore this concept at the cellular level, this experiment conducted a series of acid SMase restoration experiments using skin fibroblasts isolated from a compound heterozygous child with the late infantile form of NPC1 disease. NPC1 expression in these cells is undetectable by immunoblot analysis, and the cells display a severe defect in trafficking lipoprotein-derived cholesterol (Yamamoto 2000; Pentchev 1985). As described previously (Maziere 1982), and verified in this experiment (below), these fibroblasts also have a partial defect in acid SMase activity. Filipin staining of the cells revealed, as expected, intense LSO staining, indicative of LSO cholesterol accumulation (FIG. 26A, a-f therein, and first two bars (from left) of plot shown in FIG. 26B). Cells transfected with the empty vector, which contained a GFP expression construct, showed marked filipin staining that was indistinguishable from untransfected cells (FIG. 26A, g-i therein, and third bar of plot shown in FIG. 26B). When the cells were transfected with either the WT or the C629S SMPD1 cDNA construct, LSO filipin staining was dramatically reduced in cells that were successfully transfected (green) but not in cells that were not successfully transfected (non-green), which acted as an internal negative control (FIG. 26A, j-o therein, and last two bars of plot shown in FIG. 26B).

Figure 27A:
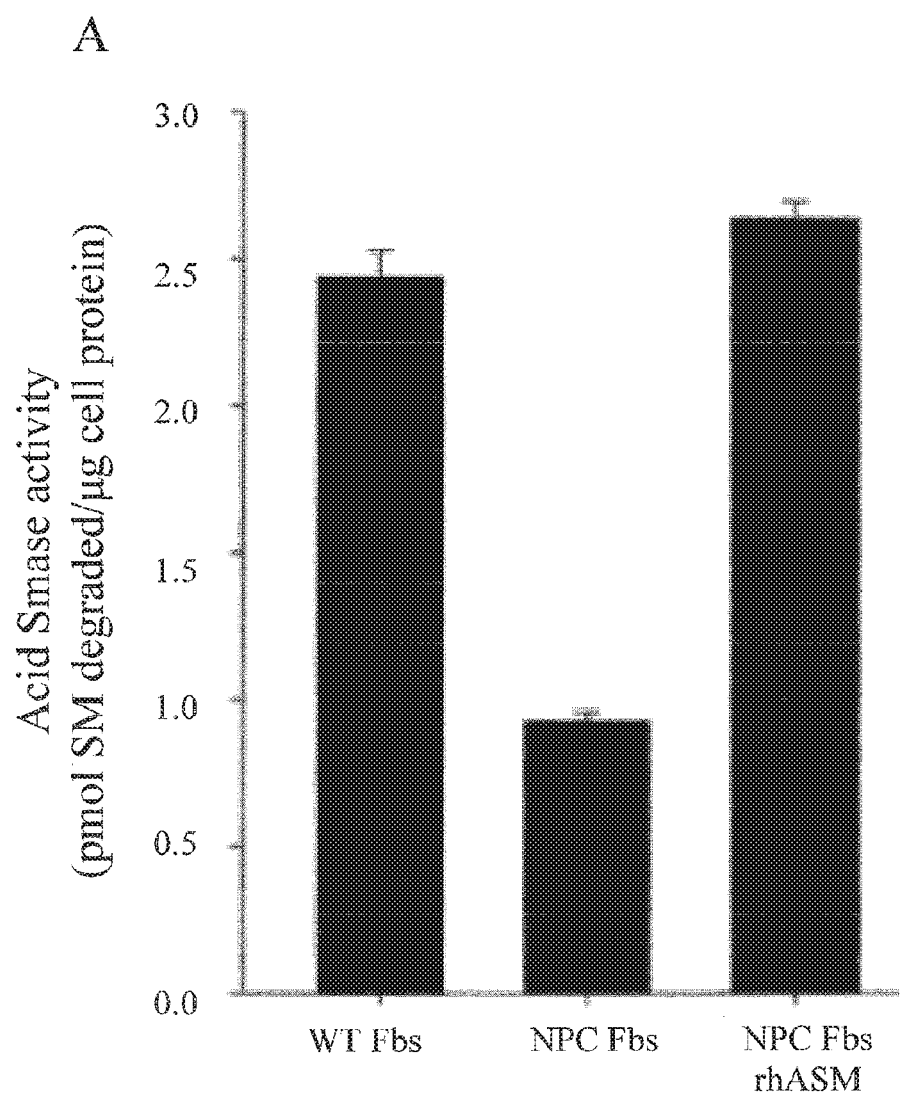
FIGS. 27 A-C. Graph showing the effect of SMase restoration on human NPC1 cells (exogenous acid SMase decreases cholesterol accumulation in LSOs in human NPC fibroblasts). Parallel sets of human WT (GM05659) and NPC (GM03123) Fbs were incubated in medium alone or, in the case of the NPC fibroblasts, medium containing 3 µg/mL recombinant human acid SMase (rhASM). Two days later, the cells were washed thoroughly with PBS and either lysed and assayed for acid SMase activity (A), or fixed and stained with filipin for imaging and quantification (B). The images are displayed with the same gray scale range. Scale bar, 15 µm. The quantified data in the bar graph represent LSO ratios normalized to the WT Fb values (average of 60-66 images from three independent experiments±SEM). C) Another human NPC Fbs (GM18453) was incubated with 3 µg/mL rhASM for 24 h, unlike 48 h in NPC1 (GM03123). Quantified data shown in bar chart are the normalized LSO ratios (normalized to untreated NPC Fbs) in the presence and absence of recombinant enzyme. Data represents an average from two independent experiments and 30-36 images±SEM, $p<0.0001$. The values for NPC fibroblasts in panels A, B and C were significantly different from both the WT Fbs and the NPC fibroblasts treated with rhASM ($p<0.0001$).
Figure 27B:
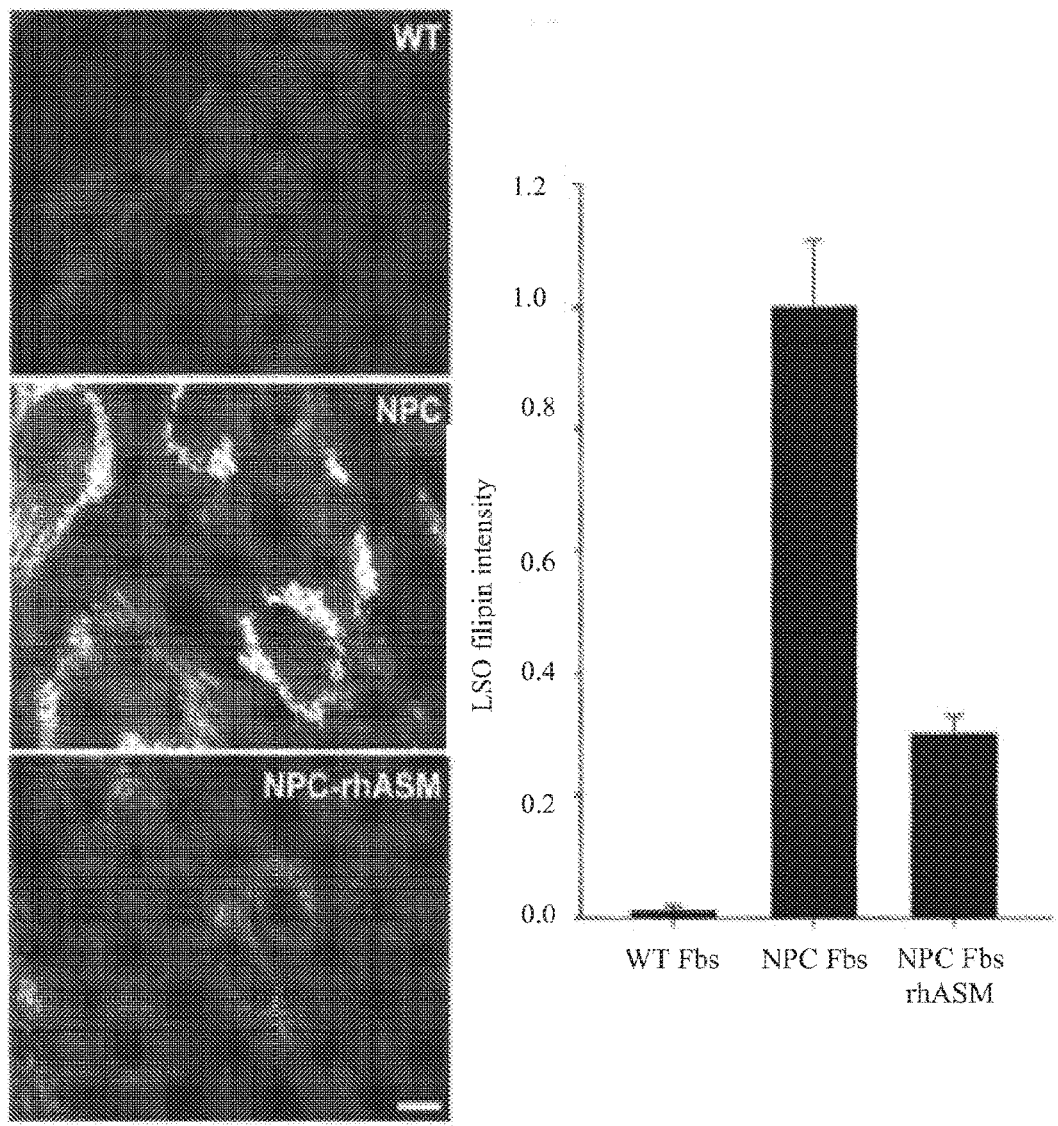
Figure 27C:
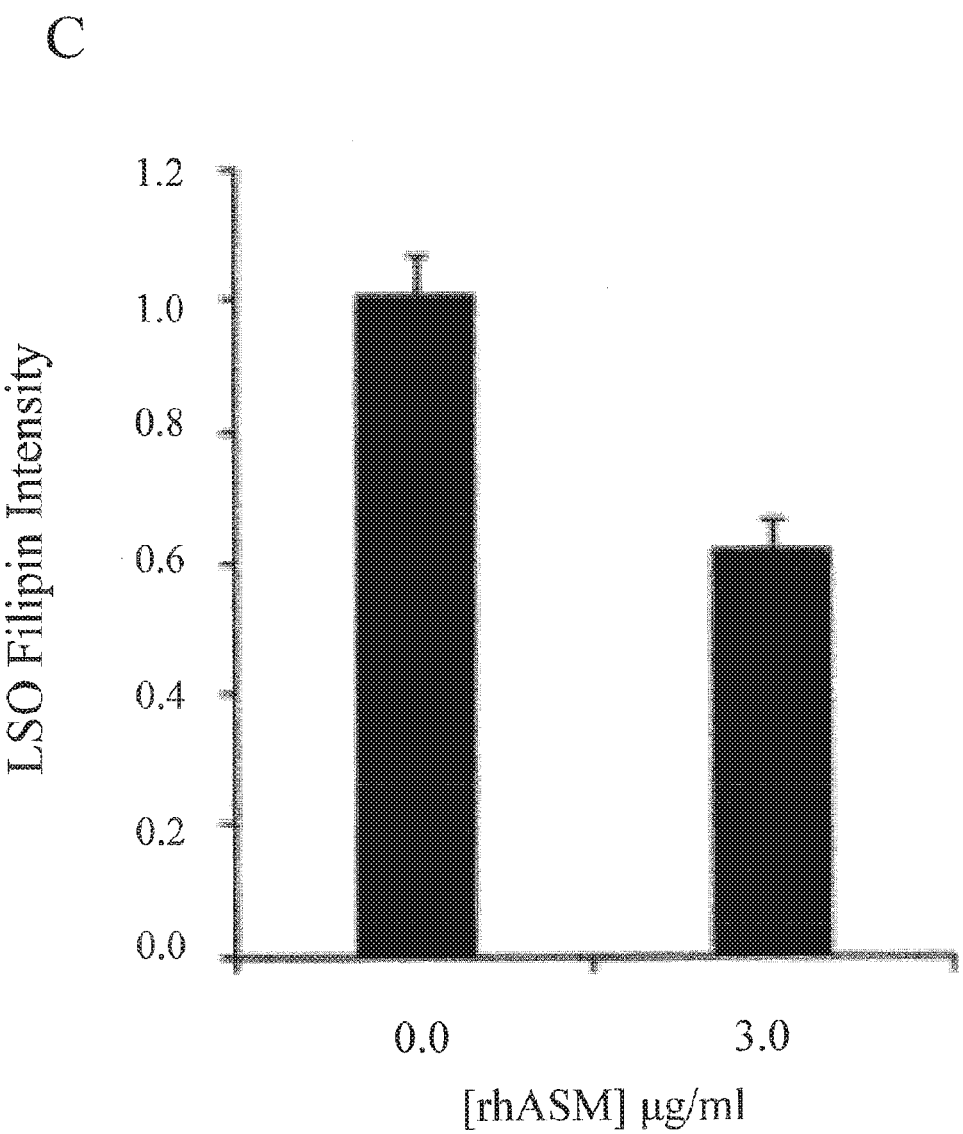

Restoration of Acid SMase Activity in Human NPC1 Cells by Exogenous Acid SMase Also Leads to a Decrease in Cholesterol Accumulation in LSOs Lysosomal enzyme defects, unlike defects in lysosomal membrane proteins such as NPC1, can be corrected both in vitro and in vivo using enzyme replacement therapy (Neufeld 1980; Brady 2006). Indeed, this approach is currently being tested in humans with primary acid SMase deficiency (Schuchman 2007). This strategy takes advantage of the fact that cells can endocytose lysosomal enzymes and deliver them in a functionally active state to late endosomes and lysosomes (Neufeld 1980). To apply this concept to human NPC Fbs, the cells were pre-treated in the absence or presence of recombinant human acid SMase (rhASM) and then assayed for acid SMase activity and LSO fluorescence after filipin staining. As shown in FIG. 27A, the defect in acid SMase activity in the NPC Fbs was corrected by pre-treatment with rhASM. Most importantly, acid SMase replacement dramatically decreased LSO filipin fluorescence (FIG. 27B). Similar results were obtained using NPC1 skin fibroblasts from a different donor (GM18453) (FIG. 27C). Thus, restoration of acid SMase activity in NPC1 cells using two independent methods, genetic and enzyme replacement, has been shown to markedly correct the defect in LSO cholesterol accumulation.

Sub-Cellular Localization of Exogenously Added rhASM

Figure 28J:
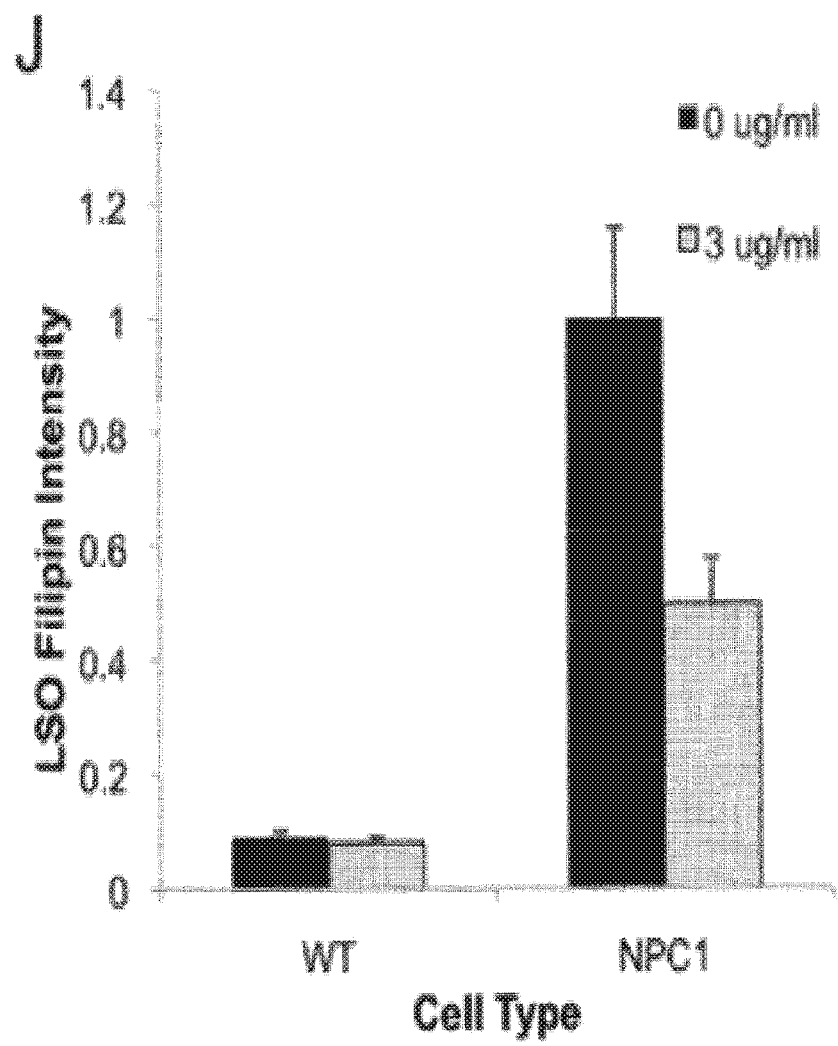
FIGS. 28 A-K: Addition of Alexa555-conjugated rhASM to demonstrate sub-cellular localization of exogenous acid SMase. WT (GM5659) and NPC (GM03123) Fbs were incubated with or without 3 µg/mL Alexa555-conjugated rhASM for 24 hours. To remove surface-bound label, the cells were further incubated for 15 min with a growth medium without the enzyme. Finally, the cells were washed with PBS, fixed with 1.5% PFA, and stained with filipin for imaging and quantification. The uptake of rhASM-Alexa555 was completely blocked when enzyme was added in the presence of excess mannose6-phosphate (10 mM) (data not shown). Filipin images in panels A, D and G, and the Alexa555 images in panels B, E and H, for WT, NPC1, and NPC1+rhASM-Alexa555, respectively, are displayed on the same gray scale range. Color overlays for filipin (green) and rhASM-Alexa555 (red) are shown in panels (C, F and I). The images in the inset are the zoomed color overlays of the region marked in (C, F and I). Scale bar=10 µm. Panel J shows the quantification of LSO filipin intensity after incubation with 0 or 3 µg/mL Alexa555 conjugated rhASM for 24 h in WT and NPC (GM03123) Fbs (values are ±SEM, $p<0.001$). Conjugation of Alexa555 to the enzyme did not affect its activity. Panel K shows the quantification of rhASM uptake after incubation with 0 and 3 µg/mL Alexa555 conjugated rhASM for 24 h in WT and NPC (GM03123) Fbs (values are ±SEM, $p<0.05$).
Figure 28K:
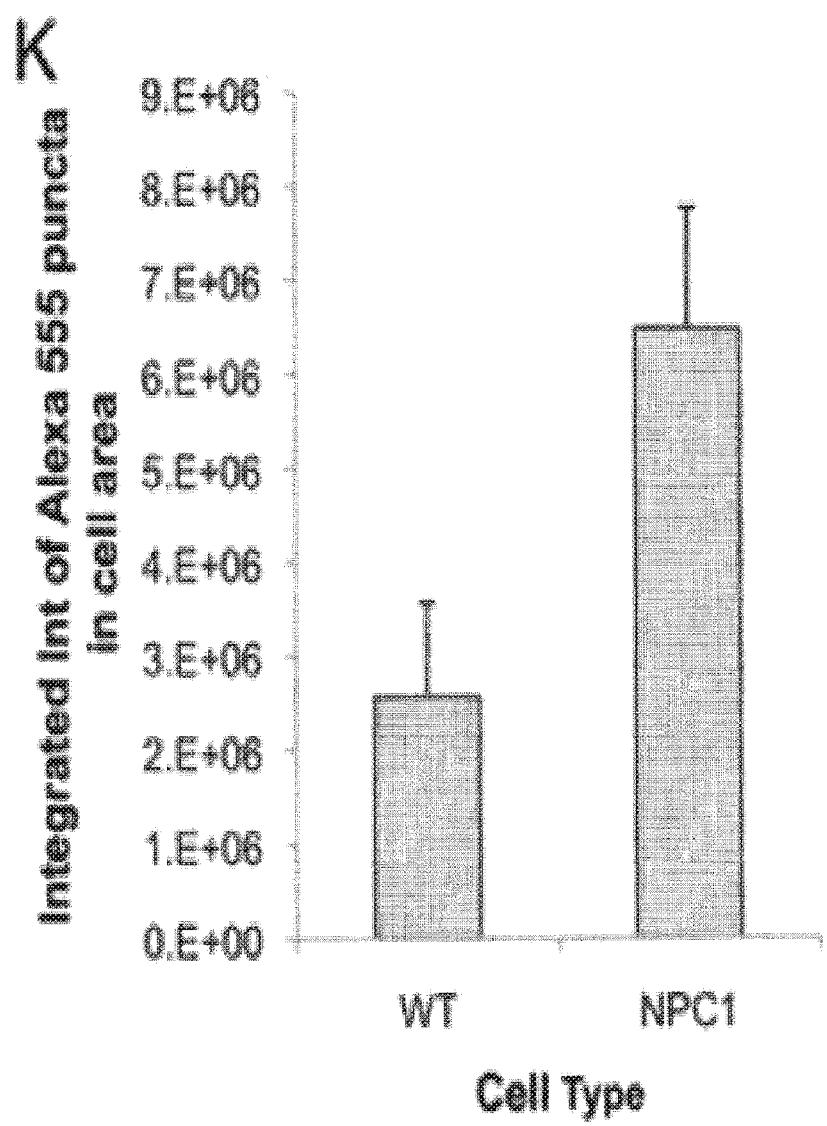

To ascertain whether exogenously added rhASM was localized and processed in late endosomal organelles, WT (GM05659) and NPC (GM03123) human fibroblasts were incubated for 24 hours in the absence or presence of 3 µg/mL of Alexa555-labeled rhASM. To remove surface labeling, the cells were further incubated for 15 minutes in a medium without enzyme. The cells were then washed, fixed and stained with filipin for imaging and quantification. The uptake of rhASM-Alexa555 was completely blocked when the enzyme was added in the presence of excess mannose-6-phosphate (10 mM) (data not shown). Conjugation of Alexa555 to the enzyme did not affect its activity (data not shown). Shown in FIG. 28 are filipin images (A, D and G) and Alexa555 images (B, E and H) for WT, NPC1 and NPC1+rhASM-Alexa555, respectively. Color overlays for filipin (green) and rhASM-Alexa555 (red) are shown in panels C, F and I of FIG. 28. The images in the inset are the zoomed color overlays of the regions marked in FIGS. 28 C, F, and I. Exogenously added rhASM-Alexa555, presumably internalized via the mannose-6-phosphate receptor, specifically localized to cholesterol-laden storage organelles (as shown in FIGS. 28 C and I) and was not visible in the plasma membrane or other cellular organelles. Quantification of LSO filipin and Alexa555-rhASM intensity after incubation with 0 or 3 µg/mL Alexa555 conjugated rhASM for 24 hours in WT and NPC (GM03123) Fbs (±SEM) is shown in FIGS. 28 J and K. Note that the higher level of uptake of the rhASM in the NPC Fbs may be at least partly explained by the previous finding that expression of IGF2/MPR is increased in human NPC fibroblast (Kobayashi 1999).

Overcoming Secondary Inactivation of Acid SMase

Figure 29A:
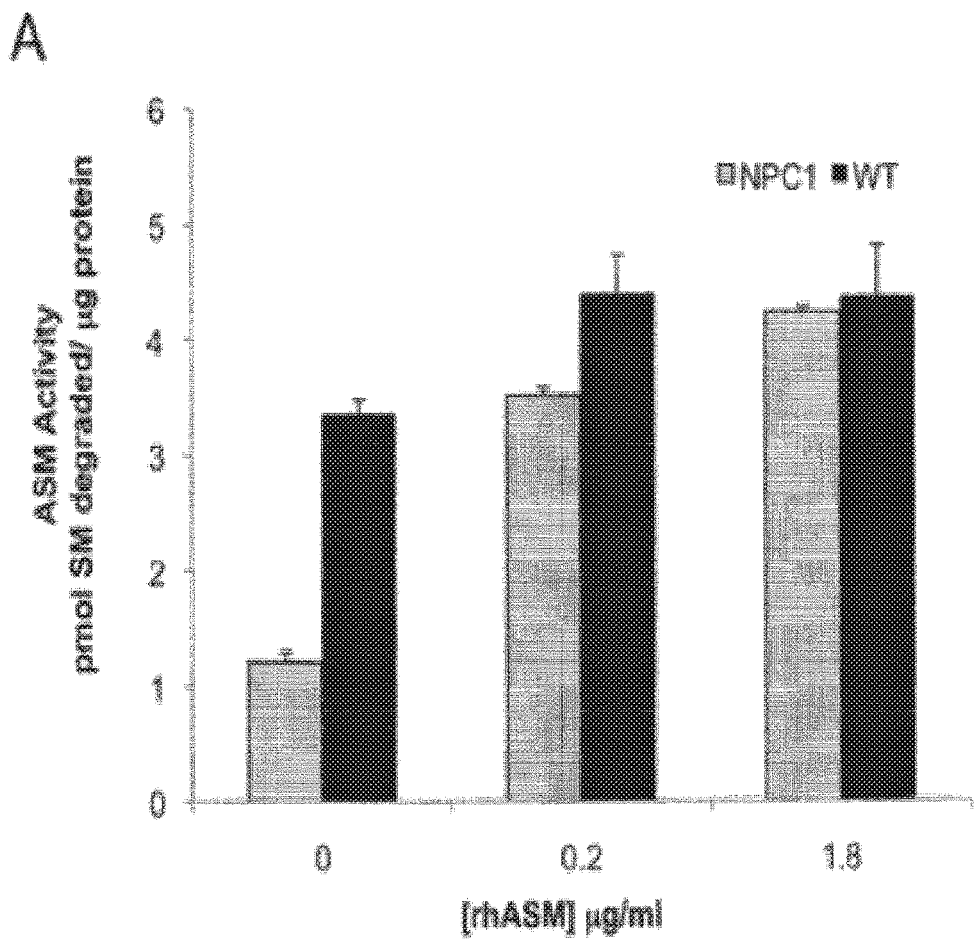
FIG. 29 A,B. Decreased LSO cholesterol accumulation and increased acid SMase activity are achieved in NPC1 human fibroblasts by increasing amounts of rhASM. WT (GM5659) and NPC (GM03123) Fbs were incubated with 0, 0.2 and 1.8 µg/mL rhASM for 24 hours. To remove surface-bound label, the cells were further incubated for 15 minutes with growth medium without the enzyme. The cells were washed thoroughly with PBS and either lysed and assayed for acid SMase activity (A) or fixed and stained with filipin for imaging and quantification (B). Each data point in plot (A) is representative of three wells in an experiment, $p<0.05$. Plot (B) represents LSO ratios normalized to the untreated NPC Fb GM01323 values (average of 16-20 images from two independent experiments±SEM), $p<0.005$.
Figure 29B:
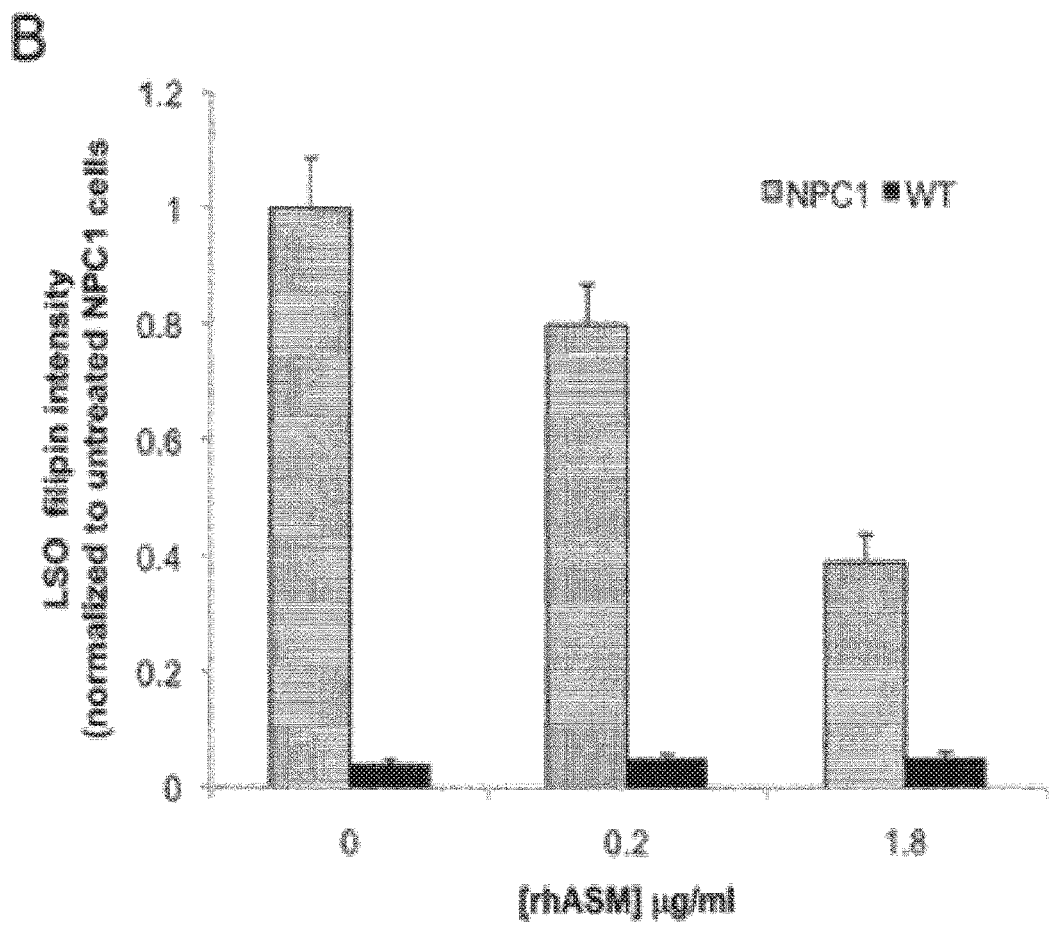

To validate the hypothesis that loss of acid SMase activity is a secondary effect of cholesterol storage in NPC1 patients, this experiment treated normal (GM05649) and NPC1 (GM03123) fibroblasts with 0, 0.2 and 1.8 µg/mL rhASM. Acid SMase activity was assayed in parallel with LSO filipin quantification as shown in FIG. 29 A,B. The acid SMase activity in wild-type fibroblasts (WT Fbs) (GM05659) increased slightly with 0.2 µg/mL rhASM (p<0.05), and the activity did not increase further at 1.8 µg/mL (black bars in FIG. 29A). The minimal amount of LSO filipin staining evident in normal fibroblasts (GM05659) remained low and constant for all doses of rhASM tested (black bars in FIG. 29B). In contrast, the addition of 0.2 µg/mL rhASM to NPC Fbs (GM03123) increased acid SMase activity significantly with a corresponding modest decrease in LSO filipin intensity (~20%), which indicates a decrease in LSO cholesterol accumulation (hashed bars in FIG. 29 A,B). Most importantly, increasing the rhASM dose to 1.8 µg/mL resulted in a marked reduction of LSO filipin intensity (~60%). Earlier experiments with genetic restoration of acid SMase in both CHO and human NPC1 mutant cells (FIGS. 22 and 26) showed an approximately 65-70% decrease in LSO filipin. Similarly, addition of rhASM back to human fibroblast at a higher (3 µg/mL) concentration (FIG. 27) also resulted in ~65-70% decrease in LSO filipin intensity. Thus, the inhibited acid SMase activity in NPC1 cells can be rescued by high-dose exogenous rhASM treatment, which presumably overcomes the enzyme inactivation process.

Discussion of Acid SMase Restoration Experiments

Figure 30:
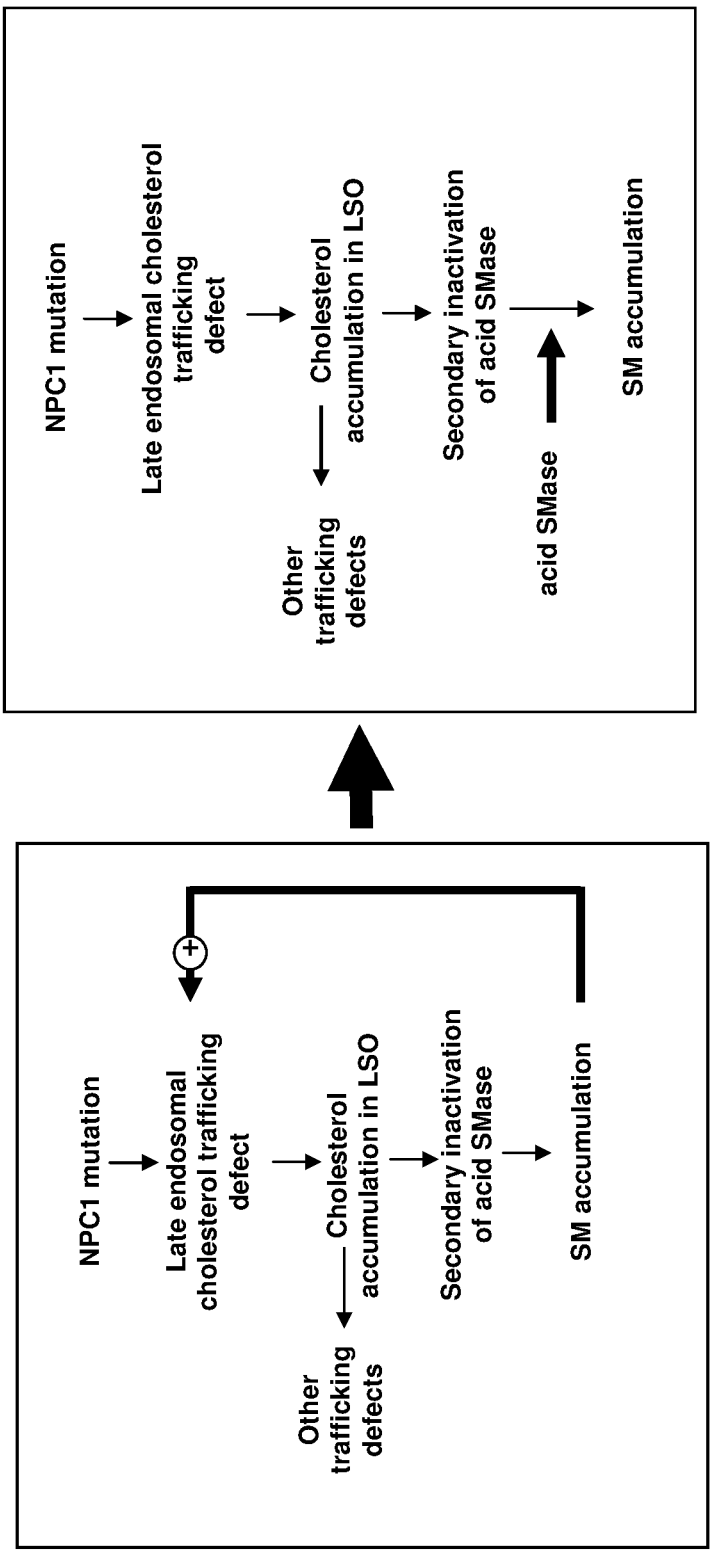
FIG. 30. Working model of how acid SMase ameliorates the trafficking defects in NPC1 deficient cells. The primary defect in cholesterol trafficking caused by mutant NPC1 leads to a secondary decrease in acid SMase activity. The decrease in acid SMase activity causes an increase in intracellular SM, presumably in late endosomes and possibly other sites, which amplifies the original cholesterol trafficking defect. Moreover, cholesterol accumulation in the LSO, and perhaps other effects of NPC1 deficiency, are associated with trafficking defects in other lipids, such as BMP, and perturbation of vesicular trafficking of membrane proteins, including TfR recycling. Thus, these defects would also be amplified by the secondary decrease in acid SMase activity. Restoring the defect in acid SMase activity breaks the amplification cycle and thus helps correct the aforementioned lipid and protein trafficking defects.

The panoply of cellular perturbations triggered by dysfunctional mutations in individual lysosomal enzymes, co-factors or transport proteins reflects multiple adverse effects of excess substrate accumulation (Brady 1982; Neufeld 1991). For LSDs involving the accumulation of certain lipids in LSOs, physical or biochemical consequences of accumulation of these excess lipids may lead to secondary effects on lysosomal/late endosomal processes that, in turn, could amplify the original defect or otherwise contribute to cellular pathology (FIG. 30). In any given LSD, one or more of these secondary defects may be particularly important, and those involving defects in lysosomal enzymes may be more amenable to correction than those involving the primary mutation (Neufeld 1980; Brady 2006). Thus, identification of such processes could reveal potentially promising therapeutic opportunities for certain LSDs. As an example, several sphingolipid LSDs acquire a secondary defect in late endosomal cholesterol trafficking which can exacerbate the lipid storage (Puri 1999; Lloyd-Evans 2008). In cell culture, correction of this secondary defect by cellular cholesterol depletion ameliorates a key defect in these cells, namely, abnormal trafficking of plasma membrane sphingolipids to lysosomes instead of the Golgi (Puri 1999). However, it remains unclear how sufficient cellular cholesterol depletion could be achieved to treat patients.

These experiments investigated the converse possibility that restoring SM hydrolysis in LSOs might reduce cholesterol storage and restore normal cellular membrane traffic. As a test case for this concept, the experiments studied NPC1 deficient cells. These cells lack a membrane-bound late endosomal protein NPC1, but have a secondary defect in a soluble lysosomal enzyme acid SMase that is amenable to reconstitution. The data show that correction of the secondary acid SMase defect in NPC1-deficient cells markedly reverses the accumulation of two lipids, cholesterol and BMP, and helps restore membrane TfR recycling—all in the face of a complete absence of the NPC1 protein (FIGS. 24 and 25).

If the suppression of acid SMase activity in NPC1 cells is a secondary effect, increasing levels of the enzyme may help overcome the inactivation. In support of this concept, it was observed in the instant experiments that adding increasing amounts of exogenous rhASM has no effect on cholesterol levels in WT cells. On the contrary, there is a dose-dependent decrease in ISO cholesterol with the addition of increasing dose of rhASM to NPC1 cells. The treatment is effective only after the secondary inactivation of acid SMase in these cells is overcome. Once this secondary defect is relieved by excess acid SMase, there is only 25-30% residual cholesterol accumulation, presumably because of the primary NPC1 mutation.

In summary, these experiments have shown that key pathological features of an LSD cell can be markedly improved by correcting a secondary abnormality despite complete absence of the protein responsible for the primary defect. In the case of NPC1 disease, the secondary defect of acid SMase inactivity is a more feasible therapeutic target than the primary mutation (Neufeld 1980; Brady 2006). The data in FIGS. 27 A-C demonstrate this concept at the cell level by showing that the LSO cholesterol trafficking defect in two different human NPC Fbs can be markedly corrected by acid SMase enzyme replacement. A reduction of up to 70% of the cholesterol overload in LSOs might translate into clinical improvement. Indeed, replacement therapy with acid SMase is being tested in humans who have NPA and B disease with primary mutations in this protein (Schuchman 2007). The challenge with NPC disease is to achieve expression in the brain, but recent advances using SMPD1-containing adeno-associated virus vectors in mice have shown promise in this regard (Passini 2005; Dodge 2005).

REFERENCES RELEVANT TO ACID SMASE RESTORATION EXPERIMENTS

Bartlett G R. Phosphorus assay in column chromatography. J Biol Chem 1959; 234:466-468.

Bartz F, Kern L, Erz D, Zhu M, Gilbert D, Meinhof T, Wirkner U, Erfle H, Muckenthaler M, Pepperkok R, Runz H. Identification of cholesterol-regulating genes by targeted RNAi screening. Cell Metab 2009; 10:63-75.

Brady R O, Filling-Katz M R, Barton N W, Pentchev P G. Niemann-Pick disease types C and D. Neurol Clin 1989; 7:75-88.

Brady R O. Enzyme replacement for lysosomal diseases. Annu Rev Med 2006; 57:283-296.

Brady R O. Lysosomalstorage diseases. Pharmacol Ther 1982; 19: 327-336.

Cadigan K M, Spillane D M, Chang T-Y. Isolation and characterization of Chinese hamster ovary cell mutants defective in intracellular low density lipoprotein-cholesterol trafficking. J Cell Biol 1990; 110:295-308.

Chang T Y, Limanek J S. Regulation of cytosolic acetoacetyl coenzyme A thiolase, 3-hydroxy-3-methylglutaryl coenzyme A synthase, 3-hydroxy-3-methylglutaryl coenzyme A reductase, and mevalonate kinase by low density lipoprotein and by 25-hydroxycholesterol in Chinese hamster ovary cells. J Biol Chem 1980; 255:7787-7795.

Cheruku S R, Xu Z, Dutia R, Lobel P, Storch J. Mechanism of cholesterol transfer from the Niemann-Pick type C2 protein to model membranes supports a role in lysosomal cholesterol transport. J Biol Chem 2006; 281:31594-31604.

Chevallier J, Chamoun Z, Jiang G, Prestwich G, Sakai N, Matile S, Parton R G, Gruenberg J. Lysobisphosphatidic acid controls endosomal cholesterol levels. J Biol Chem 2008; 283:27871-27880.

Choudhury A, Sharma D K, Marks D L, Pagano R E. Elevated endosomal cholesterol levels in Niemann-Pick cells inhibit rab4 and perturb membrane recycling. Mol Biol Cell 2004; 15:4500-4511.

Dodge J C, Clarke J, Song A, Bu J, Yang W, Taksir T V, Griffiths D, Zhao M A, Schuchman E H, Cheng S H, O'Riordan C R, Shihabuddin L S, Passini M A, Stewart G R. Gene transfer of human acid sphingomyelinase corrects neuropathology and motor deficits in a mouse model of Niemann-Pick type A disease. Proc Natl Acad Sci USA 2005; 102:17822-17827.

Dvorakova L, Sikora J, Hrebicek M, Hulkova H, Bouckova M, Stolnaja L, Elleder M. Subclinical course of adult visceral Niemann-Pick type C1 disease. A rare or under-diagnosed disorder? J Inherit Metab Dis 2006; 29:591.

Griffin L D, Gong W, Verot L, Mellon S H. Niemann-Pick type C disease involves disrupted neurosteroidogenesis and responds to allopregnanolone. Nat Med 2004; 10:704-711.

Harzer K, Massenkeil G, Frohlich E. Concurrent increase of cholesterol, sphingomyelin and glucosylceramide in the spleen from non-neurologic Niemann-Pick type C patients but also patients possibly affected with other lipid trafficking disorders. FEBS Lett 2003; 537:177-181.

Havel R J, Eder H, Bragdon J. The distribution and chemical composition of ultracentrifugally reported lipoproteins in human serum. J Clin Invest 1955; 34:1345-1353.

He X, Miranda S R P, Dagan A, Gatt S, Schuchman E H. Overexpression of human acid sphingomyelinase in Chinese hamster ovary cells. Purification and characterization of the recombinant enzyme. Biochim Biophys Acta 1999; 1432:251-264.

Huang J, Feigenson G W. A microscopic interaction model of maximum solubility of cholesterol in lipid bilayers. Biophys J 1999; 76:2142-2157.

Infante R E, Wang M L, Radhakrishnan A, Kwon H J, Brown M S, Goldstein J L. NPC2 facilitates bidirectional transfer of cholesterol between NPC1 and lipid bilayers, a step in cholesterol egress from lysosomes. Proc Natl Acad Sci USA 2008; 105:15287-15292.

Johnson A O, Lampson M A, McGraw T E. A di-leucine sequence and a cluster of acidic amino acids are required for dynamic retention in the endosomal recycling compartment of fibroblasts. Mol Biol Cell 2001; 12:367-381.

Karten B, Vance D E, Campenot R B, Vance J E. Cholesterol accumulates in cell bodies, but is decreased in distal axons, of Niemann-Pick C1-deficient neurons. J Neurochem 2002; 83:1154-1163.

Kobayashi T, Beuchat M H, Lindsay M, Frias S, Palmiter R D, Sakuraba H, Parton R G, Gruenberg J. Late endosomal membranes rich in lysobisphosphatidic acid regulate cholesterol transport. Nat Cell Biol 1999; 1:113-118.

Krieger M. Reconstitution of the hydrophobic core of low-density lipoprotein. Methods Enzymol 1986; 128:608-613.

Langmade S J, Gale S E, Frolov A, Mohri I, Suzuki K, Mellon S H, Walkley S U, Covey D F, Schaffer J E, Ory D S. Pregnane X receptor (PXR) activation: a mechanism for neuroprotection in a mouse model of Niemann-Pick C disease. Proc Natl Acad Sci USA 2006; 103:13807-13812.

Leventhal A R, Chen W, Tall A R, Tabas I. Acid sphingomyelinasedeficient macrophages have defective cholesterol trafficking and efflux. J Biol Chem 2001; 276:44976-44983.

Liscum L, Klansek J J. Niemann-Pick disease type C. Curr Opin Lipidol 1998; 9:131-135.

Lloyd-Evans E, Morgan A J, He X, Smith D A, Elliot-Smith E, Sillence D J, Churchill G C, Schuchman E H, Galione A, Platt F M. Niemann-Pick disease type C1 is a sphingosine storage disease that causes deregulation of lysosomal calcium. Nat Med 2008; 14:1247-1255.

Lowry O H, Rosenbrough N J, Farr A L, Randall R J. Protein measurement with the folin phenol reagent. J Biol Chem 1951; 193: 265-275.

Maguire J A, Reagan J W Jr. Silencing of the mutant SCAP allele accounts for restoration of a normal phenotype in CT60 cells selected for NPC1 expression. J Lipid Res 2005; 46:1840-1848.

Maziere J C, Maziere C, Mora L, Routier J D, Polonovski J. In situ degradation of sphingomyelin by cultured normal fibroblasts and fibroblasts from patients with Niemann-Pick disease type A and C. Biochem Biophys Res Commun 1982; 108:1101-1106.

Megha, London E. Ceramide selectively displaces cholesterol from ordered lipid domains (rafts): implications for lipid raft structure and function. J Biol Chem 2004; 279:9997-10004.

Mukherjee S, Maxfield F R. Lipid and cholesterol trafficking in NPC. Biochim Biophys Acta 2004; 1685:28-37.

Neufeld E F. The uptake of enzymes into lysosomes: an overview. Birth Defects Orig Artic Ser 1980; 16:77-84.

Neufeld E F. Lysosomal storage diseases. Annu Rev Biochem 1991; 60:257-280.

Okwu A K, Xu X, Shiratori Y, Tabas I. Regulation of the threshold for lipoprotein-induced acyl-CoA:cholesterol O-acyltransferase stimulation in macrophages by cellular sphingomyelin content. J Lipid Res 1994; 35:644-655.

Ory D S. The Niemann-Pick disease genes; regulators of cellular cholesterol homeostasis. Trends Cardiovasc Med 2004; 14:66-72.

Passini M A, Macauley S L, Huff M R, Taksir T V, Bu J, Wu I H, Piepenhagen P A, Dodge J C, Shihabuddin L S, O'Riordan C R, Schuchman E H, Stewart G R. AAV vector-mediated correction of brain pathology in a mouse model of Niemann-Pick A disease. Mol Ther 2005; 11:754-762.

Pentchev P G, Comly M E, Kruth H S, Vanier M T, Wenger D A, Patel S, Brady R O. A defect in cholesterol esterification in Niemann-Pick disease (type C) patients. Proc Natl Acad Sci USA 1985; 82:8247-8251.

Pentchev P G, Gal A E, Booth A D, Omodeo-Sale F, Fouks J, Neumeyer B A, Quirk J M, Dawson G, Brady R O. A lysosomal storage disorder in mice characterized by a dual deficiency of sphingomyelinase and glucocerebrosidase. Biochim Biophys Acta 1980; 619:669-679.

Pentchev P G. Niemann-Pick C research from mouse to gene. Biochim Biophys Acta 2004; 1685:3-7.

Pipalia N H, Hao M, Mukherjee S, Maxfield F R. Sterol, protein and lipid trafficking in Chinese hamster ovary cells with Niemann-Pick type C1 defect. Traffic 2007; 8:130-141.

Pipalia N H, Huang A, Ralph H, Rujoi M, Maxfield F R. Automated microscopy screening for compounds that partially revert cholesterol accumulation in Niemann-Pick C cells. J Lipid Res 2006; 47: 284-301.

Puri V, Watanabe R, Dominguez M, Sun X, Wheatley C L, Marks D L, Pagano R E. Cholesterol modulates membrane traffic along the endocytic pathway in sphingolipid-storage diseases. Nat Cell Biol 1999; 1:386-388.

Qin C, Nagao T, Grosheva I, Maxfield F R, Pierini L M. Elevated plasma membrane cholesterol content alters macrophage signaling and function. Arterioscler Thromb Vasc Biol 2006; 26:372-378.

Qiu H, Edmunds T, Baker-Malcolm J, Karey K P, Estes S, Schwarz C, Hughes H, Van Patten S M. Activation of human acid sphingomyelinase through modification or deletion of C-terminal cysteine. J Biol Chem 2003; 278: 32744-32752.

Radhakrishnan A, Anderson T G, McConnell H M. Condensed complexes, rafts, and the chemical activity of cholesterol in membranes. Proc Natl Acad Sci USA 2000; 97:12422-12427.

Reagan J W Jr, Hubbert M L, Shelness G S. Posttranslational regulation of acid sphingomyelinase in Niemann-Pick type C1 fibroblasts and free cholesterol-enriched Chinese hamster ovary cells. J Biol Chem 2000; 275:38104-38110.

Reid P C, Sakashita N, Sugii S, Ohno-Iwashita Y, Shimada Y, Hickey W F, Chang T Y. A novel cholesterol stain reveals early neuronal cholesterol accumulation in the Niemann-Pick type C1 mouse brain. J Lipid Res 2004; 45:582-591.

Ridgway N D. Interactions between metabolism and intracellular distribution of cholesterol and sphingomyelin. Biochim Biophys Acta 2000; 1484:129-141.

Salvioli R, Scarpa S, Ciaffoni F, Tatti M, Ramoni C, Vanier M T, Vaccaro A M. Glucosylceramidase mass and subcellular localization are modulated by cholesterol in Niemann-Pick disease type C. J Biol Chem 2004; 279: 17674-17680.

Sarna J, Miranda S R, Schuchman E H, Hawkes R. Patterned cerebellar Purkinje cell death in a transgenic mouse model of Niemann-Pick type A/B disease. Eur J Neurosci 2001; 13:1873-1880.

Sarna J R, Larouche M, Marzban H, Sillitoe R V, Rancourt D E, Hawkes R. Patterned Purkinje cell degeneration in mouse models of Niemann-Pick type C disease. J Comp Neurol 2003; 456:279-291.

Schuchman E H. The pathogenesis and treatment of acid sphingomyelinase-deficient Niemann-Pick disease. J Inherit Metab Dis 2007; 30:654-663.

Slotte J P, Bierman E L. Depletion of plasma-membrane sphingomyelin rapidly alters the distribution of cholesterol between plasma membranes and intracellular cholesterol pools in cultured fibroblasts. Biochem J 1988; 250:653-658.

Tamura H, Takahashi T, Ban N, Torisu H, Ninomiya H, Takada G, Inagaki N. Niemann-Pick type C disease: novel NPC1 mutations and characterization of the concomitant acid sphingomyelinase deficiency. Mol Genet Metab 2006; 87:113-121.

Thomas G H, Tuck-Muller C M, Miller C S, Reynolds L W. Correction of sphingomyelinase deficiency in Niemann-Pick type C fibroblasts by removal of lipoprotein fraction from culture media. J Inherit Metab Dis 1989; 12:139-151.

Urano Y, Watanabe H, Murphy S R, Shibuya Y, Geng Y, Peden A A, Chang C C, Chang T Y. Transport of LDL-derived cholesterol from the NPC1 compartment to the ER involves the trans-Golgi network and the SNARE protein complex. Proc Natl Acad Sci USA 2008; 105: 16513-16518.

Vanier M T, Revol A, Fichet M. Sphingomyelinase activities of various human tissues in control subjects and in Niemann-Pick disease—development and evaluation of a microprocedure. Clin Chim Acta 1980; 106:257-267.

Vanier M T, Rodriguez-Lafrasse C, Rousson R, Gazzah N, Juge M C, Pentchev P G, Revol A, Louisot P. Type C Niemann-Pick disease: spectrum of phenotypic variation in disruption of intracellular LDL-derived cholesterol processing. Biochim Biophys Acta 1991; 1096:328-337.

Walkley S U, Suzuki K. Consequences of NPC1 and NPC2 loss of function in mammalian neurons. Biochim Biophys Acta 2004; 1685: 48-62.

Watari H, Blanchette-Mackie E J, Dwyer N K, Glick J M, Patel S, Neufeld E B, Brady R O, Pentchev P G, Strauss J F III. Niemann-PickC1 protein: obligatory roles for N-terminal domains and lysosomal targeting in cholesterol mobilization. Proc Natl Acad Sci USA 1999; 96:805-810.

Yamamoto T, Ninomiya H, Matsumoto M, Ohta Y, Nanba E, Tsutsumi Y, Yamakawa K, Millat G, Vanier M T, Pentchev P G, Ohno K. Genotype-phenotype relationship of Niemann-Pick disease type C: a possible correlation between clinical onset and levels of NPC1 protein in isolated skin fibroblasts. J Med Genet 2000; 37:707-712.

Yerushalmi B, Sokol R J, Narkewicz M R, Smith D, Ashmead J W, Wenger D A. Niemann-Pick disease type C in neonatal cholestasis at a North American Center. J Pediatr Gastroenterol Nutr 2002; 35:44-50.

Zervas M, Dobrenis K, Walkldey S U. Neurons in Niemann-Pick disease type C accumulate gangliosides as well as unesterified cholesterol and undergo dendritic and axonal alterations. J Neuropathol Exp Neurol 2001; 60:49-64.

While there have been shown and described what are at present considered the preferred embodiments of the invention, those skilled in the art may make various changes and modifications which remain within the scope of the invention defined by the appended claims.

What is claimed is:

1. A method for lowering a cholesterol level in a patient, the method comprising administering to said patient a composition consisting essentially of a therapeutically effective amount of a polysaccharide having attached thereto at least one cyclodextrin and a cell-targeting agent, wherein said cyclodextrin is an alkylated cyclodextrin having at least one hydroxyl group of the cyclodextrin modified by substitution of a hydrogen atom of the hydroxyl group with a hydrocarbon group.

2. A method for treating a mammal suffering from a lysosomal storage disorder resulting in an accumulation of lipids, the method comprising administering to said mammal a polymer composition comprising an active portion comprising a polysaccharide having attached thereto at least one cyclodextrin.

3. The method of claim 2, wherein said polymer composition further comprises a cell-targeting agent attached to said active portion.

4. The method of claim 2, wherein said lysosomal storage disorder is a Niemann-Pick disease.

5. The method of claim 1, wherein said at least one cyclodextrin is attached as a pendant group from the polysaccharide.

6. The method of claim 1, wherein said alkylated cyclodextrin is a permethylated cyclodextrin.

7. The method of claim 1, wherein said alkylated cyclodextrin is a hydroxypropyl cyclodextrin.

8. The method of claim 1, wherein said cell-targeting agent targets an entity residing on a surface of a cell.

9. The method of claim 1, wherein said cell-targeting agent targets a lysosome.

10. The method of claim 9, wherein said cell-targeting agent is mannose-6-phosphate.

11. The method of claim 1, wherein said polysaccharide is a dextran.

12. The method of claim 1, wherein said polysaccharide has a molecular weight of at least 40,000 Da.

13. The method of claim 2, wherein said at least one cyclodextrin is attached as a pendant group from the polysaccharide.

14. The method of claim 2, wherein said cyclodextrin is an alkylated cyclodextrin by having at least one hydroxyl group of the cyclodextrin modified by substitution of a hydrogen atom of the hydroxyl group with a hydrocarbon group.

15. The method of claim 14, wherein said alkylated cyclodextrin is a permethylated cyclodextrin.

16. The method of claim 14, wherein said alkylated cyclodextrin is a hydroxypropyl cyclodextrin.

17. The method of claim 3, wherein said cell-targeting agent targets an entity residing on a surface of a cell.

18. The method of claim 3, wherein said cell-targeting agent targets a lysosome.

19. The method of claim 18, wherein said cell-targeting agent is mannose-6-phosphate.

20. The method of claim 2, wherein said polysaccharide is a dextran.

21. The method of claim 2, wherein said polysaccharide has a molecular weight of at least 40,000 Da.

22. The method of claim 1, wherein said cyclodextrin is unloaded when administered to the patient.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 1
actgtctgaa gagctggagc t                                              21

<210> SEQ ID NO 2
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 2
ttttattgcg gccgcctagc aaaacagtgg ccttgg                              36

<210> SEQ ID NO 3
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 3
ttttattgcg gccgcctagg aaaacagtgg ccttgg                              36
```